(12) United States Patent
Tanoshima et al.

(10) Patent No.: US 6,938,502 B2
(45) Date of Patent: Sep. 6, 2005

(54) AUTOMATIC SAMPLE ANALYZER AND ITS COMPONENTS

(75) Inventors: Eiji Tanoshima, Kobe (JP); Kazuyuki Sakurai, Akashi (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 10/899,172

(22) Filed: Jul. 27, 2004

(65) Prior Publication Data

US 2005/0074361 A1 Apr. 7, 2005

Related U.S. Application Data

(62) Division of application No. 10/235,955, filed on Sep. 6, 2002, now Pat. No. 6,772,650.

(30) Foreign Application Priority Data

| Sep. 6, 2001 | (JP) | 2001-270543 |
| Sep. 7, 2001 | (JP) | 2001-272483 |
| Sep. 7, 2001 | (JP) | 2001-272484 |
| Sep. 7, 2001 | (JP) | 2001-272485 |
| Sep. 7, 2001 | (JP) | 2001-272486 |
| Sep. 7, 2001 | (JP) | 2001-272487 |
| Sep. 11, 2001 | (JP) | 2001-275375 |
| Sep. 11, 2001 | (JP) | 2001-275385 |
| Sep. 11, 2001 | (JP) | 2001-275397 |
| Nov. 20, 2001 | (JP) | 2001-355093 |
| Nov. 28, 2001 | (JP) | 2001-362979 |
| Apr. 10, 2002 | (JP) | 2002-108113 |
| Apr. 26, 2002 | (JP) | 2002-126640 |

(51) Int. Cl.$^7$ .............................................. G01N 1/10
(52) U.S. Cl. ........................ 73/863.01; 73/864.21
(58) Field of Search .................. 73/863.01, 863.02, 73/863.03, 863.81, 863.82, 863.83, 864.21

(56) References Cited

U.S. PATENT DOCUMENTS

| 5,211,310 A | * | 5/1993 | Godolphin et al. | ............ 222/1 |
| 5,322,192 A | * | 6/1994 | Godolphin et al. | ........... 222/83 |
| 5,367,888 A | * | 11/1994 | Muston et al. | ................ 62/292 |
| 5,413,246 A | * | 5/1995 | Godolphin et al. | ............ 222/1 |
| 5,441,415 A | * | 8/1995 | Lee et al. | .................... 434/350 |
| 5,577,837 A | * | 11/1996 | Martin et al. | ............... 366/145 |
| 5,592,959 A | | 1/1997 | Nagai | |
| 5,627,531 A | * | 5/1997 | Posso et al. | .................. 341/22 |
| 5,788,508 A | * | 8/1998 | Lee et al. | .................... 434/350 |
| 5,969,272 A | | 10/1999 | Tanaka | |
| 6,171,280 B1 | | 1/2001 | Imazu et al. | |
| 6,319,718 B1 | * | 11/2001 | Matsubara et al. | ........... 436/47 |

FOREIGN PATENT DOCUMENTS

| JP | 11-094842 A | 4/1999 |
| WO | WO 92/22798 A1 | 12/1992 |

* cited by examiner

*Primary Examiner*—Charles Garber
(74) *Attorney, Agent, or Firm*—Birch, Stewart, Kolasch & Birch, LLP.

(57) ABSTRACT

An automatic sample analyzer includes: a pipette, a pipette driving device which moves the pipette to a sample vessel present in a predetermined position to cause the pipette to suck up a sample from the sample vessel, and then moves the pipette to an open vessel provided in another predetermined position to cause the pipette to discharge the sample into the open vessel, and an analyzing section for analyzing the discharged sample, the pipette driving device comprising a vertically movable main arm and an elongated guide arm cantilevered by the main arm and extending horizontally, the guide arm having a smaller flexural rigidity than the main arm, wherein the main arm vertically moves the pipette when the sample is to be sucked up from the sample vessel, and the guide arm guides the pipette to the open vessel and then vertically moves the pipette when the sample is to be discharged into the open vessel.

6 Claims, 65 Drawing Sheets

FIG.42(a)

```
┌─────────────────────────────┐
│   Ready    ┌───┐   ┌──────┐ │
│ [ Main  ]  │P/F│   │ Menu │ │
│            └───┘   └──────┘ │
│  Sample ID      Set a mixed │
│  ┌──────────┐   sample, and │
│  │        1 │   press [RUN] │
│  └──────────┘               │
│  Analysis Mode              │
│  ┌──┐ ┌──┐   ┌──────┐       │
│  │WB│ │PD│   │ RUN  │       │
│  └──┘ └──┘   └──────┘       │
│  Whole Blood                │
│  ┌─┬─┬──────┐      ┌───────┐│
│  │Q│C│Result│      │Shutdown││
│  └─┴─┴──────┘      └───────┘│
└─────────────────────────────┘
```

FIG.42(b)

```
┌────────────────────────────────┐
│  Running  ┌───┐      ┌─────┐   │
│ [ Result] │P/F│      │ Top │   │
│           └───┘      └─────┘   │
│ ID    12345   WB  01/01/2001 12:10│
│   WBC              ×10³/uL     │
│   RBC              ×10⁶/uL     │
│   HGB              g/dL        │
│   HCT              %           │
│   PLT              ×10³/uL     │
│                                │
│  ▶▶▶▶▷▷▷▷                      │
└────────────────────────────────┘
```

FIG.42(c)

```
┌────────────────────────────────┐
│  Running  ┌───┐      ┌─────┐   │
│ [ Result] │P/F│      │ Top │   │
│           └───┘      └─────┘   │
│ ID    12345   WB  01/01/2001 12:10│
│   WBC        7.6   ×10³/uL     │
│   RBC              ×10⁶/uL     │
│   HGB       14.9   g/dL        │
│   HCT              %           │
│   PLT              ×10³/uL     │
│                                │
│  ▶▶▶▶▶▶▷▷                      │
└────────────────────────────────┘
```

FIG.42(d)

```
┌────────────────────────────────┐
│  Running  ┌───┐      ┌─────┐   │
│ [ Result] │P/F│      │ Top │   │
│           └───┘      └─────┘   │
│ ID    12345   WB  01/01/2001 12:10│
│   WBC        7.6   ×10³/uL     │
│   RBC        4.79  ×10⁶/uL     │
│   HGB       14.9   g/dL        │
│   HCT       44.6   %           │
│   PLT        224   ×10³/uL     │
│                           1/4  │
│ ┌─────┬──────┐           ┌───┐ │
│ │Print│HC Out│           │ → │ │
│ └─────┴──────┘           └───┘ │
└────────────────────────────────┘
```

FIG.42(e)

```
┌────────────────────────────────┐
│  Running  ┌───┐      ┌─────┐   │
│ [ Result] │P/F│      │ Top │   │
│           └───┘      └─────┘   │
│ ID    12345   WB  01/01/2001 12:10│
│   WBC       7.6   ×10³/uL      │
│   RBC       4.79  ×10⁶/uL      │
│   HGB      14.9   g/dL         │
│   HCT      44.6   %            │
│   MCV      93.1   fL           │
│   MCH      31.1   pg           │
│   MCHC     33.4   g/dL         │
│   PLT       224   ×10³/uL      │
│                           2/4  │
│ ┌─────┬──────┐           ┌───┐ │
│ │Print│HC Out│           │ → │ │
│ └─────┴──────┘           └───┘ │
└────────────────────────────────┘
```

AUTOMATIC SAMPLE ANALYZER AND ITS COMPONENTS

CROSS-REFERENCES TO RELATED APPLICATIONS

This application is a Divisional of co-pending application No. 10/235,955, filed on Sep. 6, 2002, now U.S. Pat. No. 6,772,650 and for which priority is claimed under 35 U.S.C. § 120; the entire contents of which is hereby incorporated by reference.

Further, this application is related to Japanese Patent Application Nos. 2001-270543 (filed on Sep. 6, 2001), 2001-272483 (filed on Sep. 7, 2001), 2001-272484 (filed on Sep. 7, 2001), 2001-272485 (filed on Sep. 7, 2001), 2001-272486 (filed on Sep. 7, 2001), 2001-272487 (filed on Sep. 7, 2001), 2001-275375 (filed on Sep. 11, 2001), 2001-275385 (filed on Sep. 11, 2001), 2001-275397 (filed on Sep. 11, 2001), 2001-355093 (filed on Nov. 20, 2001), 2001-362979 (filed on Nov. 28, 2001), 2002-108113 (filed on Apr. 10, 2002) and 2002-126640 (filed on Apr. 26, 2002); whose priorities are claimed under 35 U.S.C. § 119, the disclosures of which are incorporated by reference in their entirety.

BACKGROUND OF THE INVENTION

1. Field of the Invention

This invention relates to a sample analyzer and its components and, particularly, to a highly versatile and small-scale sample analyzer for analyzing a blood sample, a urine sample and the like.

2. Description of the Related Art

Art hitherto known in relation to this invention is as follows.

A small-scale automatic analyzer comprising a reaction vessel disk having a reaction table with its circumferential portion equidistantly divided into a plurality of portions, a plurality of reaction vessels held by the reaction vessel disk, means for transporting the respective reaction vessels to a sample dispenser, to an agent dispensing position and to an optically measuring position, means for sucking and dispensing a required amount of a sample into the reaction vessel, and means for optically analyzing the sample in the reaction vessel (see, for example, Japanese Unexamined Patent Publication No. 11-94842 (1999));

A liquid suction device adapted to move a pipette with respect to an open sample vessel by utilizing the torque of a first motor and move the pipette with respect to a closed sample vessel by utilizing the torque of a second motor (see, for example, U.S. Pat. No. 6,171,280);

An assembly comprising a longitudinally compressible and extendible hollow cleaning chamber, a pipette which is adapted to be accommodated in the cleaning chamber when the cleaning chamber is expanded and to project from the cleaning chamber when the cleaning chamber is compressed, and a lock device for locking the cleaning chamber in an expanded state (see International Publication No. 92/22798);

A pipette comprising a hollow pipe having an end sealed with a seal member, and a suction port provided in a side wall of the pipe adjacent in the vicinity of the end (see, for example, U.S. Pat. No. 5,969,272);

A pipette comprising a thin suction pipe for sucking a liquid sample, and a thin vent pipe for ventilation during the suction, the suction pipe and the vent pipe being disposed in side-by-side relation (see, for example, U.S. Pat. No. 5,969,272);

A pipette cleaning device comprising a pipette generally vertically disposed with a liquid sample intake port thereof being oriented downward, a pipette exterior cleaning member having a generally vertical through-path in which the pipette is loosely fitted, a feed path for feeding a cleaning liquid into the through-path, and a drain path for draining a waste cleaning liquid from the through-path, pipette interior cleaning means connected to the pipette for feeding the cleaning liquid into the interior of the pipette, a cleaning liquid reservoir chamber connected to the feed path of the cleaning member and the pipette interior cleaning means, suction means connected to the drain path of the cleaning member for sucking the waste cleaning liquid from the pipette, a waste liquid reservoir chamber connected to the drain path for storing the waste cleaning liquid sucked out by the suction means, and driving means for moving up and down at least one of the cleaning member and the pipette to change a positional relationship between the cleaning member and the pipette, wherein the through-path has a smaller diameter portion spaced a smaller distance from the pipette and a greater diameter portion provided below the smaller diameter portion and spaced a greater distance from the pipette than the smaller diameter portion, wherein the feed path and the drain path communicate with the greater diameter portion and the smaller diameter portion, respectively (see, for example, U.S. Pat. No. 5,592,959); and A pipette cleaning device comprising a through-path in which a pipette having a suction port provided at a tip end thereof is inserted, a feed path for supplying a cleaning liquid into the through-path, and a drain path for draining a waste cleaning liquid from the through-path (see, for example, U.S. Pat. No. 5,592,959).

There have been proposed various types of automatic sample analyzers such as automatic blood analyzers. Most of the recent automatic analyzers have a greater size and a higher operation speed to handle a multiplicity of samples in a short time. In addition, the operation of the automatic analyzers is complicated, so that special operators should be employed as regular staff. Local hospitals and private clinics which do not frequently need clinical analyses currently commission a special analysis center to perform the clinical analyses. However, it is impossible to immediately obtain the results of clinical analyses in an emergency case. Therefore, there is a demand for a highly versatile, easy-to-operate and small-scale automatic sample analyzer.

SUMMARY OF THE INVENTION

In view of the foregoing, it is an object of the present invention to simplify the operation of an automatic sample analyzer for easy handling of the analyzer by doctors and nurses, reduce the size and weight of the analyzer for easy transportation of the analyzer to diagnostic and medical treatment sites, suppress the noises of the analyzer for a quiet environment, and ensure safe and easy maintenance and inspection of the analyzer, and energy saving of the analyzer.

In accordance with the present invention, there is provided an automatic sample analyzer, which comprises: a pipette; a pipette driving device which moves the pipette to a sample vessel present in a predetermined position to cause the pipette to suck up a sample from the sample vessel, and then moves the pipette to an open vessel provided in another predetermined position to cause the pipette to discharge the sample into the open vessel; and an analyzing section for analyzing the discharged sample; the pipette driving device comprising a vertically movable main arm and an elongated guide arm cantilevered by the main arm and extending horizontally; the guide arm having a smaller flexural rigidity than the main arm; wherein the main arm vertically moves the pipette when the sample is to be sucked up from the sample vessel, and the guide arm guides the pipette to the open vessel and then vertically moves the pipette when the sample is to be discharged into the open vessel.

BRIEF DESCRIPTION OF THE DRAWINGS

FIGS. 42(a) to 42(e) are diagrams illustrating screen images to be successively displayed on the blood analyzer according to this invention;

DESCRIPTION OF THE PREFERRED EMBODIMENTS

Figure 1:
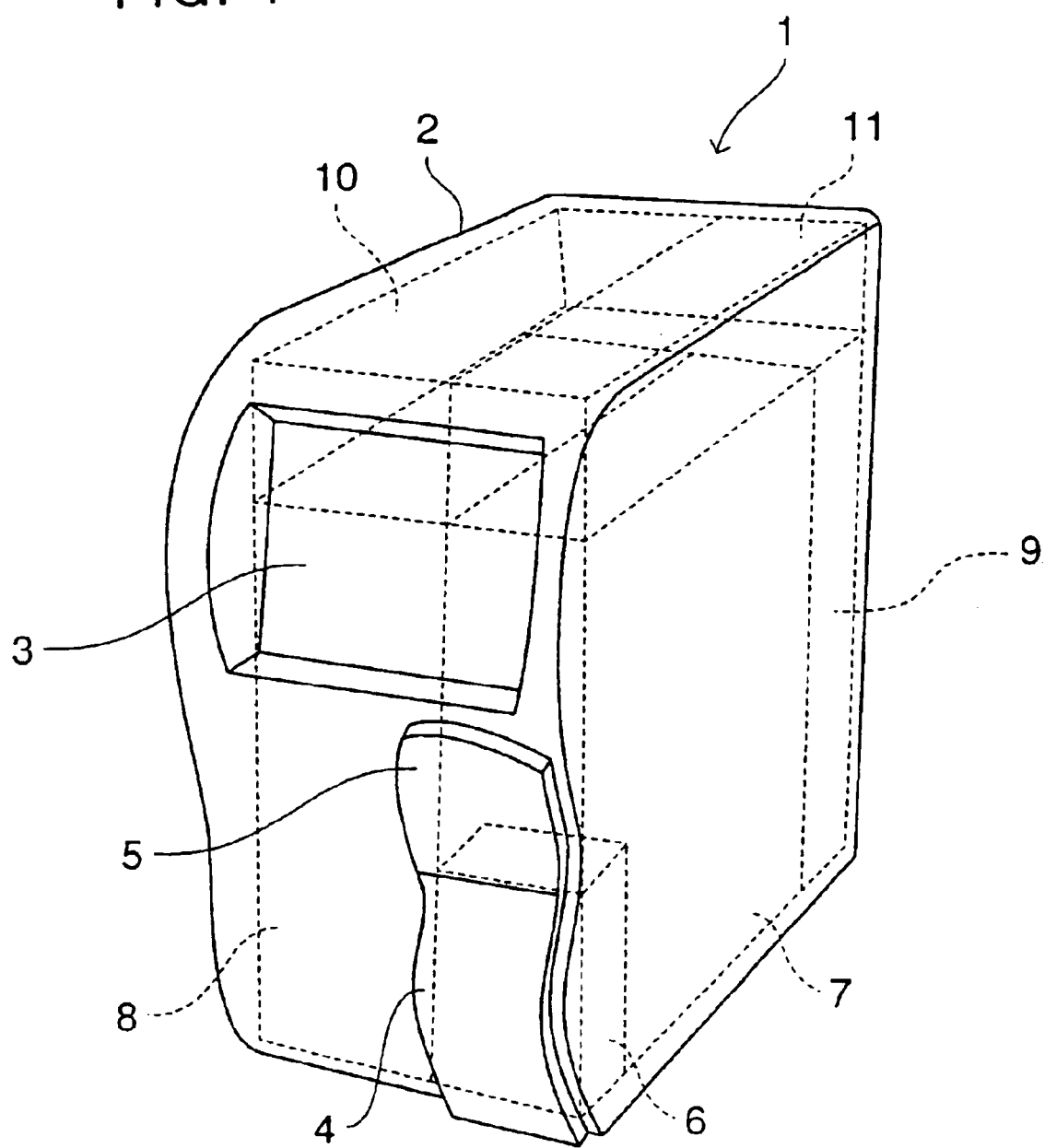
FIG. 1 is a front perspective view of a blood analyzer according to this invention.

The automatic sample analyzer according to this invention comprises: a pipette; a pipette driving device which moves the pipette to a sample vessel present in a predetermined position to cause the pipette to suck up a sample from the sample vessel, and then moves the pipette to an open vessel provided in another predetermined position to cause the pipette to discharge the sample into the open vessel; and an analyzing section for analyzing the discharged sample; the pipette driving device comprising a vertically movable main arm and an elongated guide arm cantilevered by the main arm and extending horizontally; the guide arm having a smaller flexural rigidity than the main arm; wherein the main arm vertically moves the pipette when the sample is to be sucked up from the sample vessel, and the guide arm guides the pipette to the open vessel and then vertically moves the pipette when the sample is to be discharged into the open vessel.

According to this invention, the pipette driving device achieves the vertical movement of the pipette with respect to the sample vessel by means of the main arm when the sample is to be sucked up, and achieves the vertical movement of the pipette with respect to the open vessel by means of the guide arm. This makes it possible to reduce the rigidities of the guide arm and associated components and the weight of the pipette driving device.

The pipette driving device may further comprise: a pipette holder for holding the pipette; a pipette horizontally driving section supporting the pipette holder in a vertically slidable manner for horizontally moving the pipette holder; and a pipette vertically driving section for vertically moving the main arm and the guide arm; wherein the pipette holder is fastened to the main arm in a horizontally disengageable manner; wherein the pipette holder is vertically moved by the main arm when being fastened to the main arm, and is vertically moved in engagement with the guide arm when being disengaged from the main arm.

The pipette holder may have a projection, and the main arm may have a recess to be horizontally brought into engagement with the projection.

The pipette holder may comprise a roller which is movable along the guide arm in engagement with the guide arm.

The pipette horizontally driving section may comprise a pipette vertically sliding section which supports the pipette holder in a vertically slidable manner.

The sample analyzer may further comprise a quantifying pump connected to the pipette for sucking the sample from the sample vessel after the pipette holder is lowered by the main arm, and discharging the sample after the pipette holder is moved apart from the main arm.

The sample vessel may be a capped sample vessel.

The pipette vertically driving section may comprise a stepping motor as a drive source, wherein a driving electric current to be supplied to the stepping motor for vertically moving the pipette holder is greater when the pipette holder is moved in engagement with the main arm than when the pipette holder is moved in engagement with the guide arm.

In accordance with another aspect of this invention, there is provided a pipette driving device, which comprises: a pipette holder for holding a pipette; a pipette horizontally driving section supporting the pipette holder in a vertically slidable manner for horizontally moving the pipette holder; a main arm to which the pipette holder is fastened in a horizontally disengageable manner; a guide arm horizontally extending from the main arm; and a pipette vertically driving section for vertically moving the main arm and the guide arm; wherein the pipette holder is vertically moved by the main arm when being fastened to the main arm, and vertically moved in engagement with the guide arm when being disengaged from the main arm.

In accordance with further another aspect of this invention, there is provided an automatic sample analyzer, which comprises: a pipette; a pipette driving device which moves the pipette to a sample vessel present in a predetermined position to cause the pipette to suck up a sample from the sample vessel, and then moves the pipette to an open vessel provided in another predetermined position to cause the pipette to discharge the sample into the open vessel; and an analyzing section for analyzing the discharged sample; the pipette driving device comprising a pipette vertically sliding section having a pipette holder for holding the pipette and a support member supporting the pipette holder in a vertically slidable manner, a pipette horizontally driving section to which the pipette vertically sliding section is attached in a replaceable manner, and a stopper member to be attached to the pipette vertically sliding section for prevention of vertical sliding of the pipette when the pipette vertically sliding section is replaced.

According to this invention, the movement of the pipette is prevented by the stopper member, so that the pipette vertically sliding section which holds the pipette can safely and easily be replaced.

The stopper member may be engaged with the pipette holder and the support member in a disengageable manner.

The pipette vertically sliding section may comprise a cleaning section for cleaning the pipette, wherein a tip of the pipette is accommodated in the cleaning section when the stopper member is attached to the pipette vertically sliding section.

In accordance with still another aspect of this invention, there is provided a pipette stopping device for a pipette driving device, which comprises: a pipette vertically sliding section having a pipette holder for holding a pipette and a support member supporting the pipette holder in a vertically slidable manner; a pipette horizontally driving section to which the pipette vertically sliding section is attached in a replaceable manner; and a stopper member to be attached to the pipette vertically sliding section for prevention of vertical sliding of the pipette when the pipette vertically sliding section is replaced.

In accordance with further another aspect of this invention, there is provided an automatic sample analyzer, which comprises: a housing having an opening and housing an analyzer body; a cover for opening and closing the opening; a sample rack vertically disposed inward of the opening for holding a sample vessel; a coupling member for tilting the sample rack toward the opening in association with the opening of the cover, and returning the sample rack in a vertical state in association with the closing of the cover; a resilient member for resiliently supporting the sample vessel set in the sample rack; and an analyzing section for sampling a sample from the sample vessel and analyzing the sample.

According to this invention, the sample rack is tilted toward the opening when the cover is opened, so that the sample vessel can easily be set in the sample rack. The sample vessel is supported from opposite sides thereof by the resilient member coaxially with the sample rack. Thus, sample vessels having different outer diameters can easily be set in the sample rack.

The sample rack may have an inner diameter greater than an outer diameter of the sample vessel for holding a lower portion of the sample vessel, and the resilient member may comprise first and second resilient members for resiliently holding a side face of the sample vessel from opposite sides to support the sample vessel coaxially with the sample rack.

The sample analyzer may further comprise a support member for moving the first resilient member apart from the second resilient member in association with the opening of the cover.

The support member may be supported pivotally about a shaft.

The sample rack may have a bottom supported pivotally about the shaft, and be pivotal in the same direction as the support member in association with the support member.

The sample analyzer may further comprise a biasing member for biasing the cover in a cover opening direction, and a button to be brought into engagement with the cover in a disengageable manner against a biasing force of the biasing member.

In accordance with still another aspect of this invention, there is provided a sample vessel setting device, which comprises: a sample rack having an inner diameter greater than an outer diameter of a sample vessel for holding a lower portion of the sample vessel; and first and second resilient members for resiliently holding a side face of the sample vessel from opposite sides to support the sample vessel coaxially with the sample rack.

In accordance with further another aspect of this invention, there is provided an automatic sample analyzer, which comprises: a housing having an opening and housing an analyzer body; a cover for opening and closing the opening; a sample rack vertically disposed inward of the opening for holding a sample vessel; a coupling member for tilting the sample rack toward the opening in association with the opening of the cover, and returning the sample rack in a vertical state in association with the closing of the cover; a pipette driving device which moves a pipette to the sample vessel present in a predetermined position to cause the pipette to suck up a sample from the sample vessel, and then moves the pipette to an open vessel provided in another predetermined position to cause the pipette to discharge the sample into the open vessel; a locking device for locking the cover when the pipette is inserted into the sample vessel from an upper side of the sample rack by the pipette driving device; and an analyzing section for analyzing the sample in the open vessel.

According to this invention, the locking device prevents the movement of the sample rack during a pipette inserting operation. Therefore, a sample sucking operation can stably be performed, and the pipette and the sample vessel are prevented from being damaged.

The pipette driving device may comprise a pipette vertically driving section for inserting the pipette into the sample vessel, and the locking device may comprise a lock rod extending parallel to the pipette vertically downward from a main arm and a projection piece projecting inward from the cover and having an engagement hole to which the lock rod is inserted when the pipette is inserted into the sample vessel.

In accordance with still another aspect of this invention, there is provided a sample rack locking device, which comprises: a sample rack movably supported for holding a sample vessel; and a lock member for mechanically preventing movement of the sample rack in association with a pipette inserting operation when a pipette is inserted into the sample vessel held by the sample rack.

In accordance with further another aspect of this invention, there is provided an automatic sample analyzer, which comprises: an analyzing section comprising a vessel for containing a sample, and a detector for analyzing constituents of the sample contained in the vessel; a waste liquid chamber for storing an analysis waste liquid including the sample, a reagent and a diluent; a negative pressure pump for applying a negative pressure to the waste liquid chamber to suck the analysis waste liquid out of at least one of the vessel and the detector; the negative pressure pump comprising an air pump having an air inlet and an air outlet, an enclosure cover which has first and second through-holes and covers the air pump, a suction tube extending from the outside of the enclosure cover to be connected to the air inlet through the first through-hole, and a silencing exhaust tube connected to the second through-hole and extending to the outside.

According to this invention, the negative pressure pump is enclosed in the cover and has the silencing exhaust tube thereby to be effectively silenced.

The analyzer may further comprise an elastic support base which supports the air pump.

The analyzer may further comprise a sensor for sensing the negative pressure applied to the waste liquid chamber, and a control section for controlling the negative pressure pump for regulating the negative pressure within a predetermined pressure range.

The predetermined pressure range may be 100 to 300 mmHg.

In accordance with still another aspect of this invention, there is provided a negative pressure pump, which comprises: an air pump having an air inlet and an air outlet; an enclosure cover having first and second through-holes and covering the air pump; a suction tube extending from the outside of the enclosure cover to be connected to the air inlet through the first through-hole; and a silencing exhaust tube connected to the second through-hole and extending to the outside.

In accordance with further another aspect of this invention, there is provided a sample analyzer, which comprises: a pipette; a liquid mixing vessel provided in a predetermined position; a sample supplying section for sucking a sample into the pipette and supplying the sample into the liquid mixing vessel; a diluent supplying section for supplying a diluent into the liquid mixing vessel; and a sample analyzing section for analyzing the sample diluted with the diluent; wherein the liquid mixing vessel is composed of a chemically resistant resin and has a roughened interior surface.

The sample supplying section may comprise a pipette driving device which moves the pipette to a sample vessel present in another predetermined position to cause the pipette to suck up the sample from the sample vessel, and then moves the pipette to the liquid mixing vessel to cause the pipette to discharge the sample into the liquid mixing vessel. Alternatively, the sample supplying section may comprise a negative pressure supplying section for applying a negative pressure to the liquid mixing vessel to suck up the sample into the liquid mixing vessel. In this case, the sample to be supplied into the liquid mixing vessel is preferably quantified by a quantifying device such as a sampling valve.

A vessel composed of the chemically resistant resin typically has a smooth interior surface and is highly repellent, i.e., has a lower wettability. When a sample retained in the bottom of the vessel is mixed with a diluent supplied into the vessel along the interior surface of the vessel, the diluent is liable to remain as water drops on the interior surface. Therefore, the amount of the diluent to be mixed with the sample is correspondingly reduced, resulting in inaccurate dilution. Accordingly, the accuracy of the sample analysis is reduced.

In general, the wettability of a resin surface relies on the chemical composition of the surface, the type and number of functional groups exposed to the surface, the acidic property or basic property of the surface, the crystallinity of the surface and the roughness of the surface.

This invention reveals that the wettability of the interior surface of the vessel is improved by roughening the interior surface. That is, the roughening of the interior surface of the vessel prevents the supplied diluent from remaining on the interior surface of the vessel when the sample is mixed with the diluent, whereby the sample is diluted at an improved dilution accuracy. Thus, the analysis accuracy can be improved.

In this invention, a relationship between the surface roughness and the wettability has been examined on the basis of an experiment, and it has been found that the wettability of the surface does not adversely influence the dilution accuracy if the surface has an arithmetic average surface roughness Ra of not smaller than 0.16 $\mu$m. It has also been found that an upper limit of the roughness Ra is preferably about 0.65 $\mu$m.

The roughening of the interior surface of the vessel is achieved, for example, in the following manner. A round rod having an outer diameter smaller than the inner diameter of the vessel is attached to a chuck of a ball mill, and sand paper lined with a sponge is wrapped around a distal side portion of the round rod so that the outer diameter of the resulting round rod becomes slightly greater than the inner diameter of the vessel.

While the round rod is rotated, the distal end of the round rod is gradually inserted into the vessel, whereby the interior surface of the vessel is roughened by the sand paper. Usable as the sand paper is #400 to #1500 sand paper. A buff with a sponge (Model 320 available from Sumitomo 3M Co., Ltd.) may be employed instead of the aforesaid sand paper.

The roughness Ra ($\mu$m) is herein defined as calculated from the following expression (see JIS B0601), wherein a portion of a roughness curve having a reference length m is cut out along an average line and expressed by y=f(x) with the average line taken as an X-axis and with a longitudinal magnification taken as a Y-axis:

$$R_a = \frac{1}{m}\int_0^L |f(x)|dx \qquad m: \text{Reference length}$$

The roughness curve is herein defined as a curve obtained by removing a surface undulation component having a wavelength greater than a predetermined level from a cross section curve by a phase compensation high band filter, and the cross section curve is herein defined as a contour of a cross section obtained by perpendicularly cutting a surface portion to be examined.

In the present invention, the liquid mixing vessel is produced by injection-molding a thermoplastic resin having a chemical resistance. Exemplary materials for the liquid mixing vessel include:
acryl-acrylonitrile-styrene resins;
acryl-acrylonitrile-styrene/polyamide alloys;
acryl-acrylonitrile-styrene/polycarbonate alloys;
acrylonitrile-butadiene-styrene resins;
acrylonitrile-butadiene-styrene/alloys;
acrylonitrile-butadiene-styrene/polyvinyl chloride alloys;
acrylonitrile-butadiene-styrene/polyamide alloys;
acrylonitrile-butadiene-styrene/polybutylene terephthalate alloys;

acrylonitrile-butadiene-styrene/methacrylate resin alloys;
acrylonitrile-butadiene-styrene/ polycarbonate alloys;
acrylonitrile-butadiene-styrene/maleimide-styrene resin alloys;
modified acrylonitrile-butadiene-styrene resins;
acrylonitrile-chlorinated polyethylene-styrene resins;
acrylonitrile-ethylene propylene rubber-styrene resins;
acrylonitrile resins;
acrylonitrile-styrene resins;
chlorinated polyethylenes;
ethylene-vinyl alcohol resins;
crystalline polymers;
styrene-butadiene resins;
styrene-maleic acid resins;
biodegradable resins (based on cellulose acetate);
biodegradable resins (based on high molecular weight thermoplastic polycaprolactone);
polytrifluoroethylenes;
tetrafluoroethylene/ethylene resins;
tetrafluoroethylene/hexafluoropropylene resins;
amorphous fluorinated resins;
tetrafluoroethylene/perfluoroalcoxyethylene resins;
polytetrafluoroethylenes;
polyfluorovinylidenes;
modified polytetrafluoroethylenes;
tetrafluoroethylene-hexafluoropropylene/fluorovinylidene alloys;
tetrafluoroethylene/polypropylene alloys;
polyamide 11;
polyamide 12;
polyamide 40;
polyamide-acrylonitrile-butadiene-styrene alloys;
polyamide-maleimide-styrene resin alloys;
polyamide-polypropylene alloys
polyamide 6;
polyamide 6/amorphous polyolefin alloys;
polyamide 6/special rubber alloys;
polyamide 6.66;
polyamide 610;
polyamide 66;
modified polyamide 66;
polyamide 66/thermoplastic elastomer alloys;
polyamide 6T;
amorphous polyamide;
polyamide MXD6;
polyallylether ketons;
polyamide imides;
polyallylates;
polyarylsulfones;
thermoplastic polyimides;
polycyclohexanedimethylene terephthalates;
high density polyethylenes;
low density polyethylenes;
very high molecular weight polyethylenes;
polyetherether ketones;
polyether imides;
polyethylene naphthalates;
polyether nitrites;
polyether sulfones;
polyethylene terephthalates;
polyvinyl chlorides;
modified polyvinyl chlorides;
polyvinyl chloride/acrylonitrile-butadiene alloys;
polybenzimidazoles;
polybutylene terephthalates;
polybutylene terephthalate-acrylonitrile-butadiene-styrene alloys;
polymethylmethacrylimides;
polymethylpentenes;
polycarbonates;
polycarbonate-acrylonitrile-butadiene-styrene alloys;
polycarbonate-polyimide alloys;
polycarbonate-polyethylene terephthalate alloys;
amorphous polyolefins;
polyacetals;
polypropylenes;
polypropylene-polyamide alloys;
polyphthalamides;
polysulfones;
modified polyphenylene ethers;
modified polyphenylene ether/polyamide alloys;
modified polyphenylene ether/polybutylene terephthalate alloys;
modified polyphenylene ether/polyphenylene sulfide alloys;
modified polyphenylene ether/special rubber alloys;
polyphenylene sulfides;
polyphenylene sulfide/polyamide 66 alloys;
general-purpose polystyrenes;
high impact resistance polystyrenes;
intermediate impact resistance polystyrenes;
modified polystyrenes;
syndiotactic polystyrenes;
polythioether sulfones;
maleimide-styrene resins;
maleimide-styrene/polyamide alloys;
methacryl-styrene resins;
methacryl resins; and
modified methacryl resins.

In accordance with still another aspect of this invention, there is provided a liquid mixing vessel comprising a cylindrical interior surface, an interior bottom, and a liquid supply port provided in the vicinity of an upper end thereof for supplying a liquid to the bottom along the interior surface, the liquid mixing vessel being composed of a chemically resistant resin with the interior surface thereof roughened.

The vessel may have an open top, and may be produced by injection-molding the chemically resistant resin.

The interior surface of the vessel preferably has an arithmetic average surface roughness Ra of not smaller than 0.16 $\mu$m.

It is further preferred that the interior surface of the vessel has an arithmetic average surface roughness Ra of 0.16 $\mu$m$\leq$Ra$\leq$0.65 $\mu$m.

The chemically resistant resin may be a polyether imide.

The vessel may further comprise a liquid drain port provided at the bottom thereof for draining the liquid, and further comprise an air supply port provided at the bottom thereof for injecting a gas.

In accordance with further another aspect of this invention, there is provided an automatic sample analyzer, which comprises: a liquid suction tube; a quantifying section for sucking a sample through the liquid suction tube and quantifying the sample; and an analyzing section for analyzing the quantified sample; the liquid suction tube comprising an elongated pipe, which has a liquid flow path (i.e., a suction path) extending therein parallel to an axis thereof, and a groove provided in an outer surface thereof as extending longitudinally thereof.

According to this invention, when a cap of a capped vacuum blood sampling tube (sample vessel) is pieced with the liquid suction tube (pipette), the inside of the blood sampling tube immediately communicates with the atmosphere through the groove by a minimum distance.

Therefore, the sample can smoothly be sucked and quantified through the liquid suction tube, so that the analysis of the sample can be performed accurately. In addition, the liquid suction tube has a simplified construction with the groove longitudinally formed in the outer surface of the pipe. Therefore, the groove and the exterior of the liquid suction tube can simultaneously be cleaned.

In this invention, the groove preferably extends parallel to the axis of the pipe. Thus, the formation of the groove can easily be achieved.

The groove preferably has a cross section increasing toward the outer surface of the pipe. Thus, the groove is prevented from being clogged with rubber scum of the cap and the sample.

Further, the groove preferably has a cross section having a round bottom. Thus, the groove is prevented from being clogged with rubber scum of the cap and the sample.

The liquid flow path (suction path) is preferably offset from the axis of the pipe. Thus, the groove can be formed in a greater cross section. Therefore, the cross sectional area, configuration and position of the groove can more flexibly be determined, so that the ventilating efficiency and the cleaning efficiency can be improved.

In accordance with still another aspect of this invention, there is provided a liquid suction tube comprising an elongated pipe, which has a liquid flow path extending therein parallel to an axis thereof and a groove provided in an outer surface thereof as extending longitudinally thereof.

In the liquid suction tube, the groove may extend parallel to the axis of the pipe.

The groove may have a cross section increasing toward the outer surface of the pipe.

The groove may have a cross section having a round bottom.

The liquid flow path may be offset from the axis of the pipe.

In accordance with further another aspect of this invention, there is provided an automatic sample analyzer, which comprises: a pipette; an analyzing section for analyzing a sample sucked from the pipette; a pipette cleaning device having a cleaner body having a pipette through-path through which the pipette is inserted from an inlet to an outlet thereof; and a driving device for moving at least one of the pipette and the cleaner body; wherein the pipette through-path provided in the cleaner body includes a pipette guide hole formed in an inlet portion thereof coaxially therewith and a pipette cleaning hole formed in an outlet portion thereof coaxially therewith; wherein the pipette cleaning hole has first, second and third openings formed in an interior surface thereof in this order from the inlet to the outlet; wherein the cleaner body comprises a vent path for communication between the first opening and the atmosphere, a cleaning liquid supply path communicating with the third opening, and a cleaning liquid drain path communicating with the second opening.

According to this invention, the opening communicating with the atmosphere is formed in the interior surface of the pipette through-path of the pipette cleaning device, so that a cleaning liquid is less liable to remain in the pipette cleaning device for efficient cleaning of the pipette. Thus, the analysis of the sample can be performed accurately.

The analyzer may further comprise: a supplying section for supplying the cleaning liquid into the cleaning liquid supply path; a sucking section for sucking the cleaning liquid from the cleaning liquid drain path; and a driver circuit section for driving the supplying section and the sucking section; wherein the driving device comprises a vertically driving section for vertically moving at least one of the pipette and the cleaner body; wherein the driver circuit section drives the supplying section and the sucking section for cleaning the exterior of the pipette when the pipette is moved up or the cleaner body is moved down.

Alternatively, the analyzer may further comprise: a supplying section for supplying the cleaning liquid into the pipette; a sucking section for sucking the cleaning liquid from the cleaning liquid drain path; and a driver circuit section for driving the supplying section and the sucking section; wherein the driving device comprises a vertically driving section for vertically moving at least one of the pipette and the cleaner body; wherein the driver circuit section drives the supplying section and the sucking section for cleaning the interior of the pipette when a tip of the pipette is present in the pipette through-path.

In accordance with still another aspect of this invention, there is provided a pipette cleaning device, which comprises: a cleaner body having a pipette through-path through which a pipette is inserted from an inlet to an outlet thereof; the pipette through-path comprising a pipette guide hole formed in an inlet portion thereof coaxially therewith and a pipette cleaning hole formed in an outlet portion thereof coaxially therewith; the pipette cleaning hole having first, second and third openings formed in an interior surface thereof in this order from the inlet to the outlet; the cleaner body comprising a vent path for communication between the first opening and the atmosphere, a cleaning liquid supply path communicating with the third opening, and a cleaning liquid drain path communicating with the second opening.

The pipette through-path may have a round cross section, and the pipette cleaning hole may include first and second through-holes serially connected in this order from the inlet to the outlet, wherein the first and second openings are formed in the interior surface of the first through-hole, and the third opening is formed in the interior surface of the second through-hole, wherein the inner diameter of the pipette through-path increases in the order of the pipette guide hole, the first through-hole and the second through-hole.

Alternatively, the pipette through-path may have a round cross section, and the pipette cleaning hole may include first, second and third through-holes serially connected in this order from the inlet to the outlet, wherein the first and second openings are formed in the interior surface of the first through-hole, and the third opening is formed in the interior surface of the third through-hole, wherein the pipette guide hole and the second through-hole have smaller inner diameters than the first through-hole and the third through-hole.

In accordance with further another aspect of this invention, there is provided an automatic sample analyzer, which comprises: a pipette having a suction port provided at a tip thereof; a quantifying section for sucking and quantifying a sample through the pipette; a supplying section for supplying a liquid into the pipette; an analyzing section for analyzing the quantified sample; and a control section for controlling the quantifying section and the supplying section; wherein the control section controls the supplying section to fill the suction port of the pipette with the liquid before the suction of the sample.

According to this invention, the suction port of the pipette is filled with the liquid before the suction of the sample. Therefore, the sample is prevented from entering the suction port when the pipette is inserted into the sample before the suction. This improves the quantifying accuracy.

The analyzer may further comprise a cleaner for cleaning the pipette, wherein the suction port is provided in a side wall of the pipette in the vicinity of a tip of the pipette, wherein the cleaner comprises a through-path through which the pipette is inserted, a cleaning liquid supply path communicating with the through-path for supplying a cleaning liquid, and a cleaning liquid drain path communicating with the through-path for draining the cleaning liquid; wherein the cleaner is positioned so that an angle defined between an axis of the suction port of the pipette and an axis of an inlet of the cleaning liquid drain path is greater than 90 degrees as viewed axially of the pipette.

With this arrangement, the suction port is not influenced by a negative pressure applied from the cleaning liquid drain path when the pipette is cleaned in the cleaner before the suction of the sample through the pipette. Therefore, the liquid filled in the suction port of the pipette is not sucked out into the cleaning liquid drain path. Thus, the suction port is kept filled with the liquid, so that the sample can accurately be quantified.

In accordance with still another aspect of this invention, there is provided a liquid suction device, which comprises: a pipette having a suction port provided in a side wall thereof in the vicinity of a tip thereof; a sucking section for sucking a liquid through the pipette; and a cleaner for cleaning the pipette; wherein the cleaner comprises a through-path through which the pipette is inserted, a cleaning liquid supply path communicating with the through-path for supplying a cleaning liquid, and a cleaning liquid drain path communicating with the through-path for draining the cleaning liquid; wherein the cleaner is positioned so that an angle defined between an axis of the suction port of the pipette and an axis of an inlet of the cleaning liquid drain path is greater than 90 degrees as viewed axially of the pipette.

The liquid suction device preferably further comprises a liquid supplying section for supplying the liquid into the pipette, wherein the liquid supplying section fills the suction port of the pipette with the liquid before the suction of the sample through the pipette.

In accordance with further another aspect of this invention, there is provided a pipette cleaning device, which comprises a cleaner for cleaning a pipette having a suction port provided in a side wall thereof in the vicinity of a tip thereof, wherein the cleaner comprises a through-path through which the pipette is inserted, a cleaning liquid supply path communicating with the through-path for supplying a cleaning liquid, and a cleaning liquid drain path communicating with the through-path for draining the cleaning liquid, wherein the cleaner is positioned so that an angle defined between an axis of the suction port of the pipette and an axis of an inlet of the cleaning liquid drain path is greater than 90 degrees as viewed axially of the pipette.

In accordance with still another aspect of this invention, there is provided a liquid suction device, which comprises: a pipette having a suction port provided in a tip portion thereof; a sucking section for sucking a first liquid through the pipette; a supplying section for supplying a second liquid to the pipette; and a control section for controlling the sucking section and the supplying section; wherein the control section controls the supplying section to fill the suction port of the pipette with the second liquid before the suction of the first liquid.

The liquid suction device may further comprise a cleaner for cleaning the pipette, wherein the suction port is provided in a side wall of the pipette in the vicinity of a tip of the pipette, wherein the cleaner comprises a through-path through which the pipette is inserted, a cleaning liquid supply path communicating with the through-path for supplying a cleaning liquid, and a cleaning liquid drain path communicating with the through-path for draining the cleaning liquid, wherein the cleaner is positioned so that an angle defined between an axis of the suction port of the pipette and an axis of an inlet of the cleaning liquid drain path is greater than 90 degrees as viewed axially of the pipette.

In accordance with further another aspect of this invention, there is provided an automatic sample analyzer operable in a plurality of analysis modes, the automatic sample analyzer comprising: an analysis mode selection button for selecting one of the analysis modes; a start button for outputting a command for starting an analytic operation in the selected analysis mode; a color changing section for changing a color of the start button; a color change controlling section for controlling the color changing section for changing the color of the start button according to the selected analysis mode; and an analyzing section for analyzing a sample upon reception of the command from the start button.

According to this invention, the color of the start button is changed according to the analysis mode selected by a user. Thus, the user can confirm the analysis mode on the basis of the color of the button when pressing the start button to start the analysis. Therefore, an erroneous operation attributable to a mistake in mode selection can be suppressed.

The analyzer may further comprise a touch panel input/display section, wherein the analysis mode selection button and the start button are displayed on the input/display section, wherein the color changing section changes the color of the start button displayed on the input/display section.

In accordance with still another aspect of this invention, there is provided an automatic sample analyzer, which comprises: an input section; a display section; an analyzing section; and a control section for controlling the display section and the analyzing section upon reception of an output from the input section; wherein the display section selectively displays a main screen which indicates a state where the analyzing section is ready to start an analysis and an analysis screen in which results of the analysis performed by the analyzing section are displayed; wherein the control section switches the analysis screen displayed by the display section to the main screen if no input operation is performed on the input section during a period from the start of the display of the analysis results in the analysis screen to the completion of a predetermined operation performed by the analyzing section.

According to this invention, the analysis screen is automatically switched to the main screen if no input operation is performed before the completion of the predetermined operation in the analyzer. This obviates the need for the user to manually switch the screen.

In accordance with further another aspect of this invention, there is provided an automatic sample analyzer, which comprises: a touch panel input/display section; a start button displayed on the input/display section; an analyzing section for actuating an analyzing device upon reception of a command from the displayed start button; a monitoring section for monitoring the analyzing device; and a control section for controlling a displaying operation of the input/display section; wherein the control section erases the start button on the input/display section when the monitoring section detects an abnormality.

In accordance with still another aspect of this invention, there is provided an automatic sample analyzer, which comprises: an analyzing section for analyzing a sample; a display section for displaying results of the analysis in an analysis screen; and a control section for controlling the display section and the analyzing section; wherein the display section selectively displays a first analysis screen in which results of analysis of one or more analysis items are displayed in a first font size and a second analysis screen in which results of analysis of a greater number of analysis items than those in the first analysis screen are displayed in a second font size smaller than the first font size.

The analyzer may further comprise an input section for optionally inputting an analysis item to be displayed in the first analysis screen.

In accordance with further another aspect of this invention, there is provided an automatic sample analyzer, which comprises: an orifice through which a sample passes; a DC power supply; a constant electric current circuit for supplying a constant electric current to the sample passing through the orifice from the DC power supply; a resistance-type detecting section for detecting a change in impedance of the sample passing through the orifice; and an analyzing section for analyzing the sample on the basis of the detected impedance change; wherein the DC power supply comprises a Cockcroft power supply.

The Cockcroft power supply may comprise an oscillator section, a switching circuit section for intermittently outputting a DC input voltage in synchronization with a switching frequency of the oscillator section, and a booster section for boosting the voltage outputted from the switching circuit section, wherein the switching frequency is 50 to 1000 kHz.

The DC power supply may spontaneously be cooled.

In accordance with still another aspect of this invention, there is provided an automatic sample analyzer, which comprises: an analyzing section; a housing which houses the analyzing section; a container housing unit which houses containers for containing liquids to be supplied and drained into/from the analyzing section; a container holder attached to the outside of the housing for holding the container housing unit; wherein the container housing unit comprises two large containers, one small container and a case for housing the large and small containers; wherein the large containers each have a container body for containing a fluid, a mouth portion through which the fluid is taken into and out of the container body, a shoulder portion extending downward from the mouth portion, a small container mounting portion provided on the shoulder portion for receiving the small container, and a container side wall extending downward from the shoulder portion; wherein the small container has a container body for containing a fluid, a mouth portion through which the fluid is taken into and out of the container body, a shoulder portion extending downward from the mouth portion, a container side wall extending downward from the shoulder portion, and a bottom face configured in conformity with the small container mounting portion; wherein the two large containers are combined together and fitted in the case so that the container side walls extending downward from the small container mounting portions of the two large containers are in contact with each other, and the small container is rested on the small container mounting portions provided on the shoulder portions above the container side walls of the two large containers in contact with each other.

In accordance with further another aspect of this invention, there is provided a container housing unit, which comprises: two large containers; one small container; and a case for housing the large and small containers; wherein the large containers each have a container body for containing a fluid, a mouth portion through which the fluid is taken into and out of the container body, a shoulder portion extending downward from the mouth portion, a small container mounting portion provided on the shoulder portion for receiving the small container, and a container side wall extending downward from the shoulder portion; wherein the small container has a container body for containing a fluid, a mouth portion through which the fluid is taken into and out of the container body, a shoulder portion extending downward from the mouth portion, a container side wall extending downward from the shoulder portion, and a bottom face configured in conformity with the small container mounting portion; wherein the two large containers are combined together and fitted in the case so that the container side walls extending downward from the small container mounting portions of the two large containers are in contact with each other, and the small container is rested on the small container mounting portions provided on the shoulder portions above the container side walls of the two large containers in contact with each other.

The shoulder portions of the two large containers may respectively have fixture portions for fixing the smaller container.

The fixture portions may comprise step portions respectively provided on the shoulder portions of the two large containers, so that the small container is fixed with the container side wall thereof held by the step portions of the two large containers.

The two large containers may respectively have projections or recesses formed in the step portions thereof, and the small container may have recesses or projections formed in the container side wall to be engaged with the projections or the recesses formed in the step portions of the large containers.

Alternatively, the two large containers may respectively have projections formed in the step portions thereof, and the small container may have recesses formed in the container side wall to be engaged with the projections formed in the step portions of the large containers. The two large containers may respectively further have flanges provided on upper portions of the projections thereof to be partly overlapped with the small container.

The two large containers may have the same configuration and the same volume. One of the large containers may contain a diluent, and the other large container may store a waste liquid.

The small container may contain a hemolyzing agent.

In accordance with still another aspect of this invention, there is provided a container mounting method for mounting two large containers and one small container in place, the large containers each having a container body for containing a fluid, a mouth portion through which the fluid is taken into and out of the container body, a shoulder portion extending downward from the mouth portion, a small container mounting portion provided on the shoulder portion for receiving the small container, and a container side wall extending downward from the shoulder portion, the small container having a container body for containing a fluid, a mouth portion through which the fluid is taken into and out of the container body, and a bottom face configured in conformity with the small container mounting portion, the method comprising the steps of: combining the two large containers with the container side walls thereof in contact with each other; and resting the small container on the small container mounting portions provided on the shoulder portions above the container side walls of the two large containers in contact with each other.

In accordance with further another aspect of this invention, there is provided a container, which comprises a container body for containing a fluid; a mouth portion through which the fluid is taken into and out of the container; a shoulder portion extending downward from the mouth portion; a container side wall extending downward from the shoulder portion; and a fixture portion provided on the shoulder portion for fixing another container.

The fixture portion may comprise a step portion provided on the shoulder portion, and a projection or a recess formed in the step portion.

Alternatively, the step portion may have a projection, and a flange provided on an upper portion of the projection.

In accordance with still another aspect of this invention, there is provided a small container, which comprises recesses or projections formed in container side wall thereof to be engaged with projections or recesses respectively provided on step portions of shoulder portions of large containers.

In accordance with further another aspect of this invention, there is provided an automatic sample analyzer, which comprises: an analyzing section; a housing which houses the analyzing section and has a supply/drain port for supplying or draining a liquid into/out of the analyzing section; a container attached to the outside of the housing for storing the liquid to be supplied or drained into/out of the analyzing section; and a flow path connection mechanism for connecting a mouth portion of the container to the supply/drain port; wherein the flow path connection mechanism comprises a guide mechanism pivotal about a support shaft, and a nozzle attached to the guide mechanism; wherein the nozzle has a flow path therein, one end of the flow path being connectable to the mouth portion of the container, the other end of the flow path being connectable to the supply/drain port of the housing; wherein the guide mechanism is pivoted about the support shaft to guide the nozzle into the mouth portion of the container.

In accordance with still another aspect of this invention, there is provided a flow path connection mechanism for connecting a mouth portion of a container to a supply/drain port of a sample analyzer, the flow path connection mechanism comprising: a guide mechanism pivotal about a support shaft; and a nozzle attached to the guide mechanism; wherein the nozzle has a flow path therein, one end of the flow path being connectable to the mouth potion of the container, the other end of the flow path being connectable to the supply/drain port of the analyzer; wherein the guide mechanism is pivoted about the support shaft to guide the nozzle into the mouth portion of the container.

The support shaft may be attached to a wall of the analyzer.

The guide mechanism may comprise a first lever, a second lever and a biasing member, wherein the first lever is pivotal at one end thereof about the support shaft, wherein the second lever is pivotal about a second support shaft provided at the other end of the first lever, wherein the biasing member is provided between the first lever and the wall of the analyzer for biasing the first lever apart from the mouth portion of the container, wherein the nozzle is attached to the second lever.

The guide mechanism may further comprise a third lever supported about the support shaft, wherein the third lever is brought into abutment against an inner cap provided on the mouth portion of the container by pivoting the first lever toward the mouth portion of the container.

In accordance with further another aspect of this invention, there is provided a container holder, which comprises a support shaft; a guide mechanism pivotal about the support shaft; and a nozzle attached to the guide mechanism; wherein the nozzle has a flow path therein, one end of the flow path being connectable to a mouth potion of a container, the other end of the flow path being connectable to a supply/drain port of an analyzer; wherein the guide mechanism is pivoted about the support shaft to guide the nozzle into the mouth portion of the container.

In accordance with still another aspect of this invention, there is provided a container which is a first container used with second and third containers, which comprises a first body for containing liquid therein, first neck and shoulder portions formed on a upper portion of the first body, the first neck portion having a mouth communicating inside the first body, and a first projection projecting from the first neck portion to the first shoulder portion, wherein the second container is formed in the same configuration as the first container and includes a second body, second neck and shoulder portions and a second projection which correspond to the first container, the third container includes a third body for containing liquid therein, the third body having two opposite recesses formed on an outside thereof, and a mouth portion and a third shoulder portion which are formed on an upper portion of the third body, the mouth portion having a mouth communicating inside the third body, and the first container cooperates with the second container to hold the third container on the first and second shoulder portions and fix the third container by engaging the first and second projections to the opposite recesses and the third shoulder portion.

The first projection may include upper and lower portions so that the lower portion is fitted into one of the two opposite recesses and the upper portion overlies the third shoulder.

The container may further comprise an inner cap fitted in the mouth of the first container and an inner suction tube, wherein the inner cap has a first through hole for communicating with the tube and a second through hole for releasing air from the first body, the tube being connected with the first through hole and extending to an inner bottom of the first body.

The first body may have a substantially rectangular shape.

The third body may have a substantially flat bottom.

In accordance with still another aspect of this invention, there is provided a container which is a third container used with first and second containers, which comprising: a third body for containing liquid therein, the third body having two opposite recesses formed on an outside thereof, and a mouth portion and a third shoulder portion which are formed on an upper portion of the third body, the mouth portion having a mouth communicating inside the third body wherein the first container includes a first body for containing liquid therein, first neck and shoulder portions on a upper portion of the first body, the first neck portion having a mouth communicating inside the first body, and a first projection projecting from the first neck portion to the first shoulder portion, the second container is formed in the same configuration as the first container and includes a second body, second neck and shoulder portions and a second projection which correspond to the first container, and the first container cooperates with the second container to hold the third container on the first and second shoulder portions and fix the third container by engaging the first and second projections to the opposite recesses and the third shoulder portion.

The container may further comprise an inner cap fitted in the mouth of the third container and an inner suction tube, wherein the inner cap has a first through hole for communicating with the tube and a second through hole for releasing air from the third body, the tube being connected with the first through hole and extending to a inner bottom of the third body.

In accordance with still another aspect of this invention, there is provided a flow path connection mechanism which comprises: a lever pivotally mounted on a supporting member; and a nozzle pivotally mounted on the lever, the nozzle having proximal and distal ends, wherein the proximal end is connected with an outer suction tube and the distal end is connected with a mouth of a container when the lever pivots.

The lever may include first, second and third levers, the first and third lever being pivotally mounted on the supporting member, the second lever and the nozzle being pivotally mounted on the first lever, wherein when the first, second and third levers pivot in the same direction, the first lever leads the distal end of the nozzle to enter the mouth of the container and the second and third levers engage the container so that the nozzle keeps a connection with the mouth.

The flow path connection mechanism may further comprise a bias member for biasing the lever so that the lever leaves the mouth.

The automatic sample analyzers according to this invention are employed for analyzing a body fluid (blood, urine, marrow fluid or the like) of a mammal such as a human.

An automatic blood analyzer according to one embodiment of this invention will hereinafter be described.

The "automatic" blood analyzer herein means a blood analyzer which permits a user to set at least one sample vessel in the analyzer, and is capable of automatically detecting constituents of a blood sample contained in the sample vessel, calculating values of analysis items, and outputting the results of the calculation.

The automatic blood analyzer is adapted to analyze a blood sample of a mammal such as a human.

Where the blood sample is a human blood sample, exemplary analysis items (measurement/analysis items) include the number of red blood cells (RBC), the number of white blood cells (WBC), the amount of hemoglobin (HGB), the value of hematocrit (HCT), the number of platelets (PLT), a mean corpuscular volume (MCV), a mean corpuscular hemoglobin (MCH), and a mean corpuscular hemoglobin concentration (MCHC).

As for measurement principles, it is preferred to employ a sheath flow electrical resistance method for the measurement of the RBC and the PLT, an electrical resistance method for the measurement of the WBC, and a calorimetric method for the measurement of the HGB. The blood sample to be analyzed is obtained by sampling blood from a subject into a sample vessel (blood sampling tube). The blood sample may be a whole blood sample or a sample preliminarily diluted to a predetermined concentration.

Particularly, where blood is sampled from an infant, the amount of the blood sample is small, so that the blood sample is preliminarily diluted to a predetermined concentration (e.g., 26 times).

Usable as the sample vessel (blood sampling tube) in the automatic blood analyzer are common vacuum blood sampling tubes (sealed with a rubber cap) and common open blood sampling tubes (having an open mouth) each having an outer diameter of 12 to 15 mm and a length of not greater than 85 mm, and small-volume blood sampling tubes each having an outer diameter of 9 to 11 mm.

The amount of the blood sample required for the analysis is, for example, 10 to 15 $\mu$L in the case of the whole blood sample, and 250 to 350 $\mu$L in the case of the pre-diluted blood sample.

The automatic blood analyzer comprises a main body and a container housing unit. Preferably, the main body is housed in a housing, and the container housing unit is removably attached to a side wall of the housing. The main body includes a display section provided on a front upper portion of the housing. The display section includes an LCD (liquid crystal display panel) for displaying the results of the analysis. If a touch panel for inputting analysis conditions is provided integrally with the LCD, improvement in the operability of the analyzer as well as space saving can be achieved.

Disposed in the housing are: a sample setting section in which the user sets the sample vessel; a detecting section in which the sample is quantitatively dispensed from the sample vessel and diluted and the blood constituents of the sample are detected; a fluid controlling section including fluid controlling devices for controlling fluids required for quantitatively dispensing and diluting the sample in the detecting section; an electrical control board section which houses electric components for electrically controlling the detecting section, the fluid controlling section and the display section; a power supply section for transforming an AC voltage inputted from a commercial power supply into a lower-level DC voltage; and a printer section for printing out the results of the analysis.

It is preferred to properly lay out these sections in consideration of ease of operation and maintenance and heat generation.

Where the sample setting section is disposed in the vicinity of a front face of the housing and an opening/closing cover (sample setting panel) is provided on the front face of the housing, for example, the user can easily access the sample setting section to set the sample vessel in the sample setting section by opening the cover. Further, the sample vessel thus set is advantageously protected by the cover.

Where the detecting section is provided as a unit inward of a right or left side wall of the housing, for example, the detecting section can easily be accessed for maintenance and inspection by removing one side plate of the housing. The detecting section preferably include a pipette driving device, a mixing chamber, and a detector for quantitatively dispensing the blood sample from the sample vessel by means of a pipette, properly diluting the blood sample and properly analyzing the blood constituents.

The pipette to be herein employed is a pipette generally referred to as "piercer" or "needle" having a sharp tip for piercing the cap of the sample vessel.

Where the fluid controlling section is disposed inward of the other side wall opposite to the detecting section or in back-to-back relation with respect to the detecting section, the fluid controlling section can easily be accessed for maintenance and inspection by removing the other side plate of the housing.

Since electromagnetic valves and pumps provided in the fluid controlling section may cause noises, consideration is given to the silencing of these components for reducing the noises (including sudden noises) of the entire fluid controlling section, for example, to a level not greater than 45 dB. Particularly, a pressure device such as an external compressor is not employed as a driving source for a fluid circuit but, instead, a negative pressure pump is provided in the housing for easy handling of the blood analyzer. The negative pressure pump, which serves as a negative pressure source, is frequently actuated in the blood analyzer, requiring special consideration for the silencing thereof.

The power supply section includes components such as transistors and diodes which generate heat. Therefore, the power supply section is disposed in the uppermost portion of the housing, and ventilators (vent holes) are provided in the housing for spontaneous cooling of the power supply. This arrangement obviates the need for provision of a fan for forcible cooling, and ensures silencing and space saving. With the power supply section disposed in the uppermost portion, the other components are prevented from being adversely affected by the heat generated by the power supply section.

The container housing unit is preferably adapted to house at least two containers for containing a diluent and a hemolyzing agent to be used in the analyzer body, and a container for storing a waste liquid to be drained from the analyzer body.

With reference to the attached drawings, this invention will hereinafter be described in detail by way of another embodiment thereof. However, it should be understood that the invention be not limited thereto.

Figure 2:
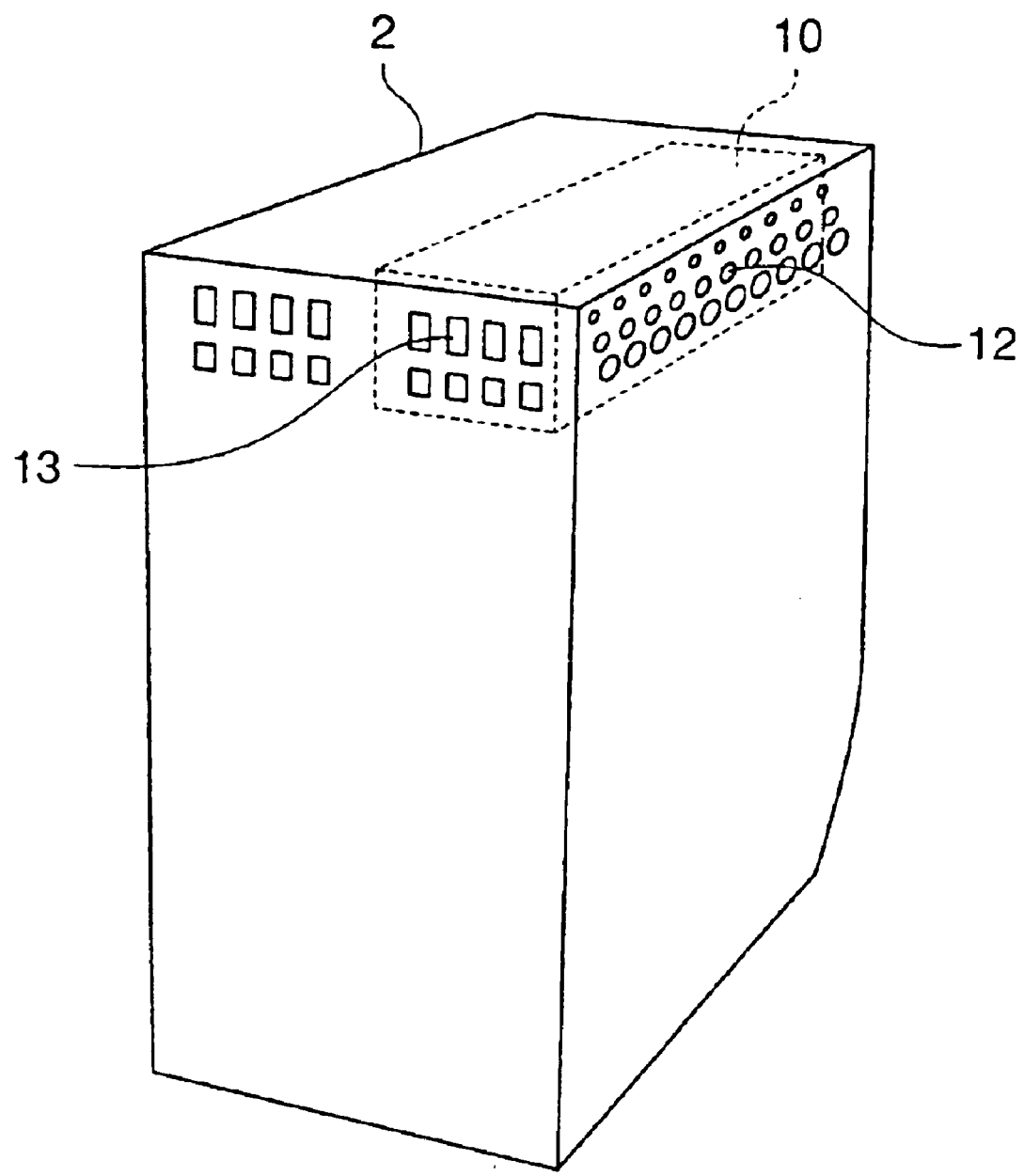
FIG. 2 is a rear perspective view of the blood analyzer according to this invention.

FIGS. 1 and 2 are a front perspective view and a rear perspective view, respectively, of a blood analyzer according to the embodiment of the invention.

As shown, an analyzer body 1 is housed in a housing 2, and includes an input/display section 3 provided on a front upper portion of the housing 2, a sample setting panel 4 provided on a lower front right portion of the housing 2 and to be opened and closed when a sample vessel is set, and a button 5 to be pressed for opening the sample setting panel 4.

A sample setting section 6 for receiving the sample vessel, and a detecting section 7 for quantitatively dispensing a sample from the sample vessel, diluting the sample and analyzing constituents of the sample are provided inward of a right side plate of the housing 2.

A fluid controlling section 8 which collectively accommodates fluid devices such as valves and pumps for controlling fluids for the quantitatively dispensing and dilution of the sample in the detecting section 7 is provided inward of a left side plate of the housing 2. An electrical control board section 9 which accommodates a board mounted with electrical control devices for electrically controlling the detecting section 7, the fluid controlling section 8 and the display section 3 is provided inward of a rear side plate of the housing 2.

A power supply section 10 for transforming a commercially available AC voltage supplied thereto into a DC voltage, and a printer section 11 for printing out the results of the analysis are provided inward of a ceiling plate of the housing 2.

The right and left side plates, the rear side plate and the ceiling plate are removably fastened by screws, so that the respective sections are easily accessed for maintenance.

The power supply section 10 which includes a heat generating component is provided in the uppermost position within the housing 2, and ventilators (vent holes) 12, 13 are provided as surrounding the power supply section 10 in the housing 2 as shown in FIG. 2. Therefore, air heated by the power supply section 10 is vented through the ventilators 12, 13 for spontaneous air cooling without thermally affecting the other components of the analyzer. That is, the power supply section 10 does not require forcible air cooling means such as a cooling fan, so that the size reduction and noise reduction of the analyzer can be achieved.

Figure 3:
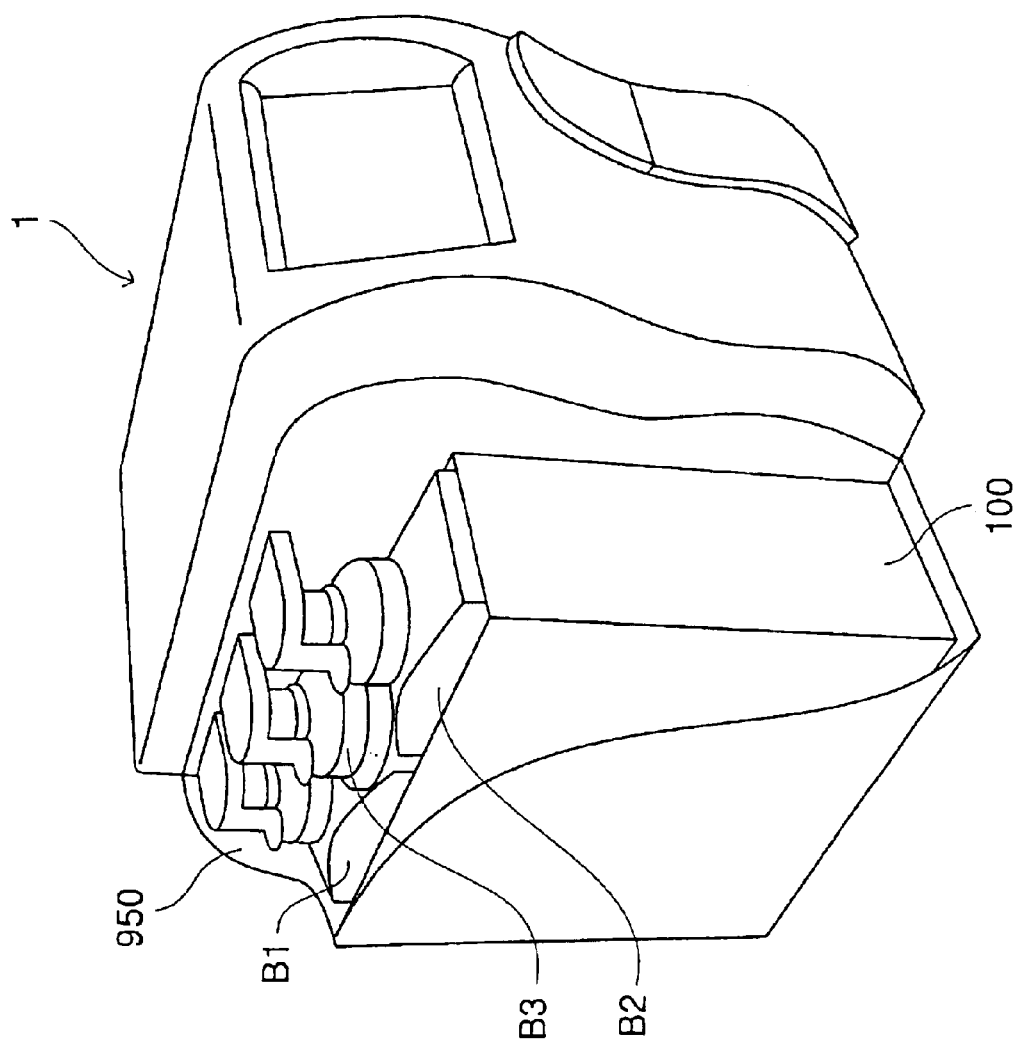
FIG. 3 is a perspective view of a container housing unit attached to the blood analyzer according to this invention.

As shown in FIG. 3, a container holder 950 is attached to a left side face of the analyzer body 1, and a container housing unit 100 which accommodates containers B1, B3 respectively containing a diluent and a hemolyzing agent and a container B2 for storing waste liquid in combination is held in the container holder 950.

Construction and Operation of Sample Setting Section

Figure 4:
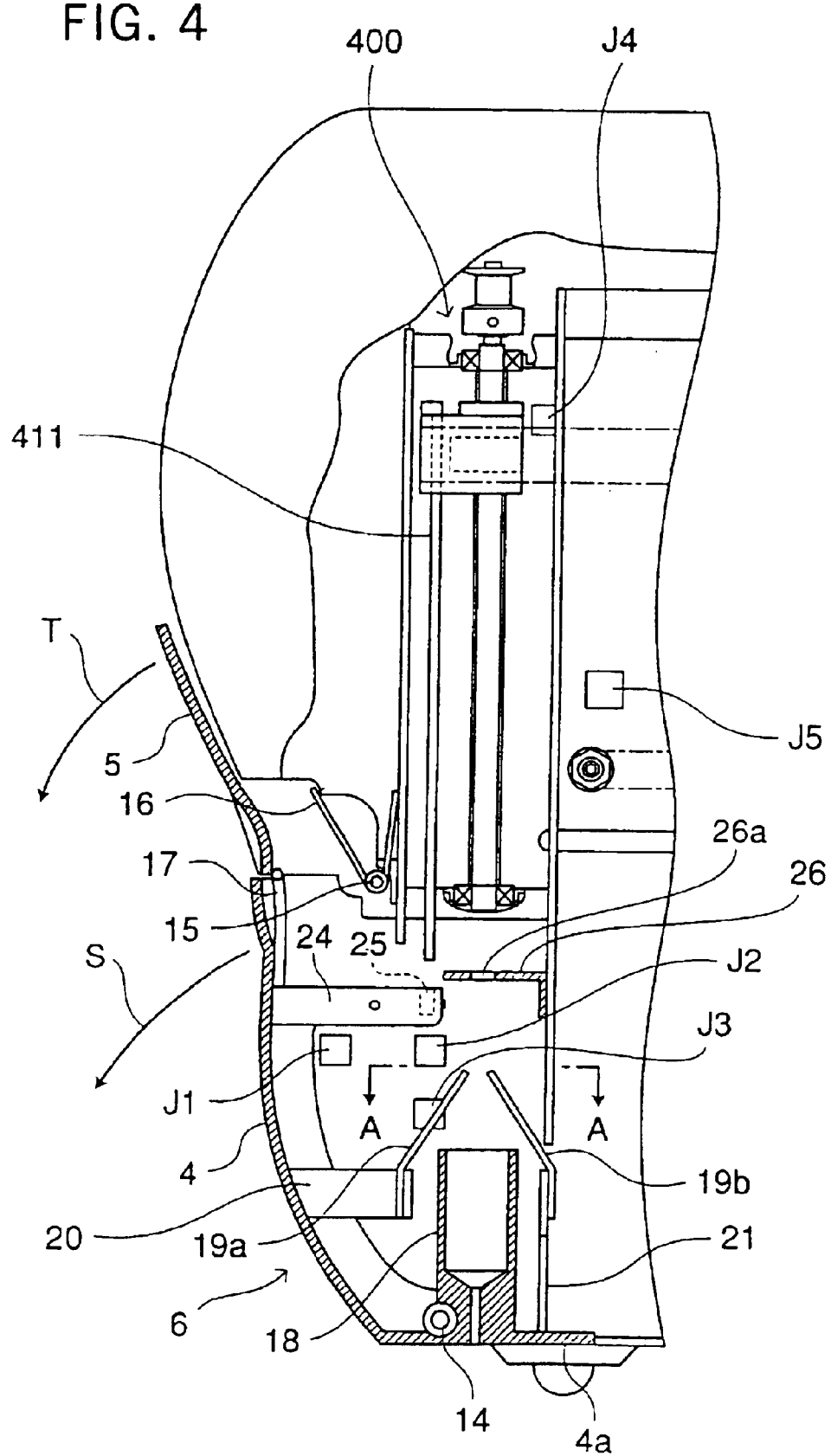
FIG. 4 is a front view of a sample setting section of the blood analyzer according to this invention.

FIG. 4 is a front view illustrating the construction of the sample setting section 6. As shown, the sample setting panel 4 is supported pivotally about a support shaft 14 in an arrow direction S, and biased in the arrow direction S by a spring not shown. Above the sample setting panel 4, the button 5 is arrow direction T by a spring 16.

A claw 17 provided on an upper edge of the sample setting panel 4 is engaged with a lower edge of the button 5 to prevent the sample setting panel 4 from opening in the arrow direction S. The sample setting panel 4 is provided with a sample rack 18 for holding a lower portion of the sample vessel. Two holder claws 19a, 19b are provided above the sample rack 18 for holding and positioning the sample vessel therebetween. Proximal ends of the holder claws 19a, 19b are fixed to a distal end of a projection piece 20 horizontally projecting from the sample setting panel 4 and a support plate 21, respectively.

Figure 5:
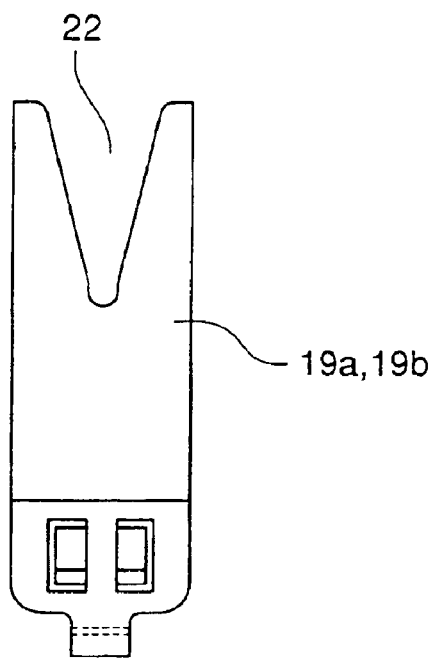
FIG. 5 is a front view of a holder claw of the blood analyzer according to this invention.
Figure 6:
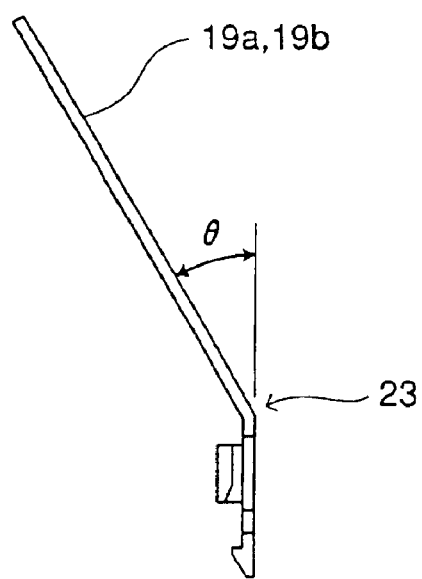
FIG. 6 is a side view of the holder claw of the blood analyzer according to this invention.
Figure 7:
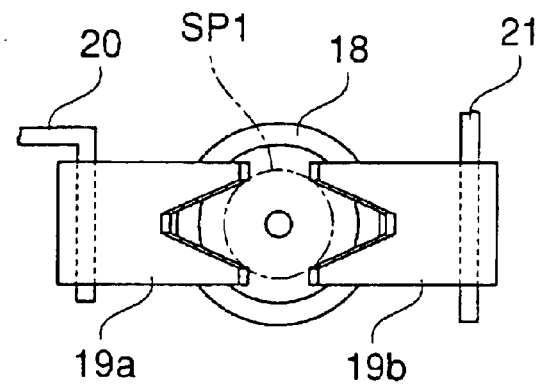
FIG. 7 is a view from an A—A arrow direction in FIG. 4.

FIGS. 5 and 6 are a front view and a side view, respectively, of the holder claw 19a, 19b. The holder claw 19a, 19b has a V-shaped notch 22 provided at its distal end, and a bent portion 23 bent at an angle θ of 30 degrees. As shown in FIG. 7, the holder claws 19a, 19b are symmetrically disposed with respect to a center line of the sample rack 18. As will be described later, a sample vessel SP1 set in the sample rack 18 is resiliently held between the holder claws 19a and 19b.

The holder claws 19a, 19b are each formed of a resilient plate (e.g., a polyacetal resin plate having a thickness of 0.8 mm). The angle θ of the bent portions 23 is resiliently changed to accommodate variations in the outer diameter of the sample vessel SP1, so that sample vessels SP1 having different outer diameters (e.g., 12 to 15 mm) can be held coaxially in the sample rack 18.

Figure 8:
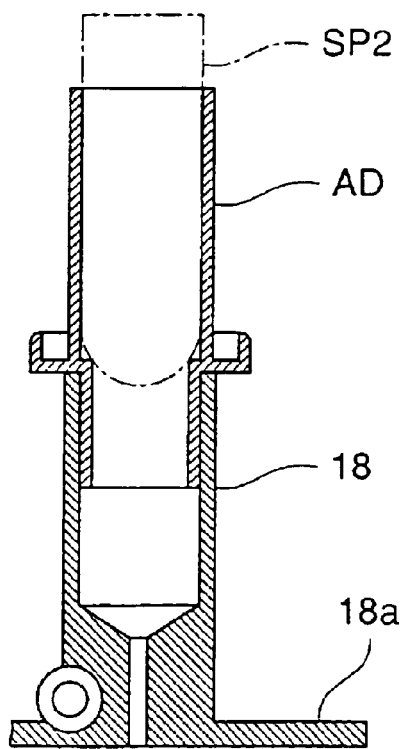
FIG. 8 is a vertical sectional view of a smaller sample vessel in a sample rack according to this invention.

FIG. 8 is a sectional view illustrating a state where a smaller sample vessel SP2 for sampling a smaller amount of a blood sample is mounted in the sample rack 18. In this case, the outer diameter and height of the sample vessel SP2 are smaller than those of the sample vessel SP1, so that an adaptor AD is inserted in the sample rack 18 for complement.

As shown in FIG. 4, a sensor (photo-interrupter) J1 for detecting the opening and closing of the sample setting panel 4, a sensor (limit switch) J2 for sensing whether a sample vessel is set in the sample rack 18, and a sensor (limit switch) J3 for sensing whether the adaptor AD is used are provided in the sample setting section 6.

Figure 9:
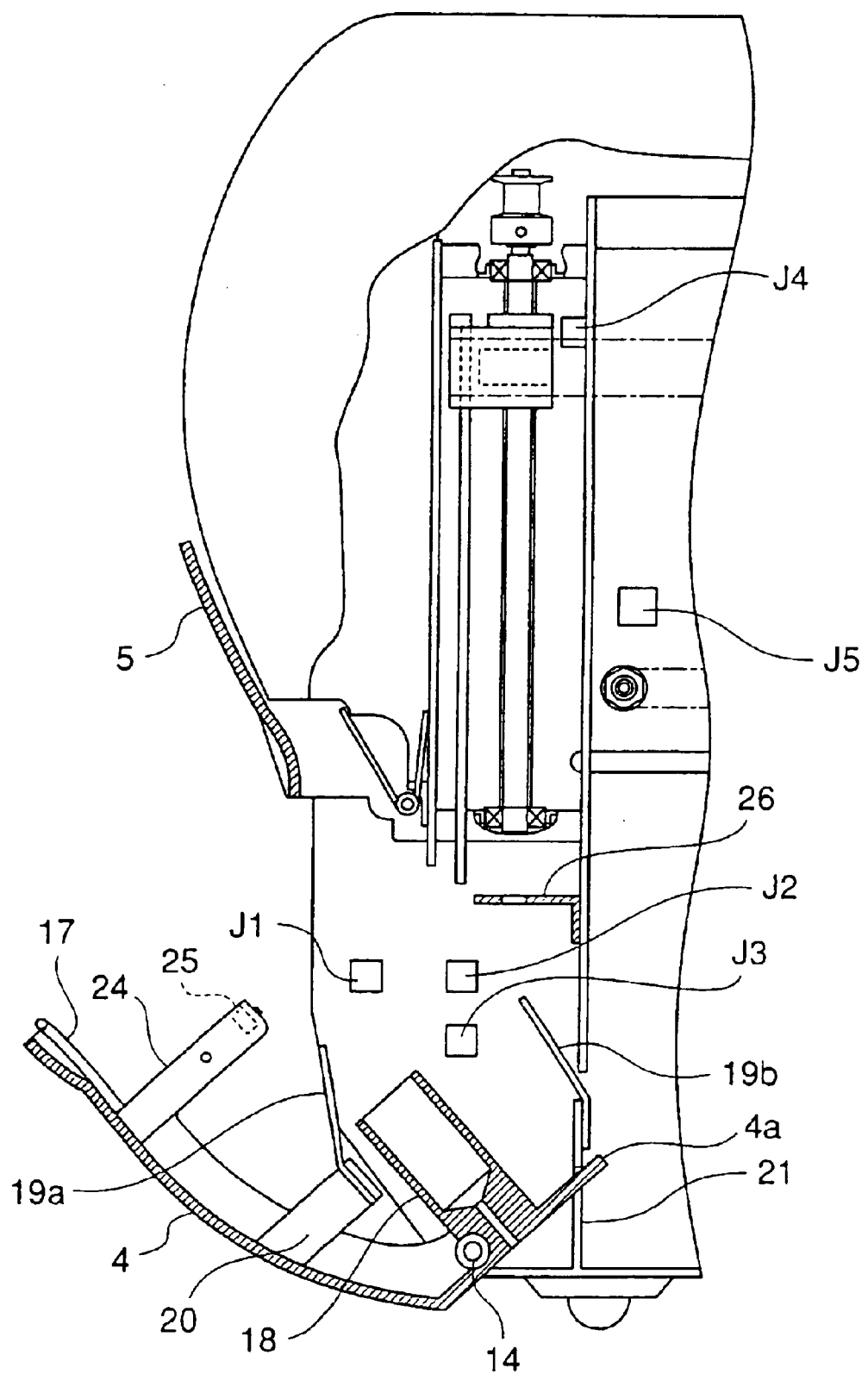
FIG. 9 is a diagram for explaining the operation of the sample setting section of the blood analyzer according to this invention.
Figure 10:
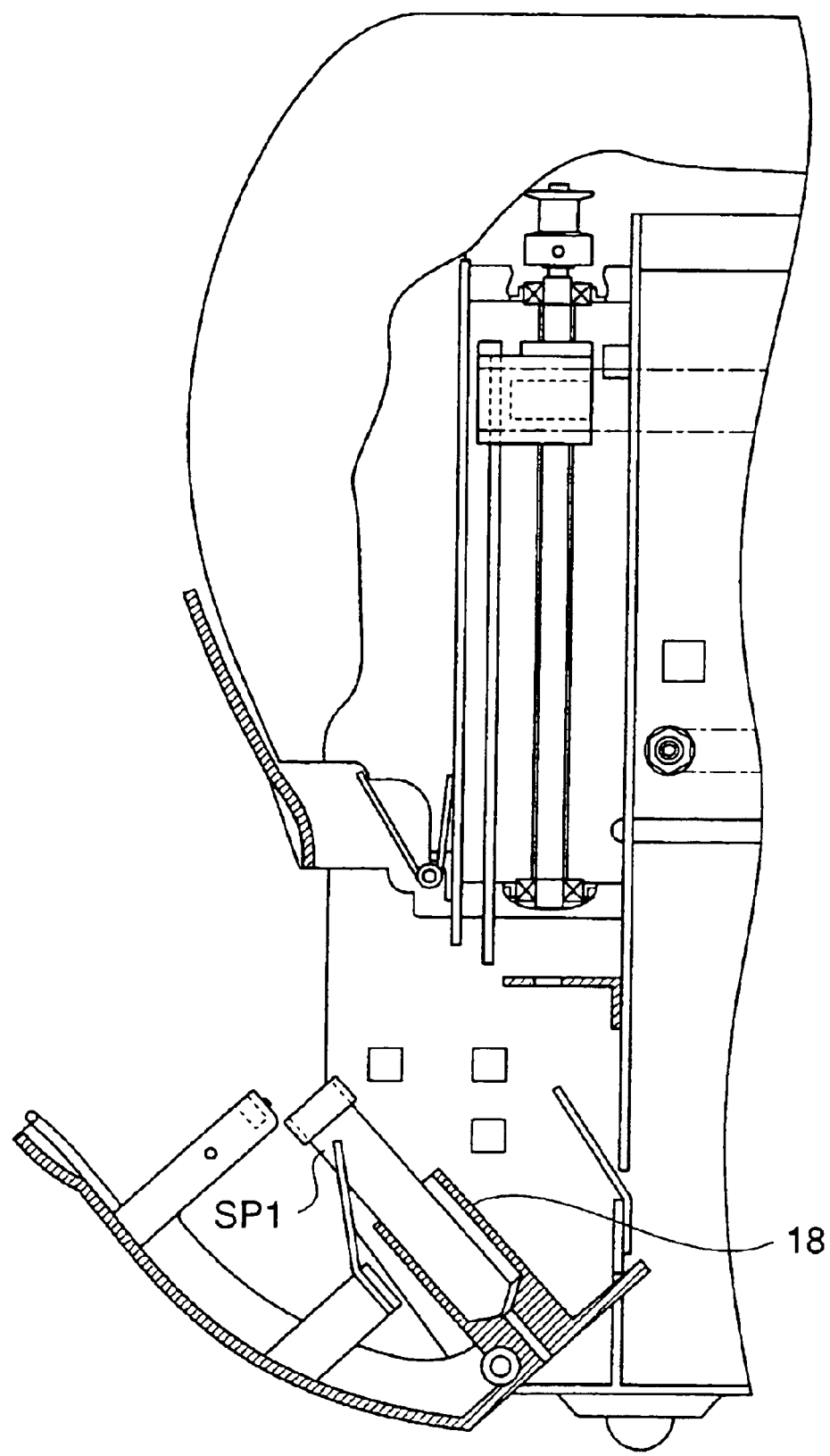
FIG. 10 is a diagram for explaining the operation of the sample setting section of the blood analyzer according to this invention.

In this arrangement, the button 5 is slightly pivoted in a direction opposite to the arrow direction T in FIG. 4 and the lower edge of the button 5 is disengaged from the claw 17, when a user presses an upper end portion of the button 5. Thus, the sample setting panel 4 is pivoted about the support shaft 14 in the arrow direction S thereby to be opened until a projection piece 4a of the sample setting panel 4 is brought into abutment against the support plate 21 as shown in FIG. 9. In this state, the user inserts the sample vessel SP1 into the sample rack 18 as shown in FIG. 10.

Figure 11:
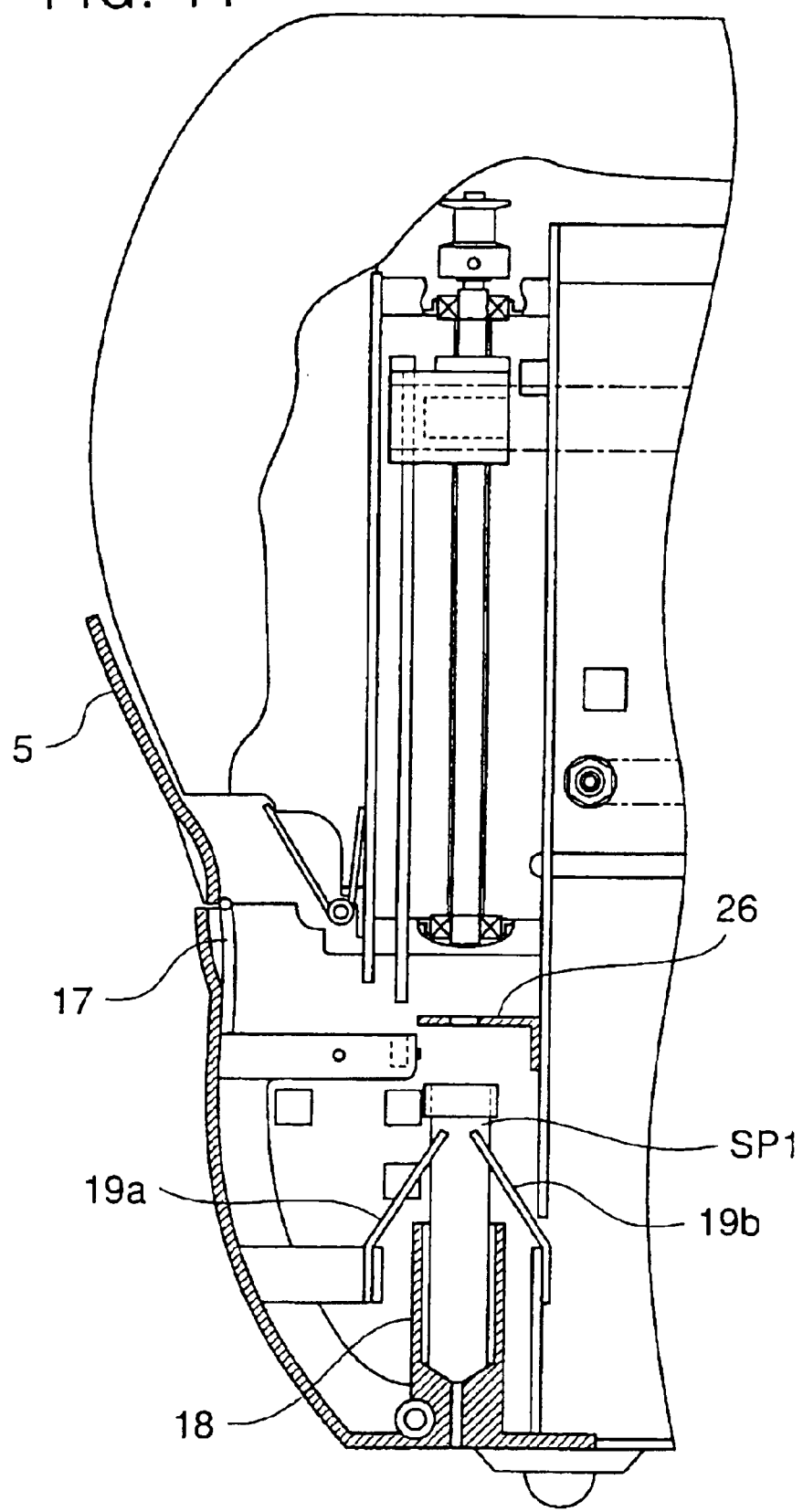
FIG. 11 is a diagram for explaining the operation of the sample setting section of the blood analyzer according to this invention.

When the sample setting panel 4 is thereafter closed as shown in FIG. 11, the claw 17 is engaged with the lower edge of the button 5, so that the sample setting panel 4 is kept closed. At this time, the sample vessel SP1 is held between the holder claws 19a and 19b coaxially with the sample rack 18. The button 5 has a relatively large surface area (60 mm×70 mm). Therefore, the user can operate the button 5 while holding the sample vessel.

Construction and Operation of Detecting Section

Figure 12:
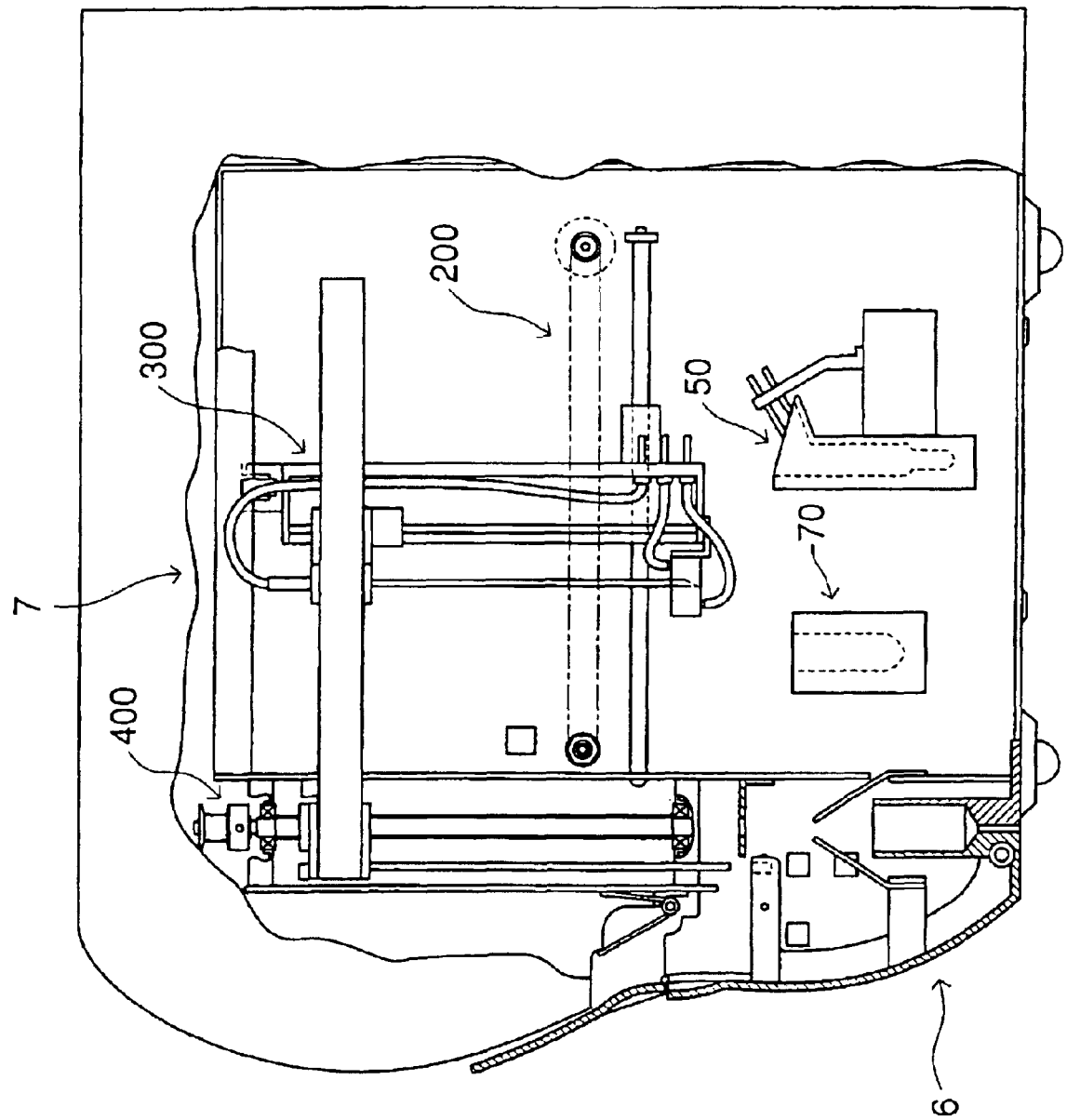
FIG. 12 is a front view of a detecting section of the blood analyzer according to this invention.

As shown in FIG. 12, the detecting section 7 includes a pipette horizontally driving section 200, a pipette vertically sliding section 300, a pipette vertically driving section 400, a mixing chamber 70 and a detector 50.

Pipette Horizontally Driving Section

Figure 13:
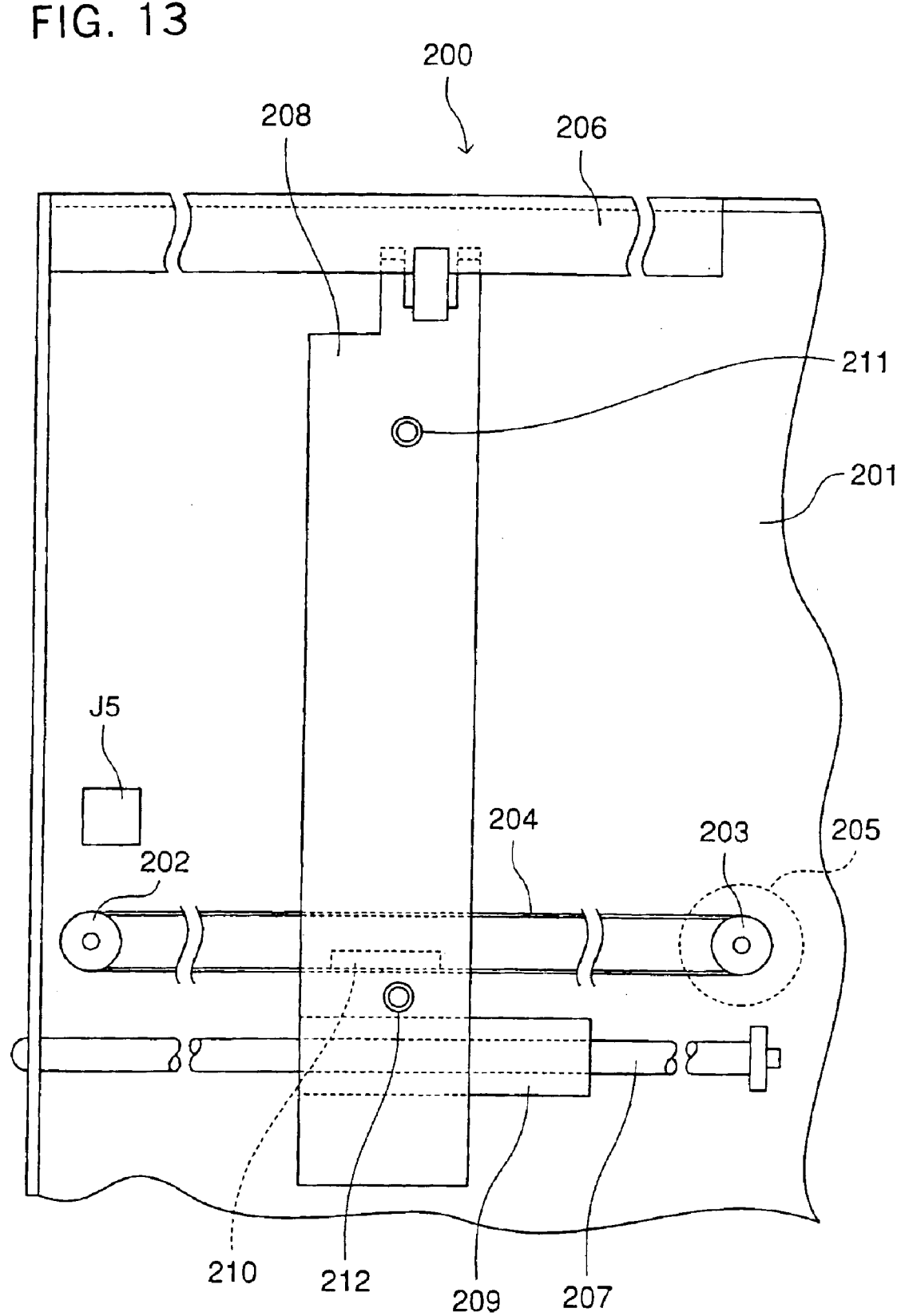
FIG. 13 is a front view of a pipette horizontally driving section of the blood analyzer according to this invention.

FIG. 13 is a front view of the pipette horizontally driving section 200.

As shown, a driven pulley 202 and a driving pulley 203 are rotatably provided on a support plate 201, and a timing belt 204 is stretched between the pulleys 202 and 203. The driving pulley 203 is driven by a pipette back and forth motor (stepping motor) 205 provided on the rear side of the support plate 201. A guide rail 206 is provided horizontally on an upper portion of the support plate 201, and a guide shaft 207 is provided horizontally on a lower portion of the support plate 201. A vertically elongated horizontal movement plate 208 has an upper edge fitted on the guide rail 206, a lower edge engaged with a sliding member 209 slidable along the guide shaft 207, and a coupling member 210 projecting from the rear side thereof to be coupled with the timing belt 204. The horizontal movement plate 208 has screw holes 211, 212 for fixing the pipette vertically sliding member 300.

With this arrangement, the horizontal movement plate 208 is horizontally movable by the driving of the motor 205. A pipette front position sensor (photo-interrupter) J5 for detecting the position of the horizontal movement plate 208 is provided on the support plate 201.

Pipette Vertically Sliding Section

Figure 14:
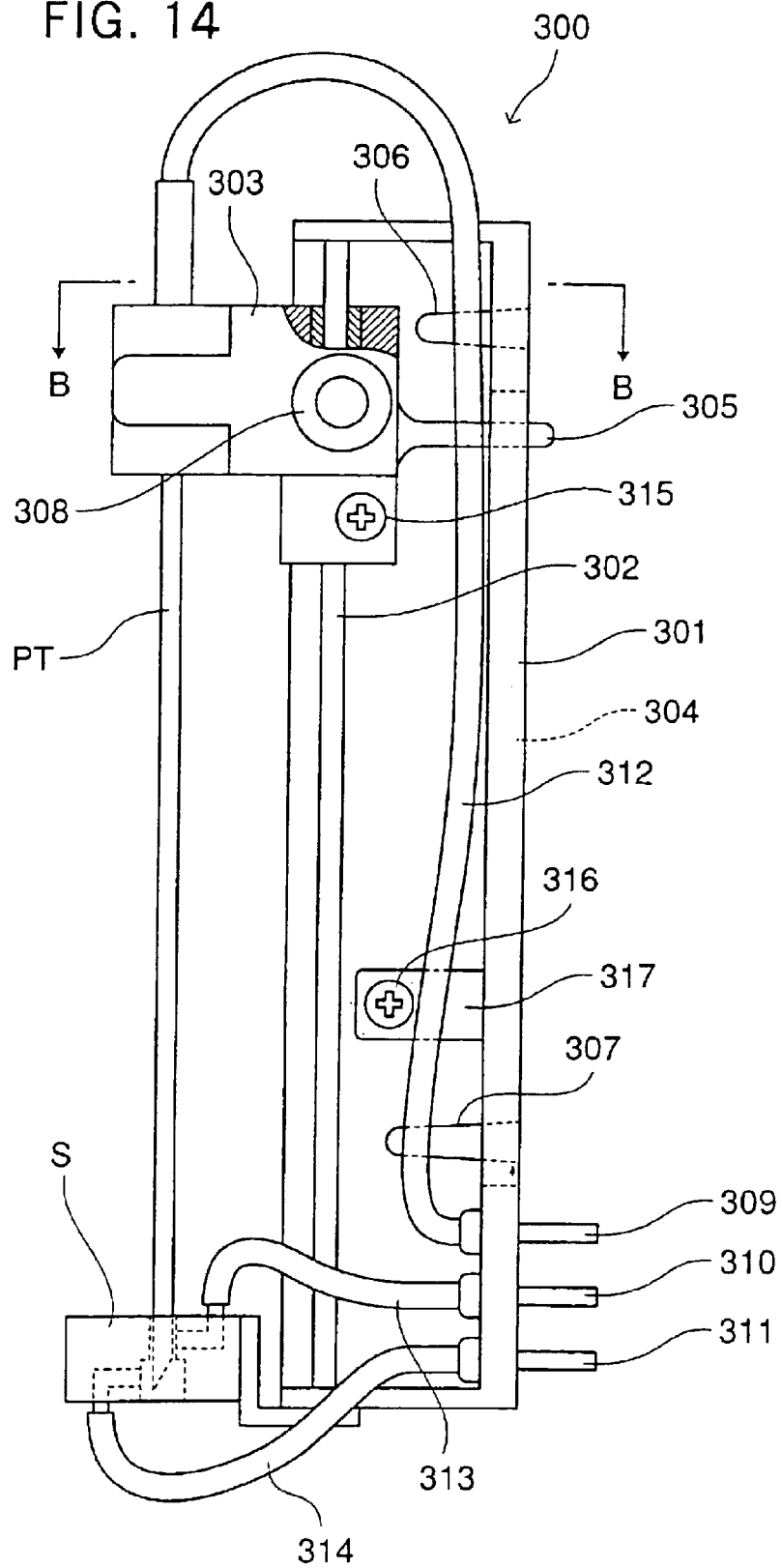
FIG. 14 is a front view of a pipette vertically sliding section of the blood analyzer according to this invention.
Figure 15:
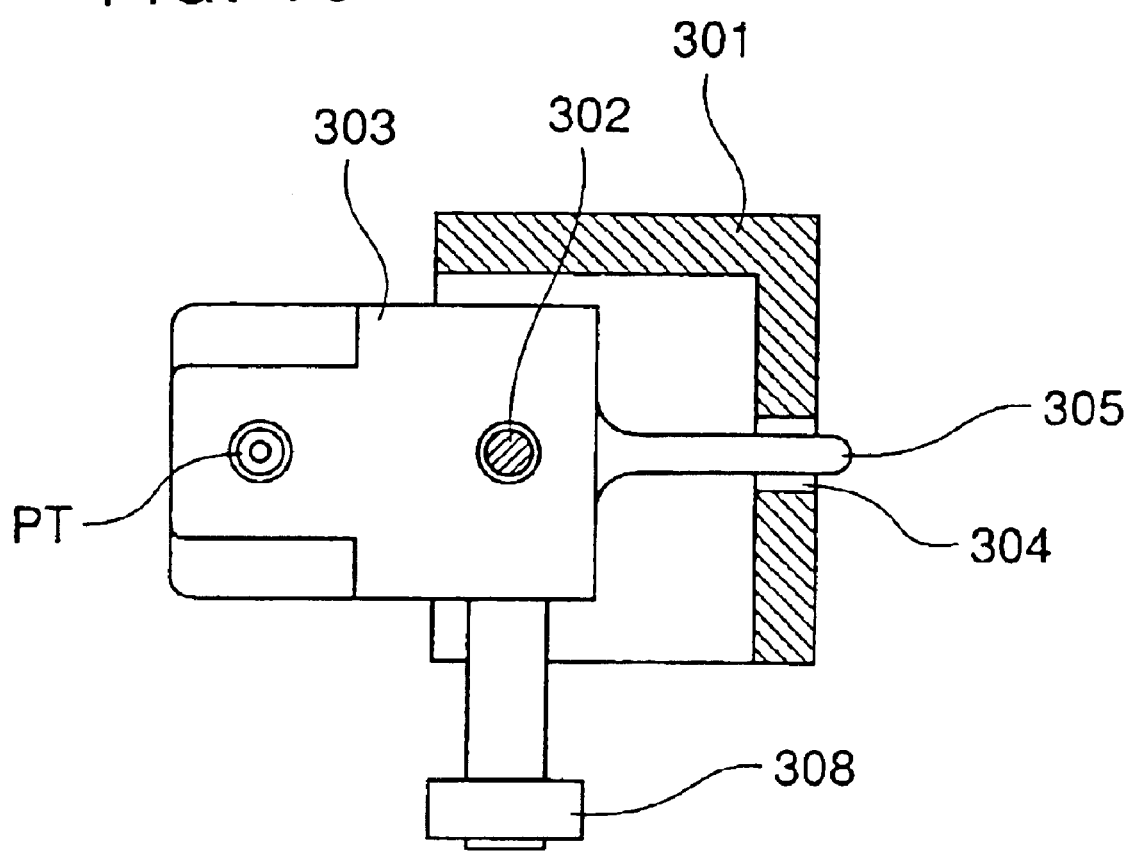
FIG. 15 is a view from a B—B arrow-direction in FIG. 14.

FIG. 14 is a front view of the pipette vertically sliding section 300, and FIG. 15 is a view from a B—B arrow direction in FIG. 14. As shown, the pipette vertically sliding section 300 includes a guide shaft 302 vertically supported by a support member 301, and a pipette holder 303 slidable on the guide shaft 302 with a pipette PT vertically held therein. The support member 301 includes a longitudinally elongated guide groove 304. A guide rod 305 horizontally projecting from the pipette holder 303 is inserted in the guide groove 304 so as to be guided by the guide groove 304, whereby the pipette holder 303 can stably be slid vertically on the guide shaft 302. The support member 301 has notches 306, 307 through which the screws extend for fixing the support member 301 to the horizontal movement plate 208 shown in FIG. 13.

Further, the pipette holder 303 has a guide roller 308, which is engaged with a guide arm (to be described later) of the pipette vertically driving section 400 to cooperate with the guide arm for moving the pipette holder 303 vertically up and down.

A cleaner (pipette cleaning device) S in which the pipette PT is inserted for cleaning the exterior and interior of the pipette PT is provided on a lower portion of the support member 301. When the pipette holder 303 is located at the uppermost position of the support member 301 (in a position shown in Fig. 14), a sharp distal tip of the pipette PT is inserted in the cleaner S.

Liquid supply/drain nipples 309, 310 and 311 fixed to a lower portion of the support member 301 are connected to a proximal end of the pipette PT and ports of the cleaner S via tubes 312, 313 and 314, respectively.

Figure 16:
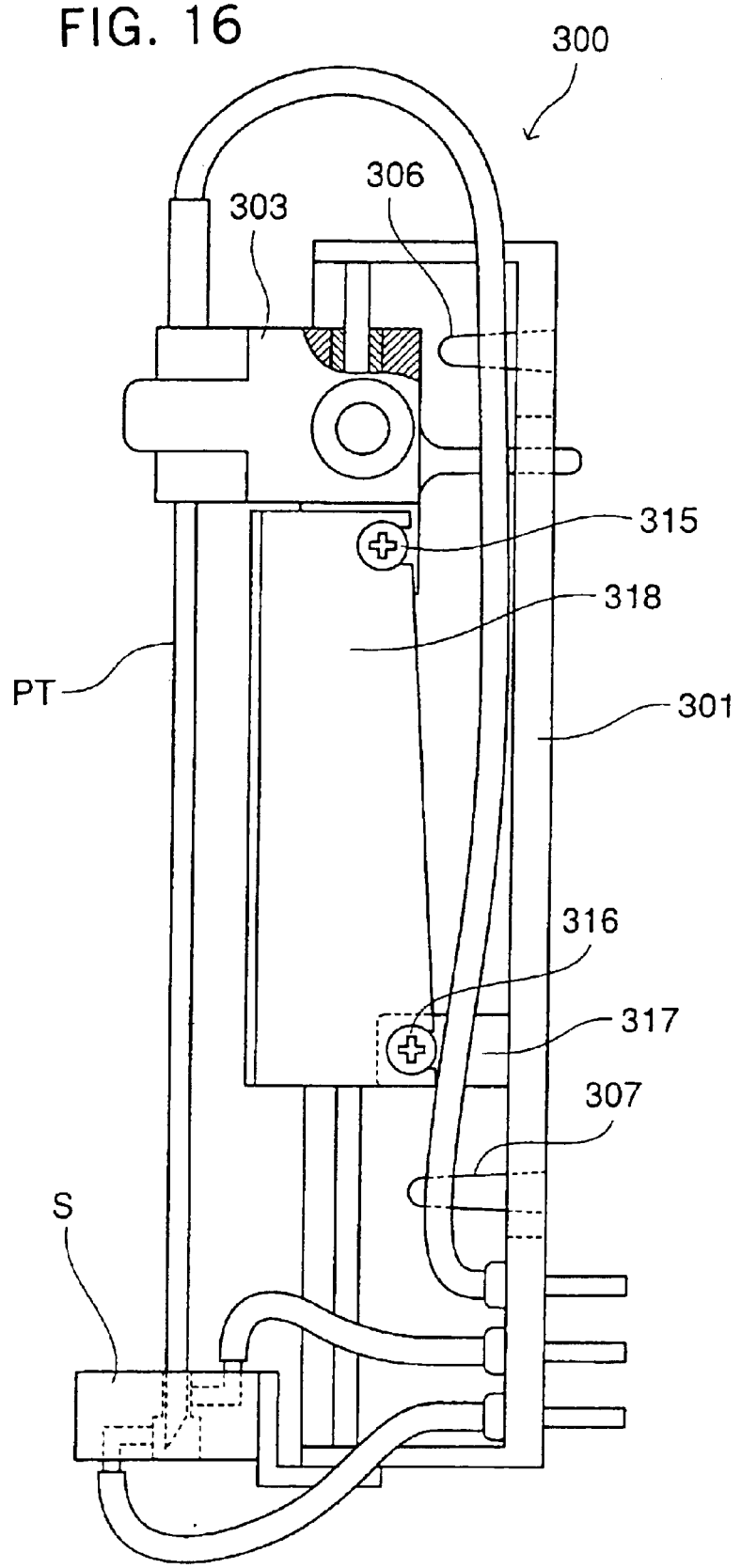
FIG. 16 is a front view of the pipette vertically sliding section of the blood analyzer according to this invention.

A screw 315 fixed to the pipette holder 303 and a screw 316 fixed to a projection 317 of the support member 301 are provided for fixing a spacer plate 318 as shown in FIG. 16. The spacer 318 fixed as shown in FIG. 16 fixes the pipette holder 303 in the uppermost position of the support member 301 for preventing the sharp tip of the pipette PT from being withdrawn from the cleaner S.

The pipette vertically sliding section 300 is first rested on the horizontal movement plate 208 shown in FIG. 13 with the spacer 318 fixed thereto and, after screws 319, 320 (FIG. 17) are screwed into the screw holes 211, 212 through the notches 306, 307, the spacer 318 is removed by unscrewing the screws 315, 316. Thus, the pipette vertically sliding section 300 can safely be mounted on the pipette horizontally driving section 200 with no possibility that the user is injured by the tip of the pipette PT. Where a trouble such as clogging occurs in the pipette PT, the pipette vertically sliding section 300 is entirely replaced. At this time, the spacer 318 is employed to safely perform a replacing operation.

Figure 17:
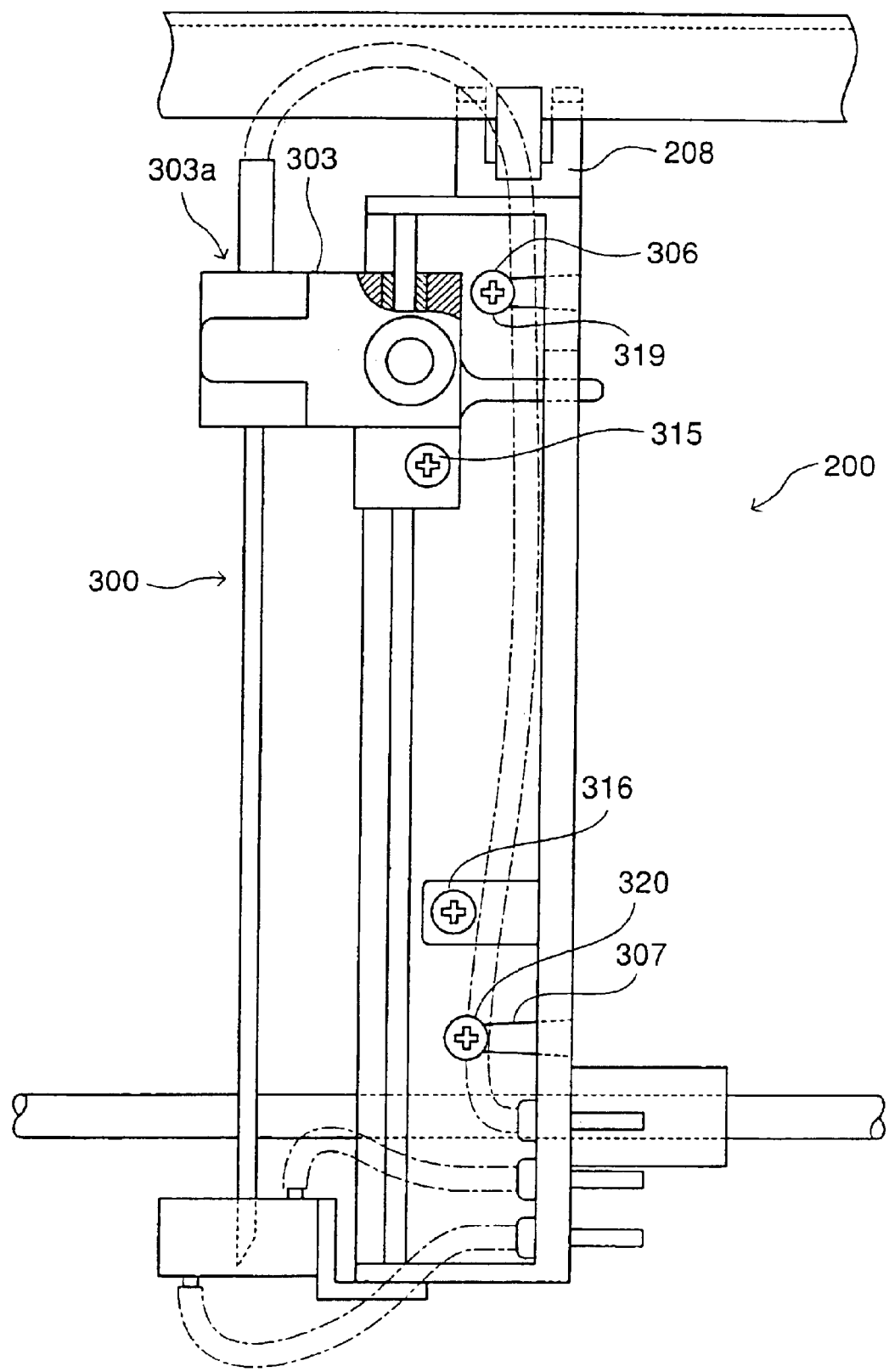
FIG. 17 is a front view of major portions of the pipette vertically sliding section and the pipette horizontally driving section according to this invention.
Figure 18:
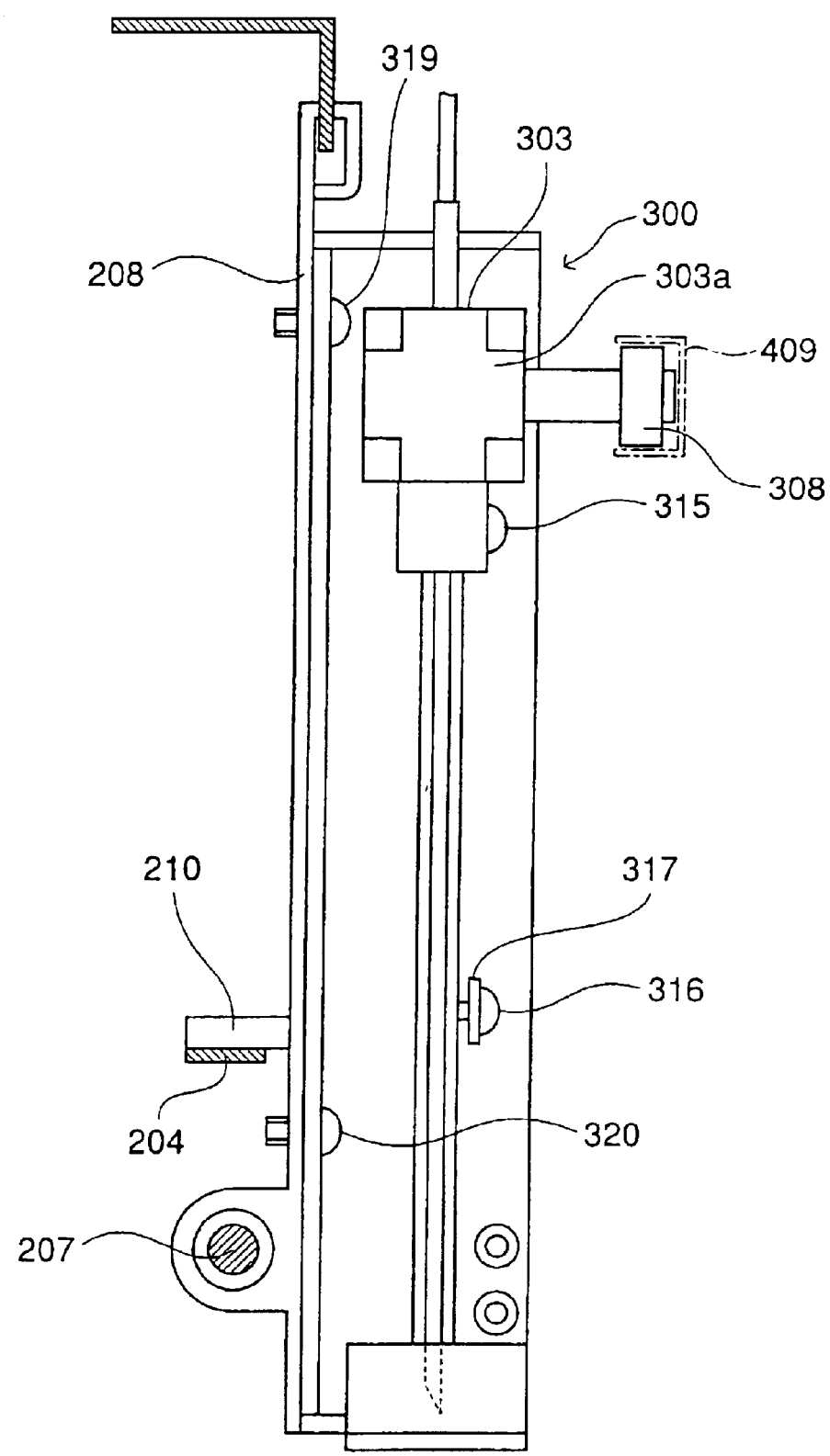
FIG. 18 is a left side view of major portions of the pipette vertically sliding section and the pipette horizontally driving section according to this invention.

FIGS. 17 and 18 are a front view and a left side view, respectively, illustrating a state where the pipette vertically sliding section 300 is mounted on the pipette horizontally driving section 200. As shown, an end 303a of the pipette holder 303 of the pipette vertically sliding section 300 has a cross shape in section so as to be inserted in a main arm (to be described later) of the pipette vertically driving section 400.

Pipette Vertically Driving Section

Figure 19:
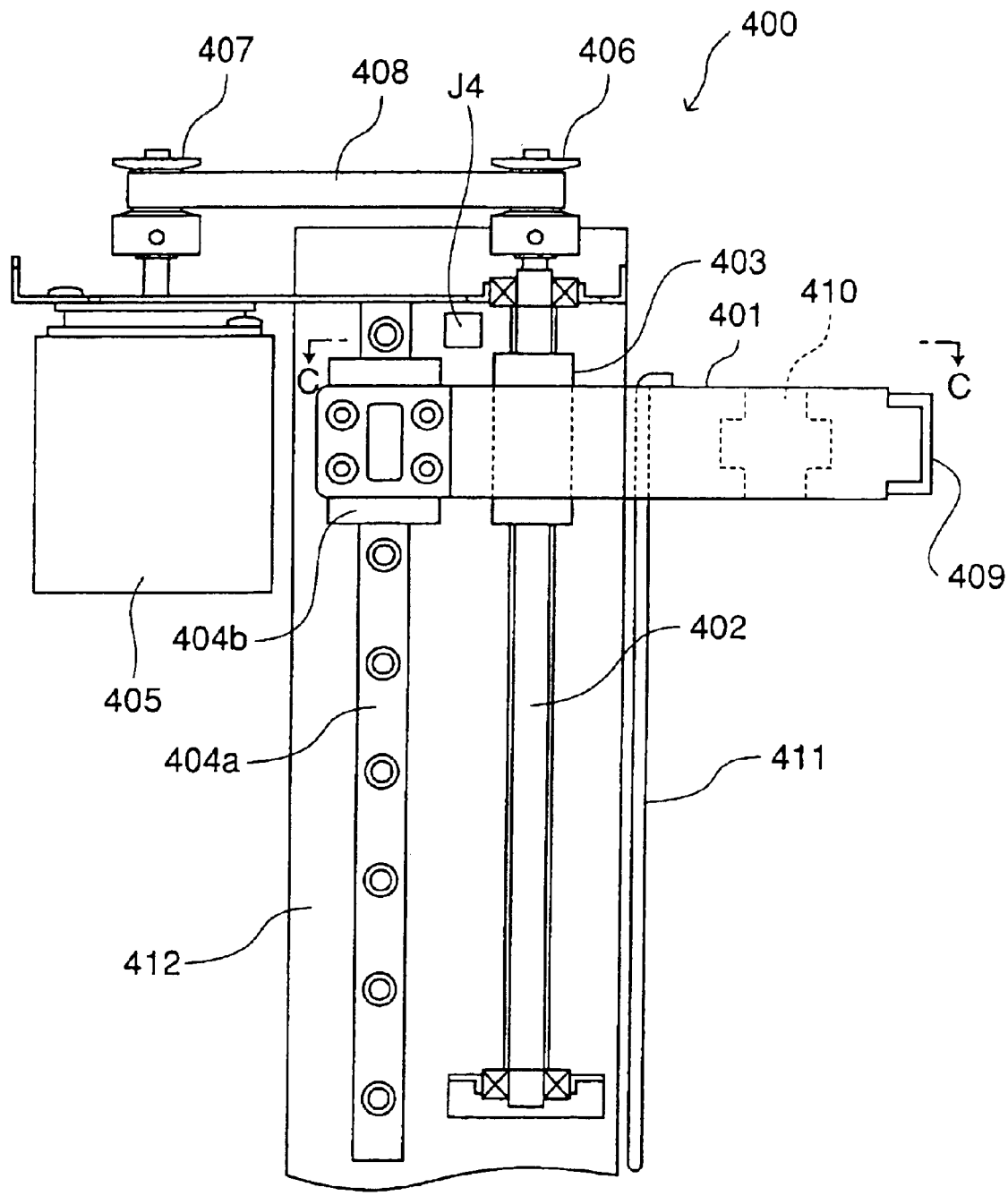
FIG. 19 is a left side view of a pipette vertically driving section according to this invention.
Figure 20:
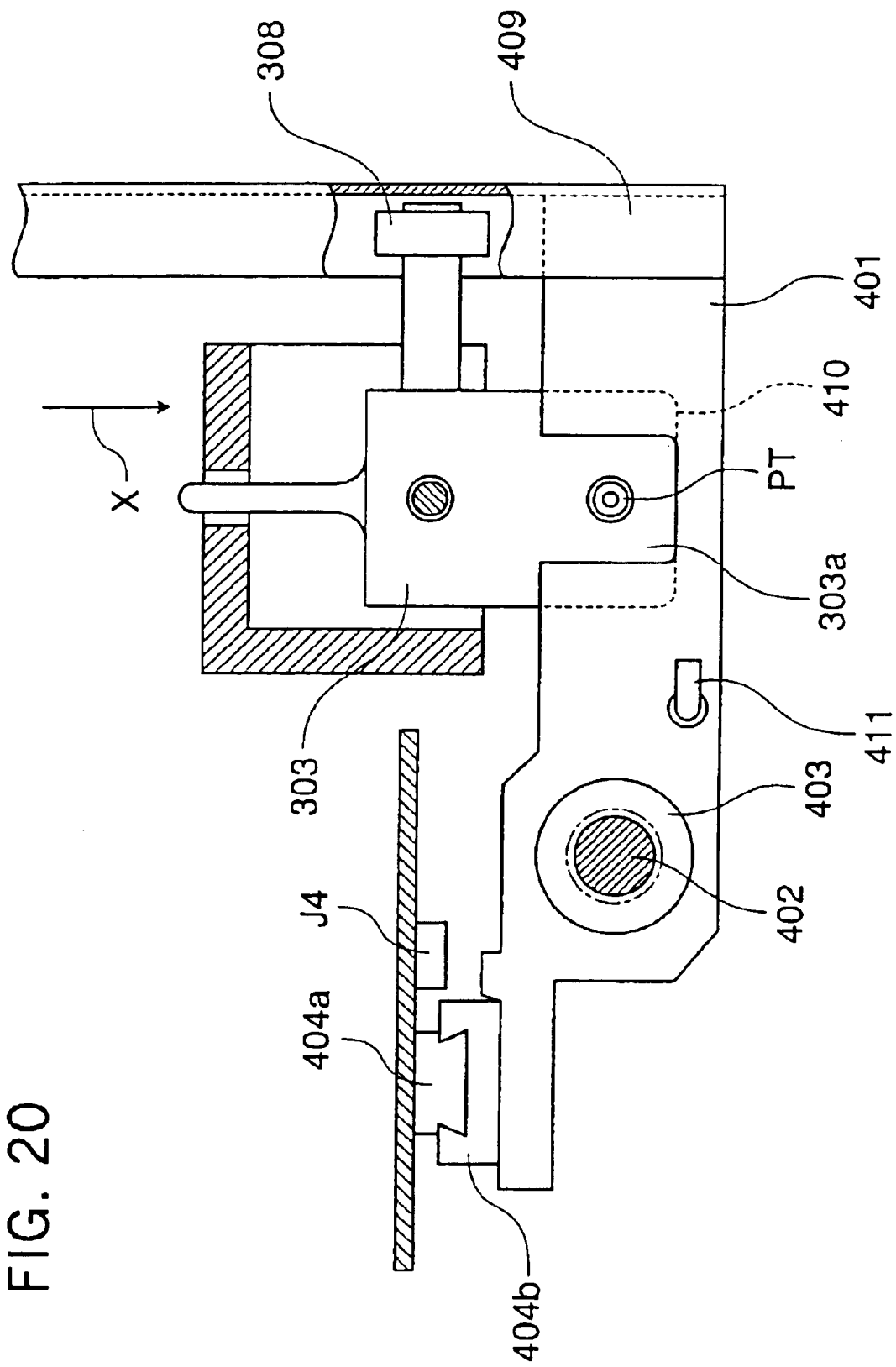
FIG. 20 is a view from a C—C arrow direction in FIG. 19.

FIG. 19 is a left side view of the pipette vertically driving section 400, and FIG. 20 is a view from a C—C arrow direction in FIG. 19.

As shown in FIG. 19, the pipette vertically driving section 400 includes an elongated main arm 401 extending horizontally, a thread shaft 402 extending perpendicularly through the main arm 401 and rotatably supported by a support plate 412, a nut 403 fixed to the main arm 401 in threading engagement with the thread shaft 402, a slide rail 404a disposed parallel to the thread shaft 402 on the support plate 412, a sliding member 404b provided at a left end of the main arm 401 in slidable engagement with the slide rail 404a for vertically guiding the main arm 401, and a pipette up and down motor (stepping motor) 405 fixed to the support plate 412.

Pulleys 406 and 407 are fixed to an upper end of the thread shaft 402 and an output shaft of the motor 405, respectively, and a timing belt 408 is stretched between the pulleys 406 and 407. Therefore, the main arm 401 is movable vertically up and down by the driving of the motor 405. A pipette top position sensor J4 for sensing that the main arm 401 reaches the uppermost position is provided on the support plate 412.

A guide arm 409 is horizontally fixed to a right end of the main arm 401 in engagement with the guide roller 308 of the pipette vertically sliding section 300 (FIG. 18). The main arm 401 has a cross-shaped recess 410 provided in a surface thereof opposed to the cross-shaped end 303a of the pipette holder 303 (FIGS. 17 and 18). As shown in FIG. 20, the end 303a of the pipette holder 303 is removably inserted in an arrow direction X into the recess 410 with a proper clearance. In this case, a force for the vertical movement of the main arm is directly transmitted to the pipette holder 303. A lock rod 411 extends vertically through a middle portion of the main arm 401 with an upper end bent portion thereof in engagement with the main arm 401. In this embodiment, the main arm 401 is composed of an aluminum alloy (A5052) and has a section of 20 mm×26 mm and a length of 108 mm. The guide arm 409 is prepared by folding a 0.5-mm thick steel plate (SECC) into an open square shape in section, and has a length of 180 mm.

Figure 21:
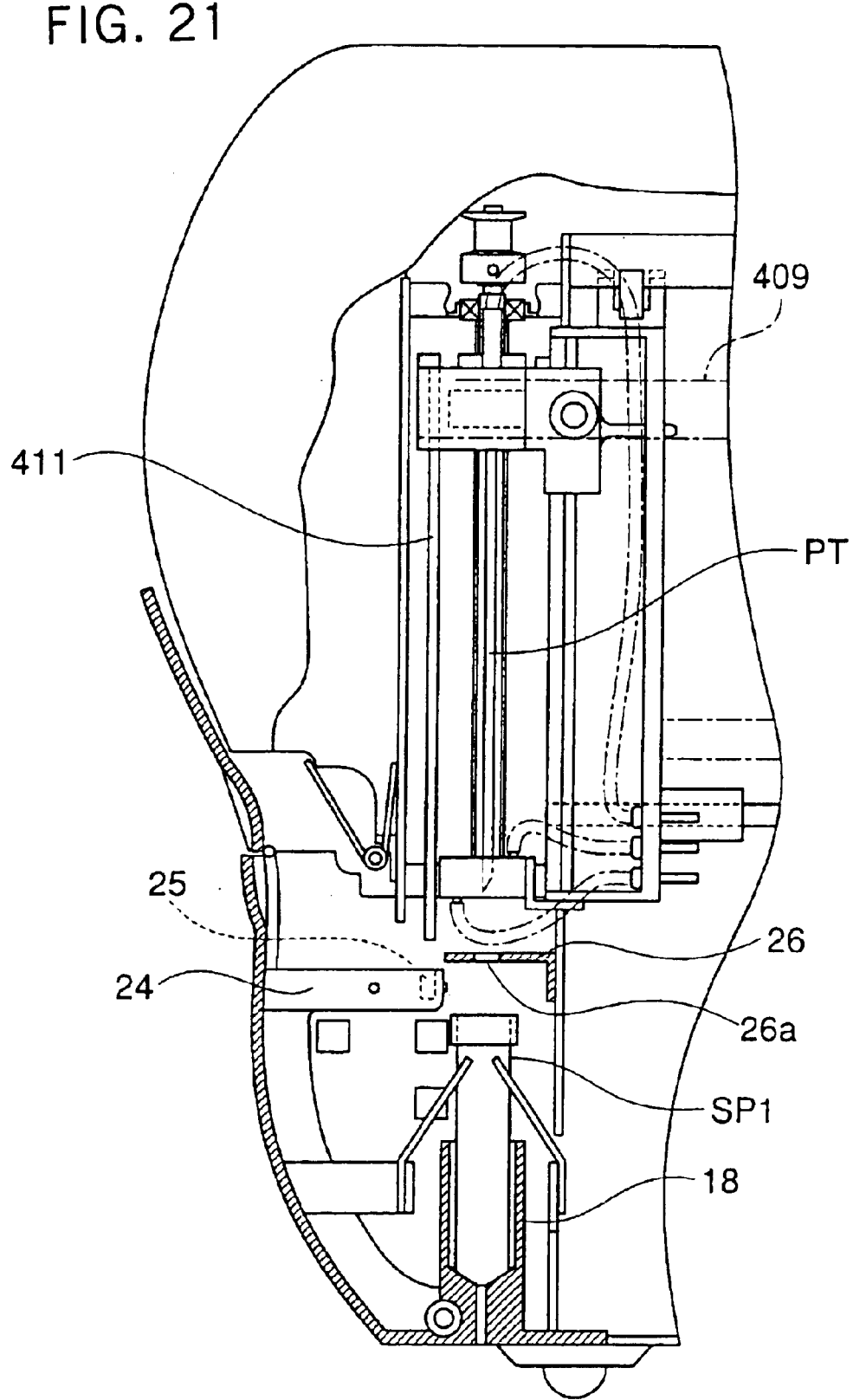
FIG. 21 is a diagram for explaining the operation of the pipette vertically driving section according to this invention.

Operations of Pipette Horizontally Driving Section, Pipette Vertically Sliding Section and Pipette Vertically Driving Section When the blood sample is quantitatively dispensed out of the sample vessel SP1 set in the sample rack 18 in the sample setting section 6, the pipette back and forth motor 205 is driven to insert the end 303a of the pipette holder 303 into the recess 410 of the main arm 401 as shown in FIG. 20, and the pipette up and down motor 405 is driven to move up the main arm 401 until the actuation of the pipette top position sensor J4 as shown in FIG. 21. With the end 303a fitted in the recess 410, the centers of the thread shaft 402, the pipette PT and the sample vessel SP1 are present in the same plane, and a moment exerted on the pipette PT by the thread shaft 402 is minimized. Therefore, the torque of the motor 405 is efficiently converted into a pipette lowering force, when the pipette PT is lowered by the motor 405.

Figure 22:
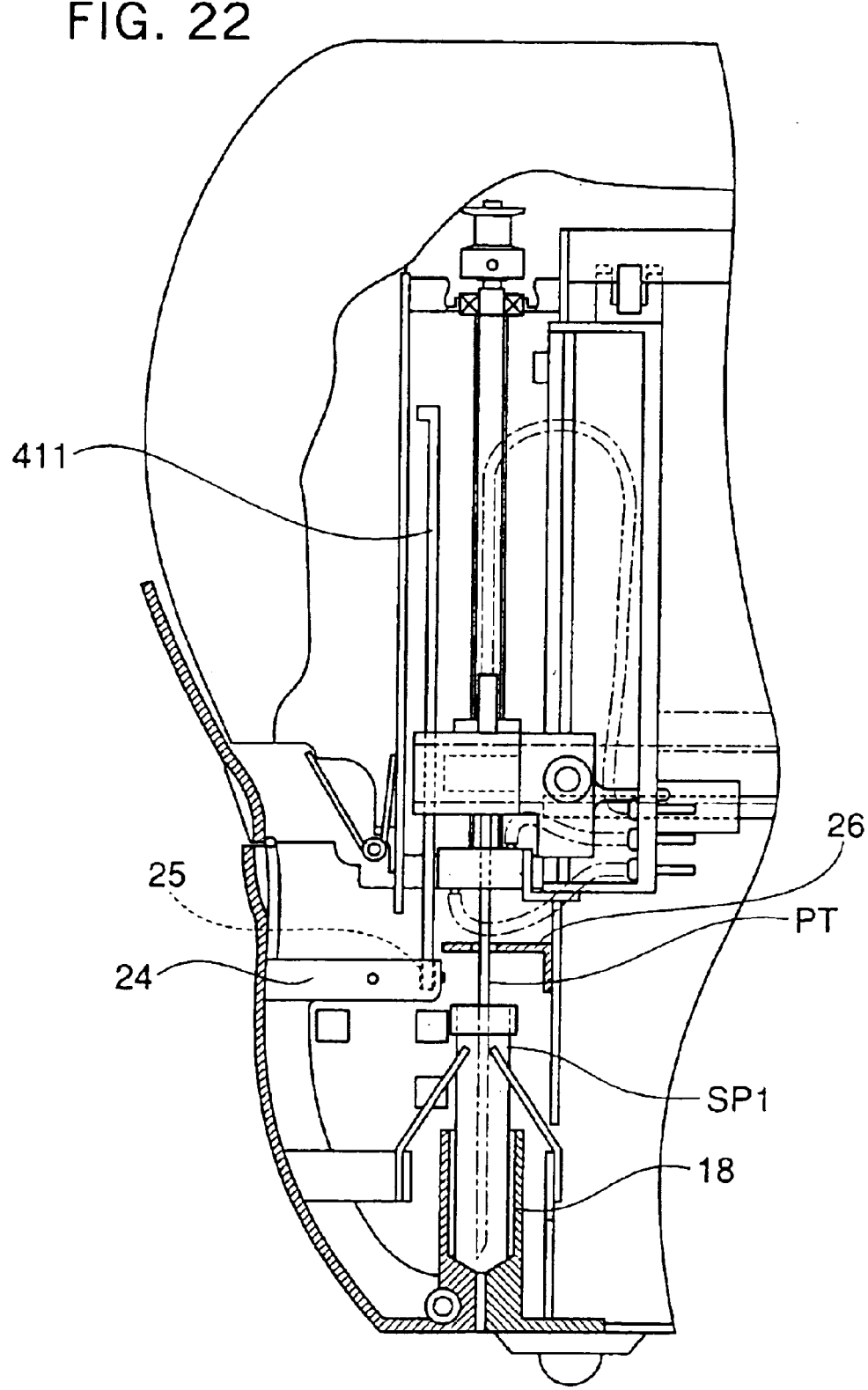
FIG. 22 is a diagram for explaining the operation of the pipette vertically driving section according to this invention.

Then, the motor 405 is driven to lower the pipette PT through a through-hole 26a of a sample vessel lift preventing stopper 26 as shown in FIG. 21, and to allow the pipette PT to virtually reach the bottom of the sample vessel SP1 as shown in FIG. 22. Where the sample vessel SP1 is a vacuum blood sampling tube with a rubber cap, it is necessary to piece the rubber cap with the tip of the pipette PT. Therefore, an input electric current greater than usual is supplied to the motor 405 from a driver circuit section (to be described later) to provide a greater output torque when the pipette PT is lowered to pierce through the rubber cap.

When the pipette PT is lowered, the lock rod 411 is brought into engagement with a lock hole 25 provided in a projection piece 24 projecting inward of the sample setting panel 4 as shown in FIG. 22, so that the pipette PT and the sample vessel SP1 are prevented from being damaged when the sample setting panel 4 is inadvertently opened. Where the smaller sample vessel SP2 is set in the sample rack 18 with the intervention of the adaptor AD as shown in FIG. 8, the sample adaptor detecting sensor J3 is actuated. Therefore, a control section 500 to be described later controls a lowering distance of the pipette PT to allow the tip of the pipette PT to virtually reach the bottom of the smaller sample vessel SP2.

Upon completion of intake of the blood sample, the pipette PT returns to the position shown in FIG. 21. Although there would be a possibility that the pipette PT is lifted together with the rubber cap sticking thereto when the pipette PT is removed from the sample vessel SP1, the stopper 26 prevents the rubber cap from being lifted together.

When the pipette PT is returned to the position shown in FIG. 21, the pipette back and forth motor 205 is driven to withdraw the end 303a of the pipette holder 303 from the recess 410 of the main arm 401 in a direction opposite to the arrow direction X in FIG. 20, and then move the pipette PT to an upper side of the mixing chamber 70 and the detector 50 with the guide roller 308 rotated in contact with the inner surface of the guide arm 409. Then, the pipette up and down motor 405 is driven, whereby a driving force thereof is transmitted to the pipette holder 303 through the main arm 401, the guide arm 409 and the guide roller 308. Thus, the pipette PT is lowered and then lifted.

Construction of Detector

Figure 23:
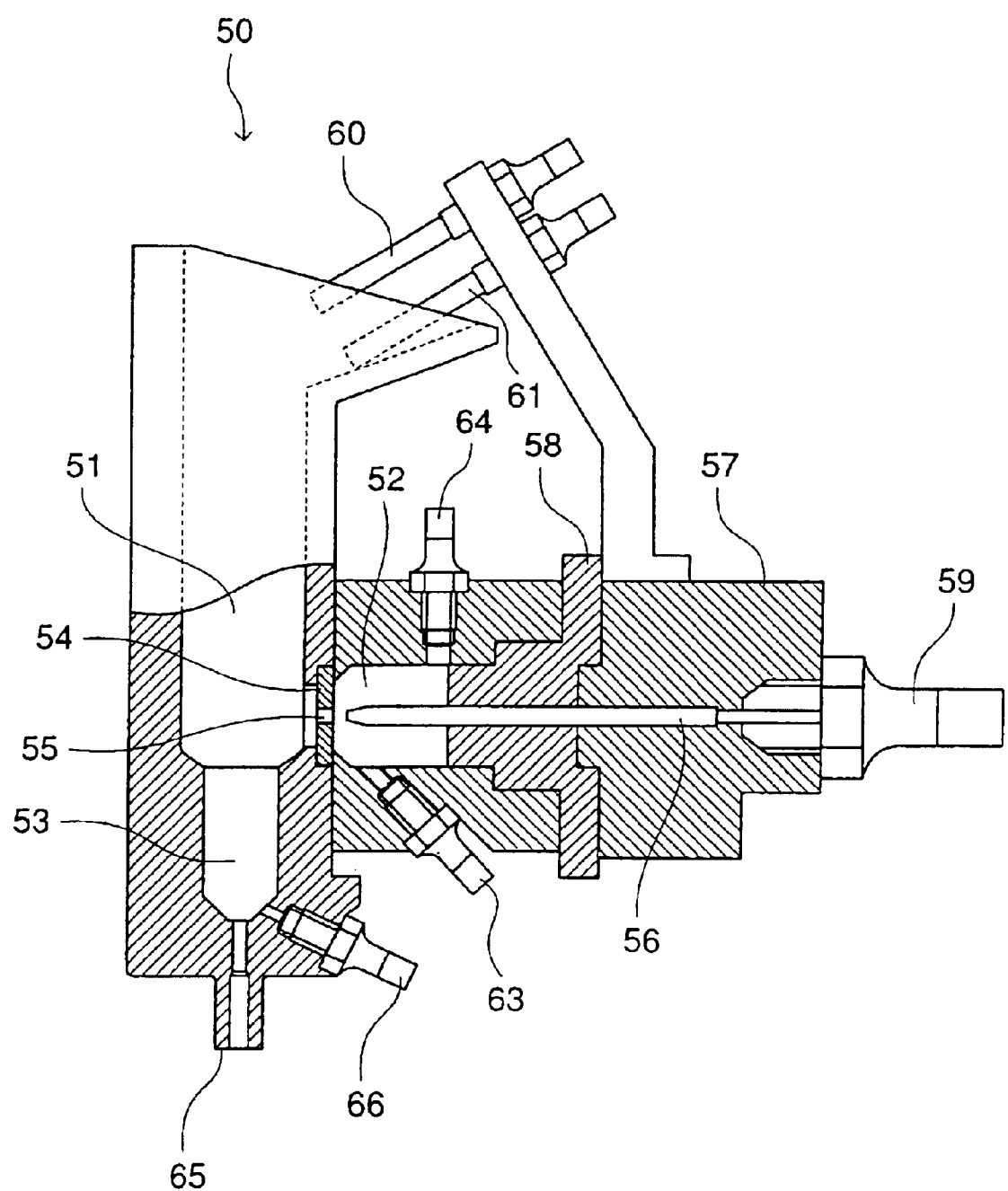
FIG. 23 is a partly cut-away front view of major portions of a detector according to this invention.
Figure 24:
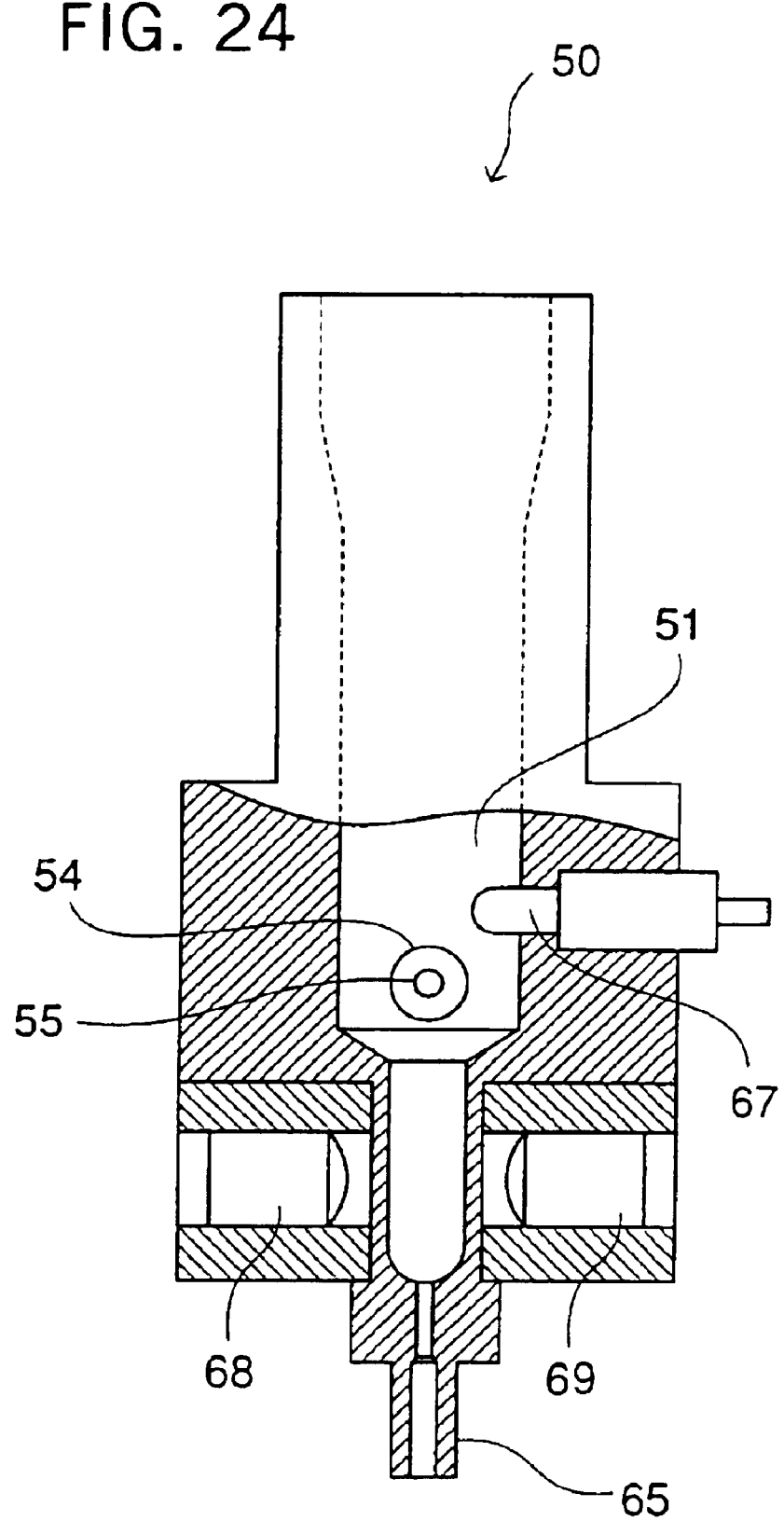
FIG. 24 is a partly cut-away side view of major portions of the detector according to this invention.

FIGS. 23 and 24 are a partly cut-away front view and a partly cut-away side view, respectively, of major portions of the detector 50. The detector 50 is composed of a transparent polysulfone resin. As shown, the detector 50 includes first, second and third container chambers 51, 52, 53 for containing liquids for the analysis. The first container chamber 51 has an upper portion open to the atmosphere. The first container chamber 51 and the third container chamber 53 communicate with each other.

A ruby orifice disk 54 is provided as a partition between the first container chamber 51 and the second container chamber 52, and the disk 54 has an orifice 55 having a diameter of 80 μm. The second container chamber 52 is provided with a jet nozzle 56. The jet nozzle 56 is supported by a nozzle support member 57 and an electrode 58, and extends through the second container chamber 52 with its distal end facing toward the orifice 55 and with its tail end communicating with a liquid supply nipple 59. The electrode 58 is composed of a stainless steel, and exposed to the inside of the second container chamber 52.

The detector 50 further includes nozzles 60, 61 for supplying the diluent and the hemolyzing agent to the first container chamber 51, nipples 63, 64 for supplying and draining liquid into/from the second container chamber 52, and a liquid draining nipple 65 and an air bubble injecting nipple 66 provided in the bottom of the third container chamber 53.

As shown in FIG. 24, the detector 50 further includes a platinum electrode 67 projecting in the first container chamber 51, and a light emitting diode 68 and a photodiode 69 respectively disposed on opposite sides of the third container chamber 53. The light emitting diode 68 emits light having a wavelength of 555 nm, and the photodiode 69 detects the intensity of the light transmitting through the third container chamber 53. The light emitting diode 68 and the photodiode 69 are employed for measurement of a hemoglobin amount (HGB). The electrodes 67, 58 are employed for measuring a change in the impedance of the liquid passing through the orifice 55 for counting the numbers of white blood cells, red blood cells and platelets.

As will be described later, the first and third container chambers 51, 53 are employed for preparation of a white blood cell measurement specimen, and the first and second container chambers 51, 52 are employed for counting the numbers of the white blood cells, the platelets and the red blood cells.

Construction of Mixing Chamber (Container for Mixing Liquids)

Figure 25A:
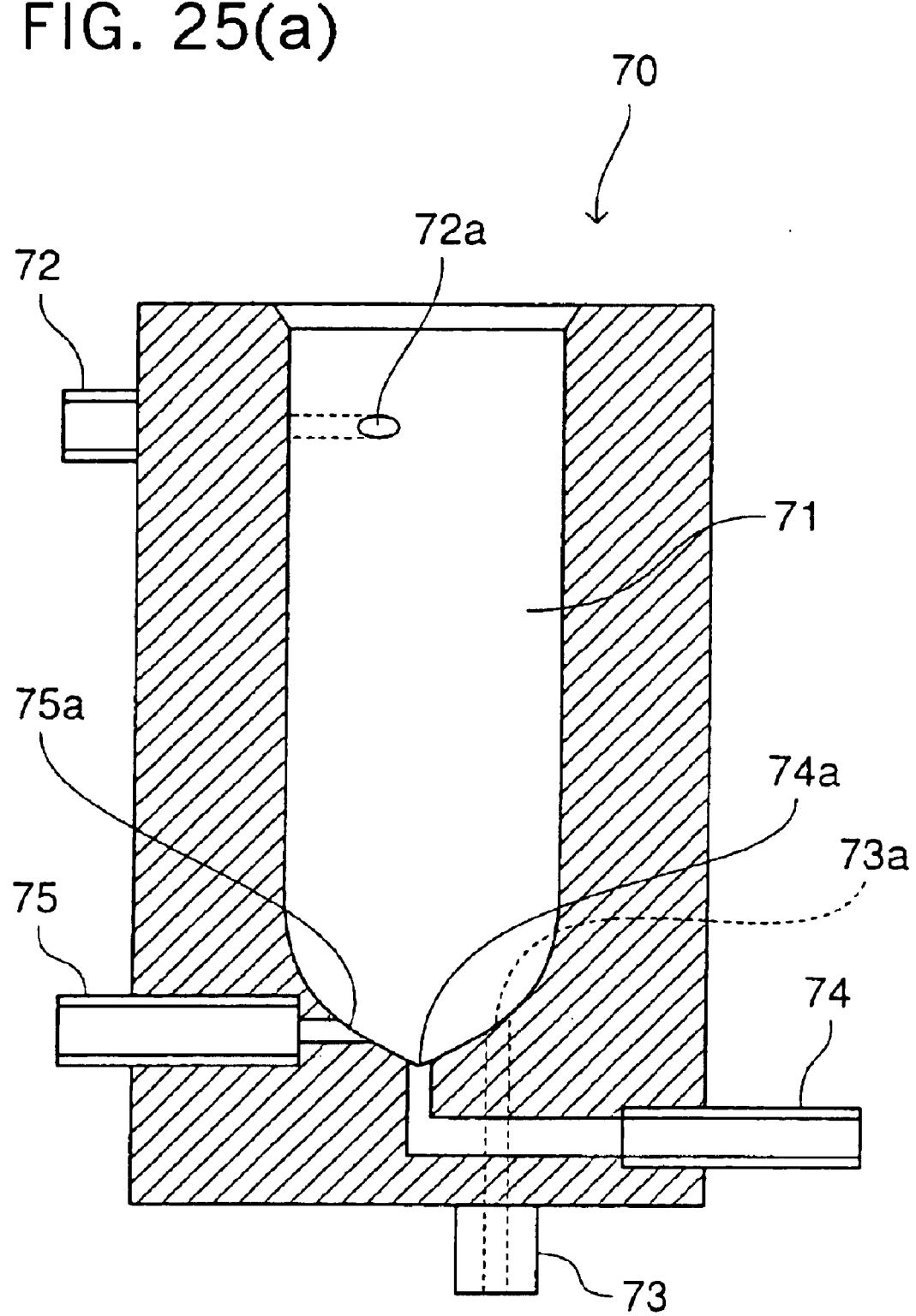
FIGS. 25(a) and 25(b) are a sectional view and a plan view, respectively, of a mixing chamber according to this invention.
Figure 25B:
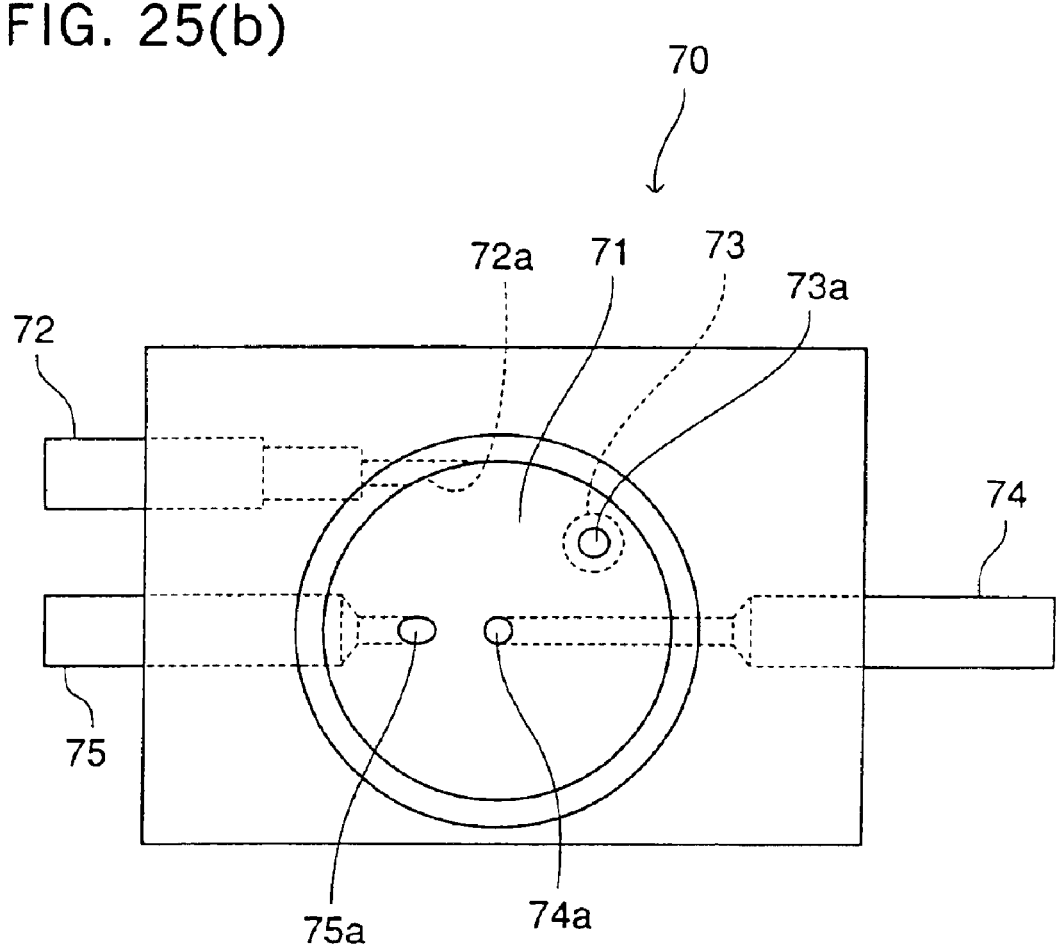

FIGS. 25(a) and 25(b) are a vertical sectional view and a plan view, respectively, of the mixing chamber 70. The mixing chamber 70 includes a container portion 71 for mixing the blood sample. The container portion 71 has a cylindrical shape with its top open to the atmosphere. A diluent supplying nipple 72 is provided in an upper portion of the container portion 71. A nipple 73 for discharging a liquid mixture, a nipple 74 for draining residual liquid from the container portion 71, and a nipple 75 for injecting air bubbles (air) for agitating the liquid in the container portion 71 are provided in the bottom of the container chamber 71.

The nipples 72, 73, 74, 75 are respectively connected to a liquid supply port 72a, liquid discharge ports 73a, 74a, and an air supply port 75a, which communicate with the container portion 71. The liquid supply port 72a opens so as to supply the liquid from the upper portion along the inner circumferential surface of the container portion 71. Where the diluent is supplied into the mixing chamber 70 as will be described later for cleaning the chamber, the interior surface of the container portion 71 is efficiently cleaned with the diluent ejected from the liquid supply port 72a.

The mixing chamber 70 is produced by injection-molding a thermoplastic resin such as a polyether amide having a chemical resistance. The interior surface of the container portion 71 has been roughened to an arithmetic average surface roughness Ra of 0.29 μm so as to be imparted with a sufficiently high wettability with respect to the diluent. Therefore, the diluent injected from the liquid supply port 72a is supplied into the bottom of the container portion 71 without residing as liquid drops on the interior surface, so that the blood sample preliminarily supplied can accurately be diluted predetermined times.

Constructions and Operations of Pipette and Cleaner (Pipette Cleaning Device)

Figure 38:
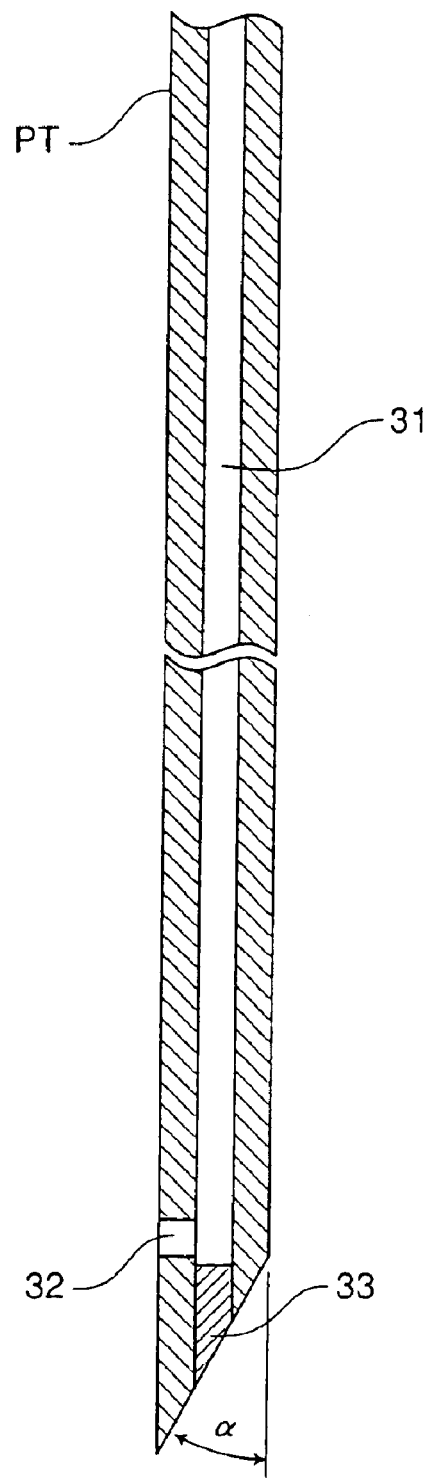
FIG. 38 is a vertical sectional view of the pipette according to this invention.

FIG. 38 is a vertical sectional view of the pipette PT. The pipette PT is a stainless steel pipe, which has a suction flow path 31 coaxially extending therein, and a distal tip sharply cut at an angle α of 30 degrees. Where the sample vessel SP1 with the cap is employed, the cap is pierced with the distal tip. A distal end of the suction flow path 31 is sealed with a stainless steel seal 33, and a suction port 32 is open in a side wall of the pipette PT with its axis extending perpendicularly to the axis of the pipette PT.

Figure 26:
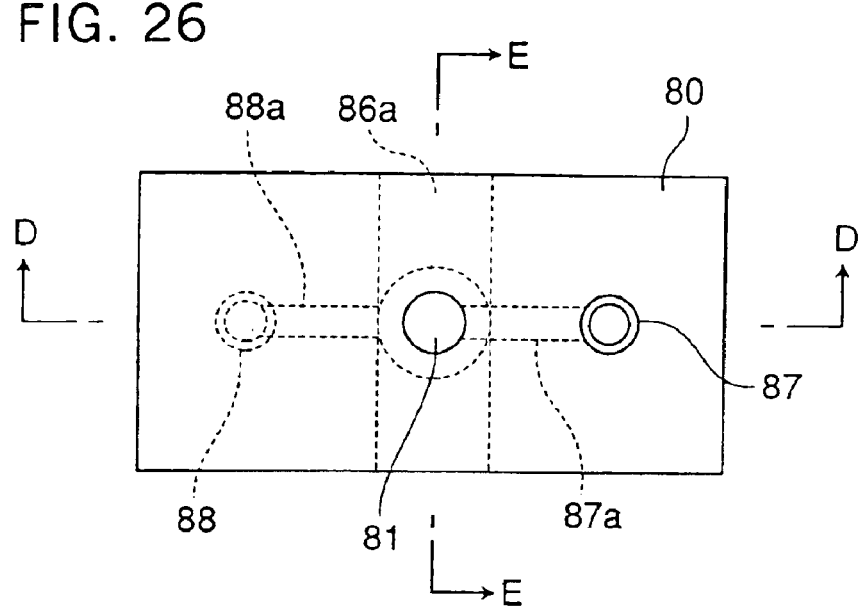
FIG. 26 is a plan view of a cleaner body according to this invention.
Figure 27:
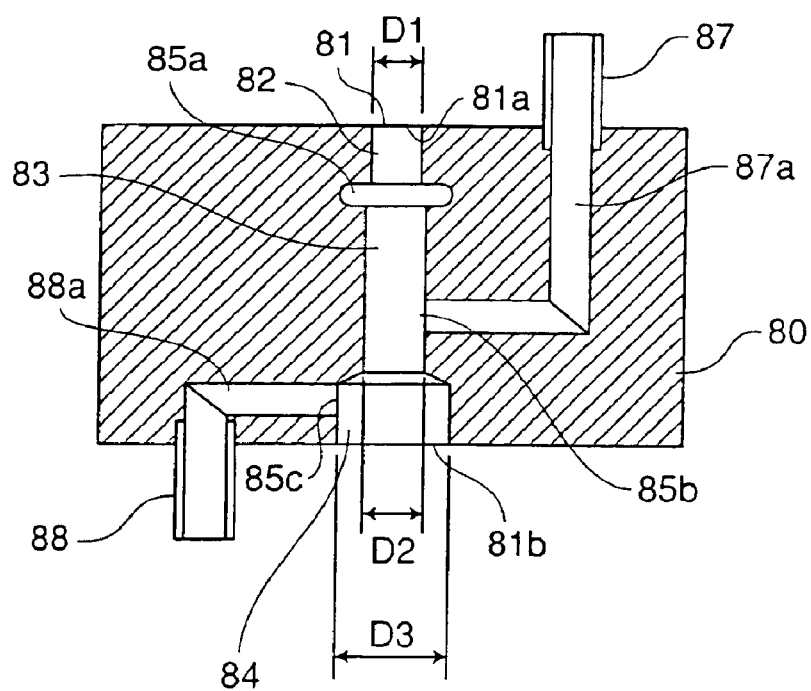
FIG. 27 is a view from a D—D arrow direction in FIG. 26.
Figure 32:
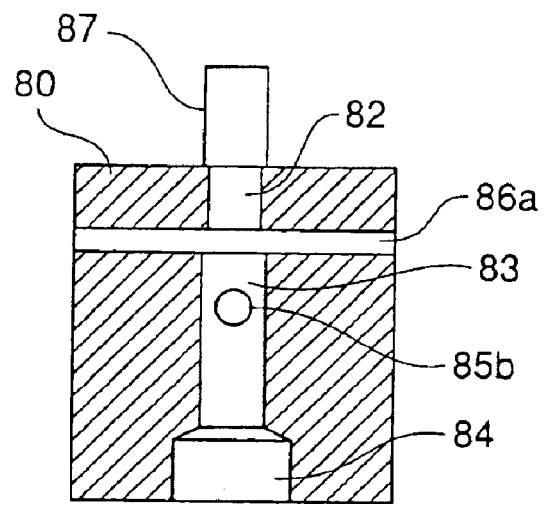
FIG. 32 is a view from an E—E arrow direction in FIG. 26.

FIG. 26 is a plan view of the cleaner body 80. FIGS. 27 and 32 are views from a D—D arrow direction and from an E—E arrow direction, respectively. As shown, a cleaner body 80 has a pipette through-hole 81 centrally extending therethrough, so that the pipette PT is vertically inserted in the pipette through-hole 81 from an inlet 81a to an outlet 81b. The pipette through-hole 81 has a round cross section.

The pipette through-hole 81 includes a pipette guide hole 82, a first through-hole 83 and a second through-hole 84 serially and coaxially disposed in this order from the inlet 81a to the outlet 81b. The pipette guide hole 82 has an inner diameter slightly greater than the outer diameter of the pipette PT, and serves to guide the pipette PT so as to align the axis of the pipette PT with the axes of the first and second through-holes 83, 84.

On the other hand, the first and second through-holes 83, 84 constitute a pipette cleaning hole for cleaning the pipette. A first opening 85a and a second opening 85b are formed in the interior surface of the first through-hole 83 on an inlet side and on an outlet side, respectively. A third opening 85c is formed in the interior surface of the second through-hole 84.

The cleaner body 80 includes a vent path 86a for opening the first opening 85a to the atmosphere (to the outside of the cleaner body 80), a cleaning liquid drain path 87a allowing communication between the second opening 85b and a cleaning liquid draining nipple 87, and a cleaning liquid supply path 88a allowing communication between the third opening 85c and a cleaning liquid supplying nipple 88.

The pipette guide hole 82, the first through-hole 83 and the second through-hole 84 respectively have inner diameters D1, D2 and D3 which are set at 105%, 115% and 200% of the outer diameter of the pipette PT. Where the pipette PT has an outer diameter of 2.0 mm, for example, D1=2.1 mm, D2=2.3 mm and D3=4.0 mm.

Figure 34:
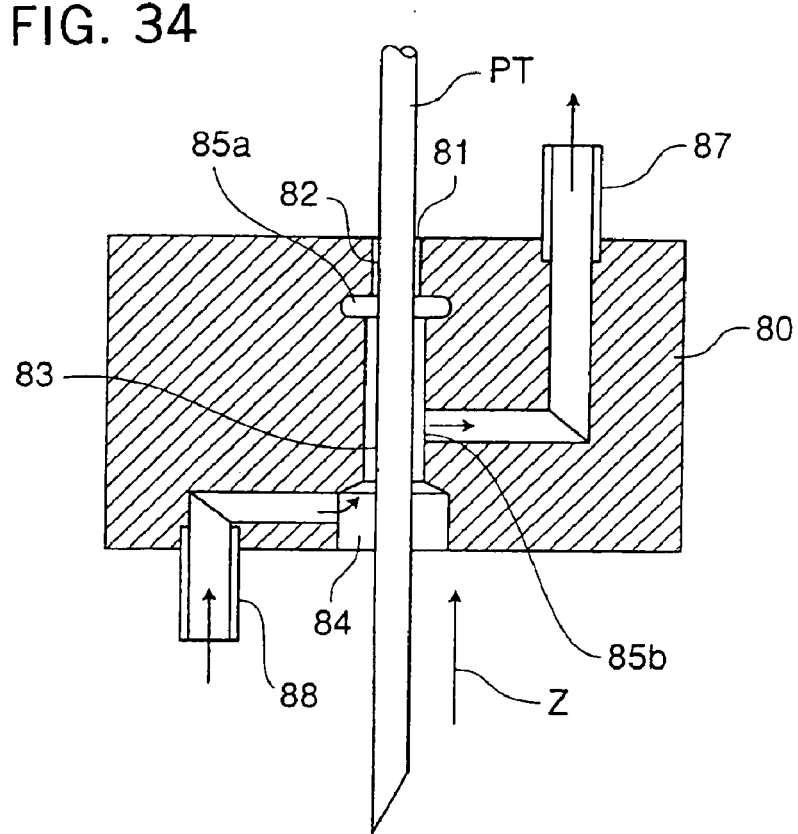
FIG. 34 is a diagram for explaining the operation of the cleaner body shown in FIG. 27.

When the cleaning liquid (the diluent in this embodiment) is supplied from the nipple 88 into the second through-hole 84 and sucked from the nipple 87 with the pipette PT extending from the upper side to the lower side through the pipette through-hole 81 as shown in FIG. 34, the cleaning liquid flows in uniform contact with the exterior of the pipette PT from the second through-hole 84 into the first through-hole 83, and drained from the nipple 87.

Therefore, when the pipette PT is moved up in the arrow direction Z in this state, the blood sample and the like adhering on the exterior (outer circumferential surface) of the pipette PT is washed away with the cleaning liquid and drained.

At this time, a part of the cleaning liquid adheres on the pipette PT, and is moved upper than the second opening 85b as the pipette PT is moved up. Accordingly, there would be a possibility that the cleaning liquid remains in an upper portion of the first through-hole 83. However, the upper portion of the first through-hole 83 is kept at the atmospheric pressure by the effect of the first opening 85a provided in the first through-hole 83, so that the cleaning liquid is sucked back into the second opening 85b by a pressure difference between the first opening 85a and the second opening 85b, and drained into the nipple 87 through the second opening 85b. Therefore, the cleaning liquid flowing into the first through-hole 83 from the second through-hole 84 does not remain in the upper portion of the first through-hole 83. Thus, the exterior of the pipette PT can effectively be cleaned.

Figure 36:
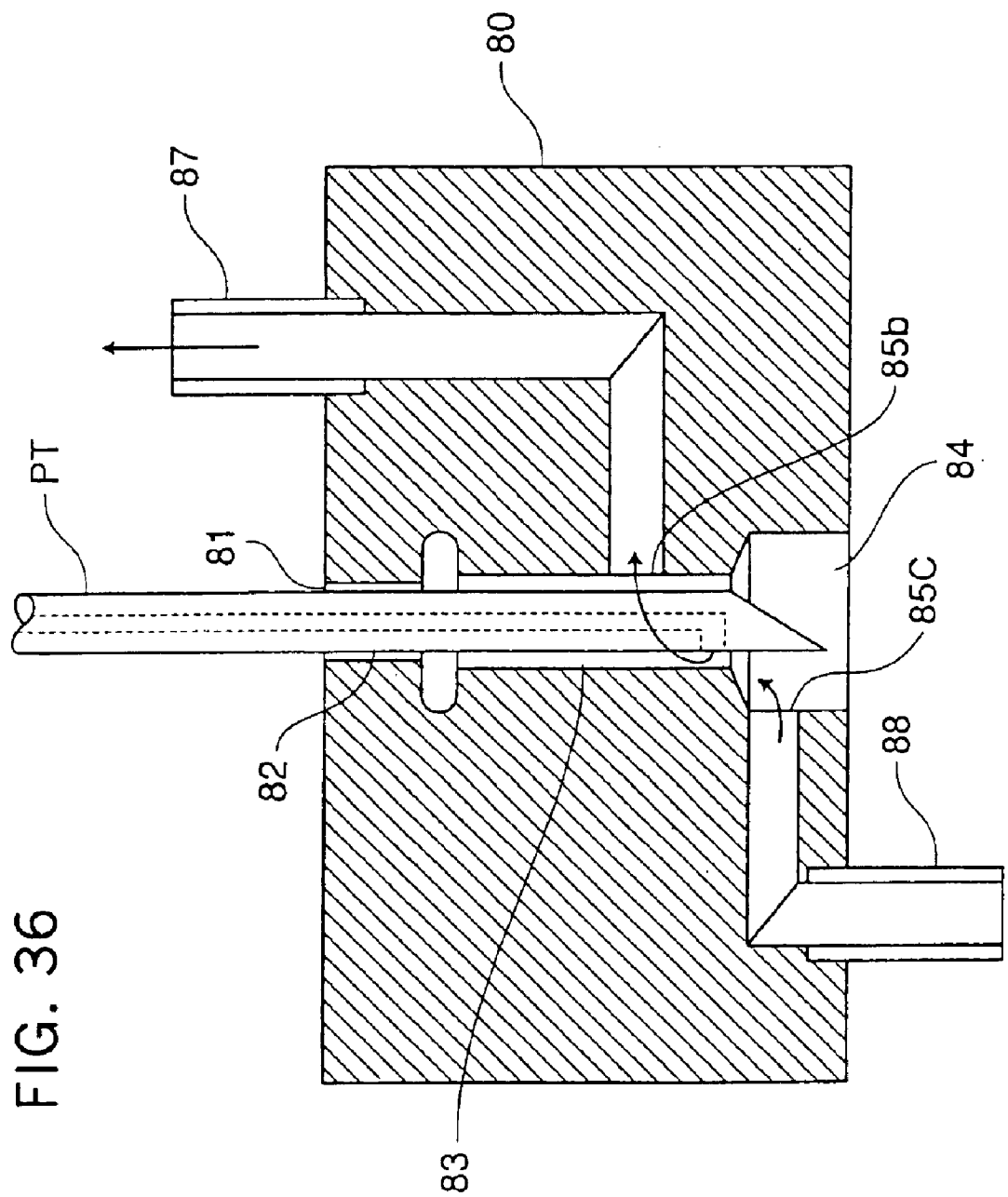
FIG. 36 is a diagram for explaining the operation of the cleaner body shown in FIG. 27.

When the cleaning liquid is supplied from the proximal end of the pipette PT to the distal suction port 32 with the tip of the pipette PT kept within the first through-hole 83 and with a negative pressure being applied from the nipple 87 as shown in FIG. 36, the cleaning liquid having passed through the suction flow path 31 of the pipette PT is drained from the suction port 32 of the pipette PT, and sucked into the nipple 87 through the second opening 85b but not drained into the second through-hole 84. Thus, the interior of the pipette PT (i.e., the inner surfaces of the suction flow path 31 and the suction port 32 of the pipette PT) is cleaned.

Figure 37:
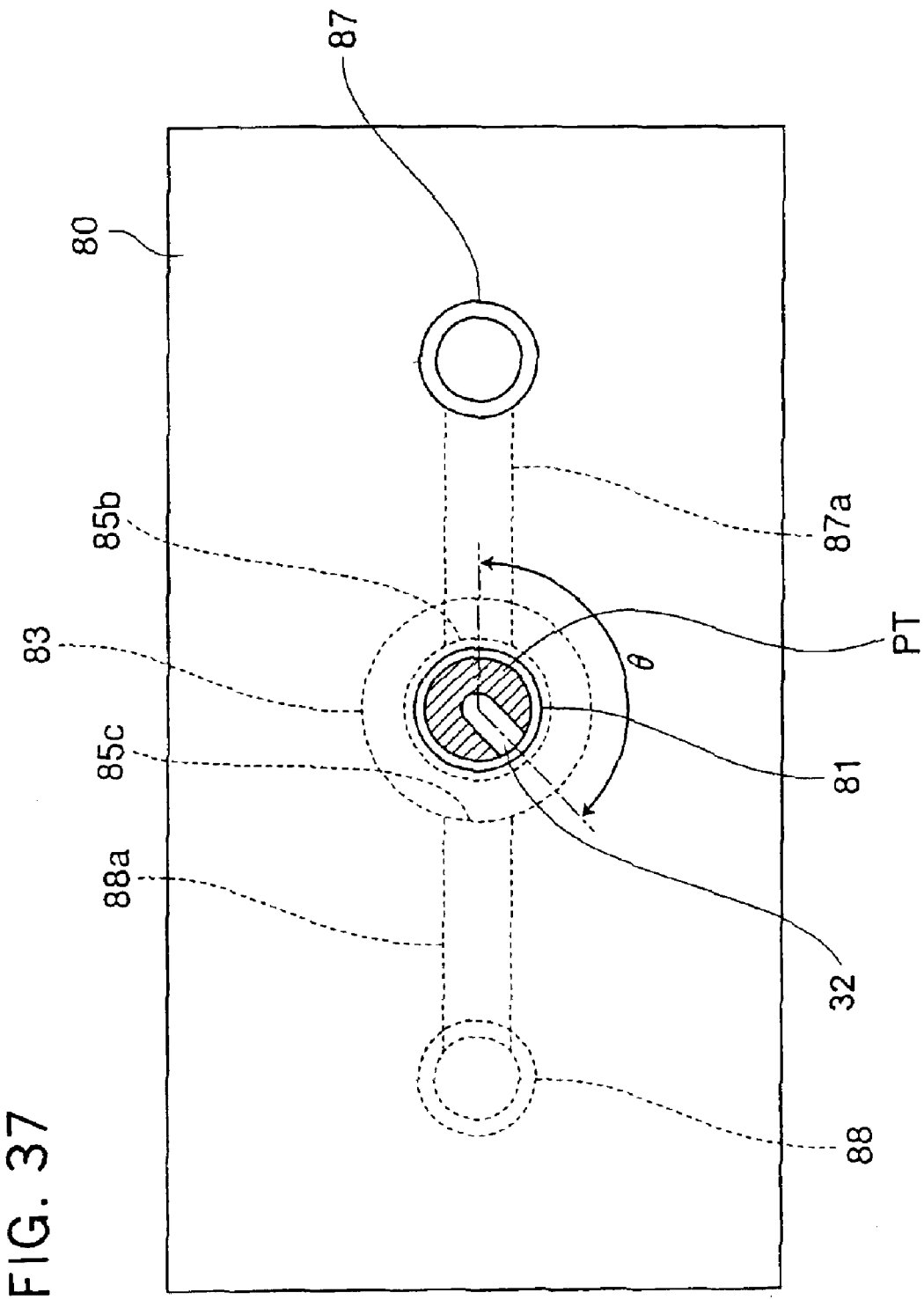
FIG. 37 is a diagram for explaining a positional relationship between a pipette and the cleaner body shown in FIG. 26.

A positional relationship between the cleaner body 80 and the pipette PT as seen axially of the pipette PT is shown in FIG. 37. As shown, the pipette PT is positioned with respect to the cleaner body 80 with the axis of the suction port 32 and the axis of the opening 85b of the cleaning liquid drain path 87a forming an angle θ of greater than 90 degrees. This is because the following phenomena have experimentally been observed.

(1) If θ≦90 degrees, the diluent (to be described later) filled in the suction flow path 31 and the suction port 32 of the pipette PT is sucked out by the negative pressure in the cleaning liquid drain path 87a and a void occurs in the suction port when the exterior or interior of the pipette PT is cleaned. Therefore, the blood sample is introduced into the void in the suction port 32 before the blood sample is sucked to be quantified by means of the pipette PT. Accordingly, the blood sample is sucked into the pipette PT in an amount greater by the previously introduced amount than an intended amount, resulting in erroneous quantifying.

(2) If θ>90 degrees, the negative pressure in the cleaning liquid drain path 87a exerts no direct effect on the suction port 32. Therefore, accurate quantifying can be ensured because no void occurs in the suction port 32 when the exterior or interior of the pipette PT is cleaned.

Figure 33:
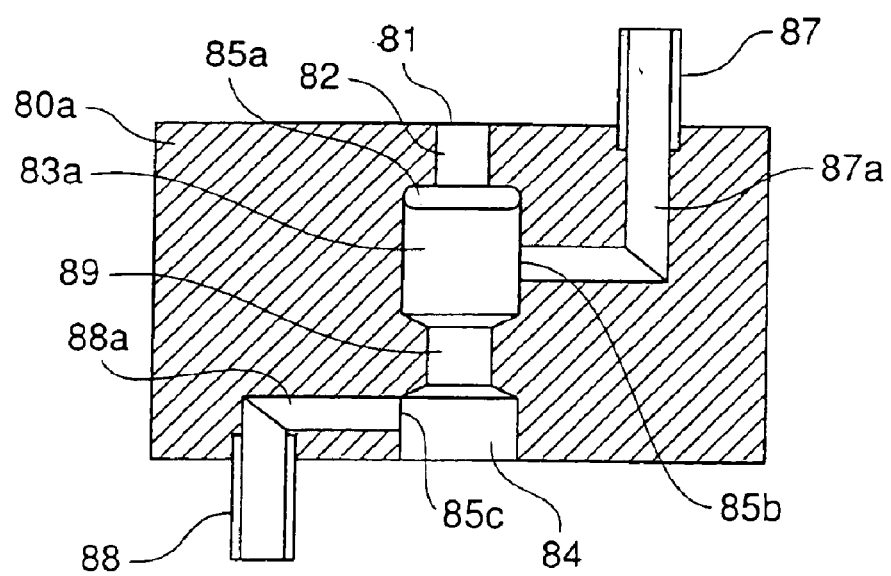
FIG. 33 is a diagram illustrating a modification of the cleaner body corresponding to FIG. 27.

FIG. 33 is a diagram illustrating the construction of a cleaner body 80a as a modification of the cleaner body 80 corresponding to FIG. 27.

The cleaner body 80a has a pipette through-hole 81 which includes a pipette guide hole 82, and first, second and third through-holes 83a, 89, 84 serially and coaxially provided in this order from an inlet to an outlet.

That is, the first and second through-holes 83a, 89 correspond to the first through-hole 83 in FIG. 27, and the third through-hole 84 corresponds to the second through-hole 84 in FIG. 27. As shown in FIG. 33, the second through-hole 89 has substantially the same inner diameter as the pipette guide hole 82, and the first through-hole 83a has an inner diameter which is greater than that of the second through-hole 89 and substantially equal to that of the third through-hole 84.

Otherwise, the cleaner body 80 a has substantially the same construction as the cleaner body 80 (FIG. 27), and the pipette PT can be cleaned in the cleaner body 80a in the same manner as in the cleaner body 80.

Another Exemplary Pipette

Figure 39:
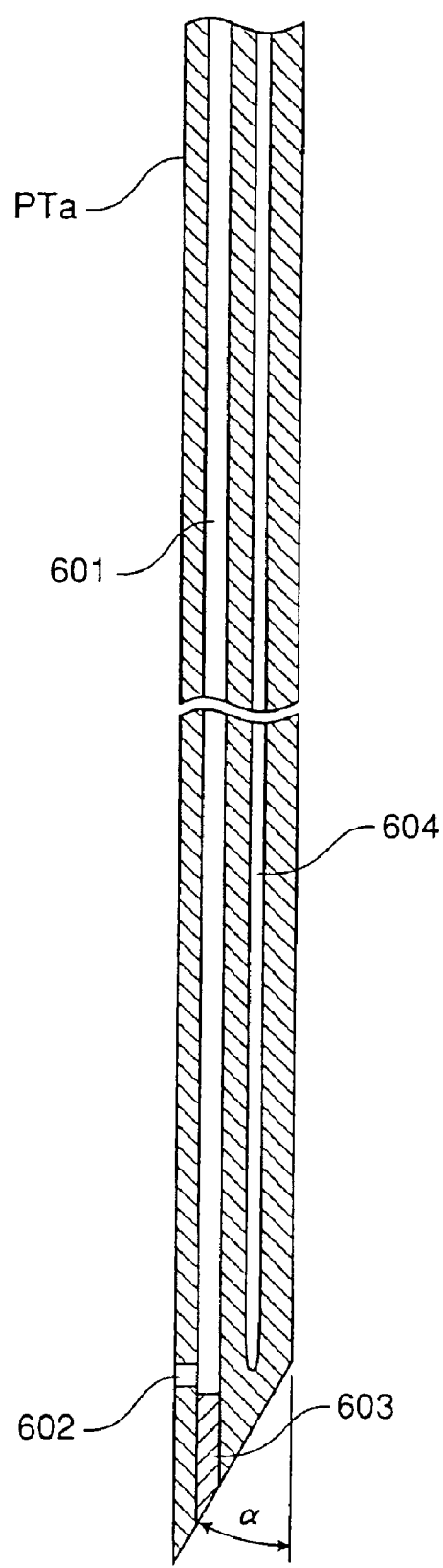
FIG. 39 is a vertical sectional view illustrating another exemplary pipette according to this invention.
Figure 40:
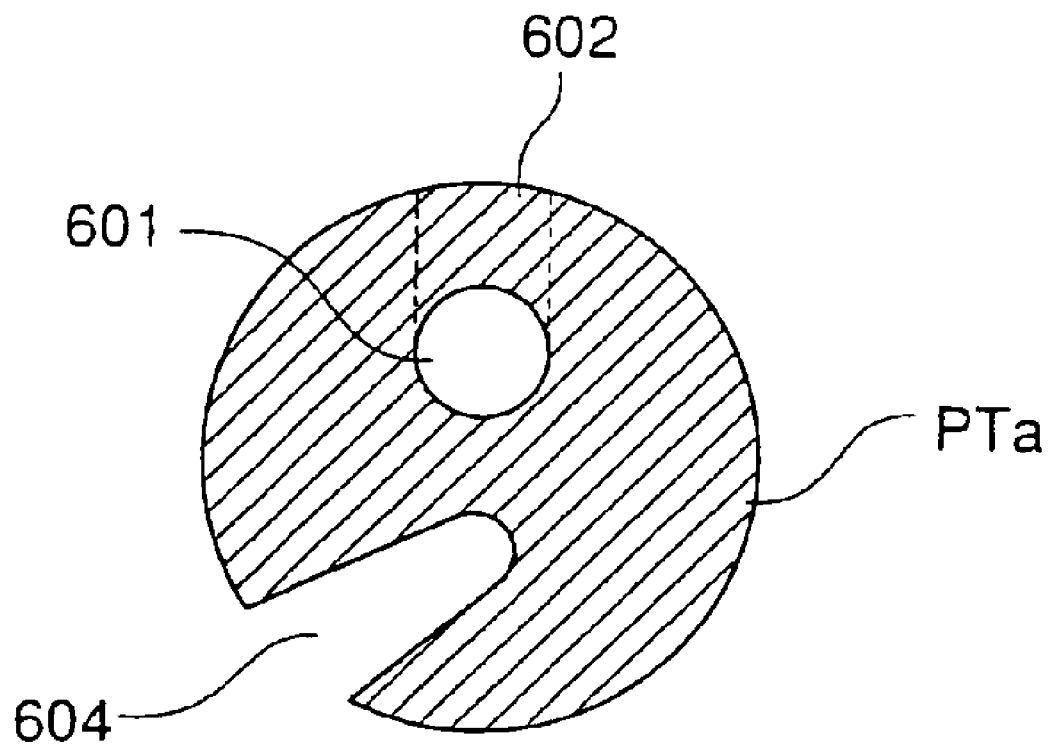
FIG. 40 is a cross sectional view of the pipette shown in FIG. 39.

FIG. 39 is a vertical sectional view illustrating another exemplary pipette PTa to be employed instead of the pipette PT (FIG. 38) where a vacuum blood sampling tube (sealed with a rubber cap) is used as the sample vessel SP1 or SP2, and FIG. 40 is a cross sectional view of the pipette PTa.

As shown, the pipette PTa is a stainless steel pipe, which has a suction flow path (fluid path) 601 extending therein in parallel and offset relation with respect to the axis thereof, and a distal tip sharply cut at an angle α of 30 degrees, so that the cap of the sample vessel SP1 or SP2 can be pierced with the distal tip. A distal end portion of the suction flow path 601 is sealed with a stainless steel seal 603. The pipette PTa has a suction port 602 open in a side wall thereof. The suction port 602 has an axis extending perpendicularly to the axis of the pipette PTa, and communicates with the suction flow path 601.

The pipette PTa has a groove 604 provided in an outer surface thereof as extending parallel to the axis thereof. The groove 604 serves to let the internal pressure of the sample vessel back to the atmospheric pressure immediately after the cap is pierced with the pipette PTa. This ensures smooth sucking operation of the pipette PTa and improves the quantifying accuracy. The groove 604 has a generally U-shaped cross section having a wider width toward the outer periphery of the pipette and a round bottom. With such a cross section, the groove 604 is free from clogging with rubber scum and blood, and efficiently cleaned in the cleaner (FIG. 27).

Since the axis of the suction flow path 601 is offset from the axis of the pipette PTa, the groove 604 can be formed in a greater cross section. Therefore, the cross sectional area and configuration of the groove 604 can more flexibly be determined for higher efficiency.

FIGS. 41(a) to 41(e) are diagrams for explaining a process for producing the pipette PTa shown in FIG. 39.

Figure 41A:
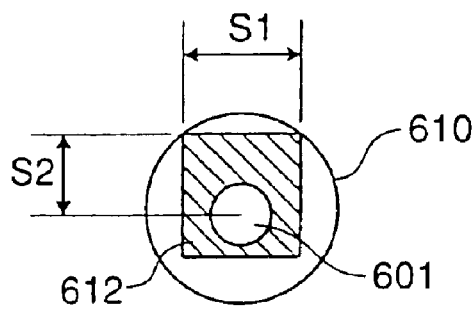
FIGS. 41(a) to 41(e) are diagrams for explaining a process for producing the pipette shown in FIG. 39.

First, a commercially available pipe 610 of stainless steel (SUS316) having an outer diameter of 1.6 mm and an inner diameter of 0.5 mm is cut into a square block 612 having a square cross section with an edge length S1 of 1 mm and with a hole 601 spaced by a distance S2 of 0.65 mm from an edge thereof as shown in FIG. 41(a).

Figure 41B:
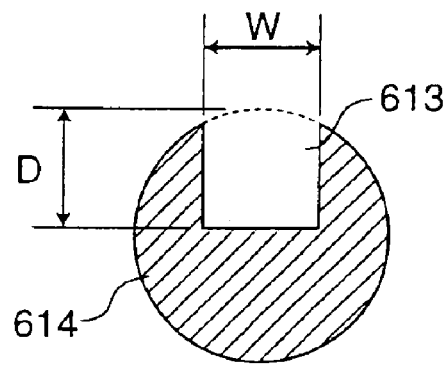

Then, as shown in FIG. 41(b), a trench 614 having a width W of 1 mm and a depth D of 1 mm is formed axially in a commercially available round rod 613 of stainless steel (SUS316) having an outer diameter of 2.1 mm.

Figure 41C:
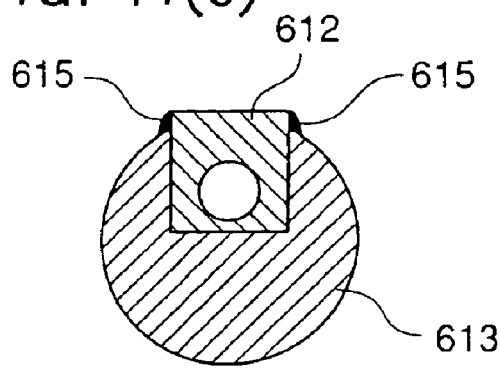

Subsequently, as shown in FIG. 41(c), the square block 612 is fitted in the trench 614 of the round rod 613, and boundaries 615 between the square block 612 and the round rod 613 are laser-welded to combine the square block 612 and the round rod 613.

Figure 41D:
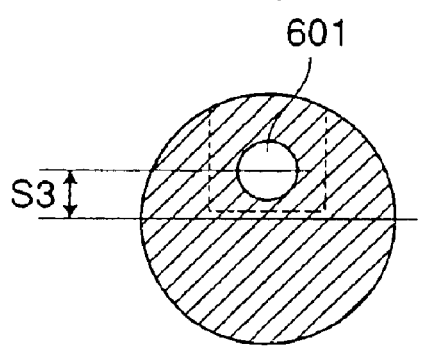

Then, projecting surface portions of the square block is polished away to provide a round pipe having an outer diameter of 2.1 mm with the hole 601 offset by a distance S3 of 0.4 mm from the axis of the pipe as shown in FIG. 41(d).

Figure 41E:
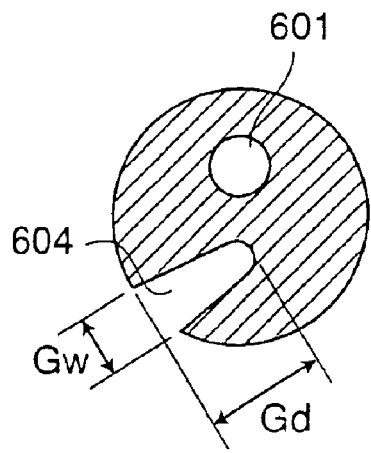

In turn, a U-shaped groove 604 having a maximum width GW of 0.5 mm and a depth Gd of 1 mm is formed in the round pipe by milling as shown in FIG. 41(e). The cross sectional configuration and position of the groove 604 are determined so as to ensure the most effective ventilation and the most efficient cleaning of the groove 604.

Then, an end of the round pipe is cut at an angle α of 30 degrees, and an end of the hole 601 is sealed with a stainless seal 603 by way of welding or silver alloy brazing as shown in FIG. 39. Thereafter, a suction port 602 is formed in a side wall of the round pipe.

Thus, the pipette PTa is produced.

Construction and Operation of Negative Pressure Pump

Figure 28:
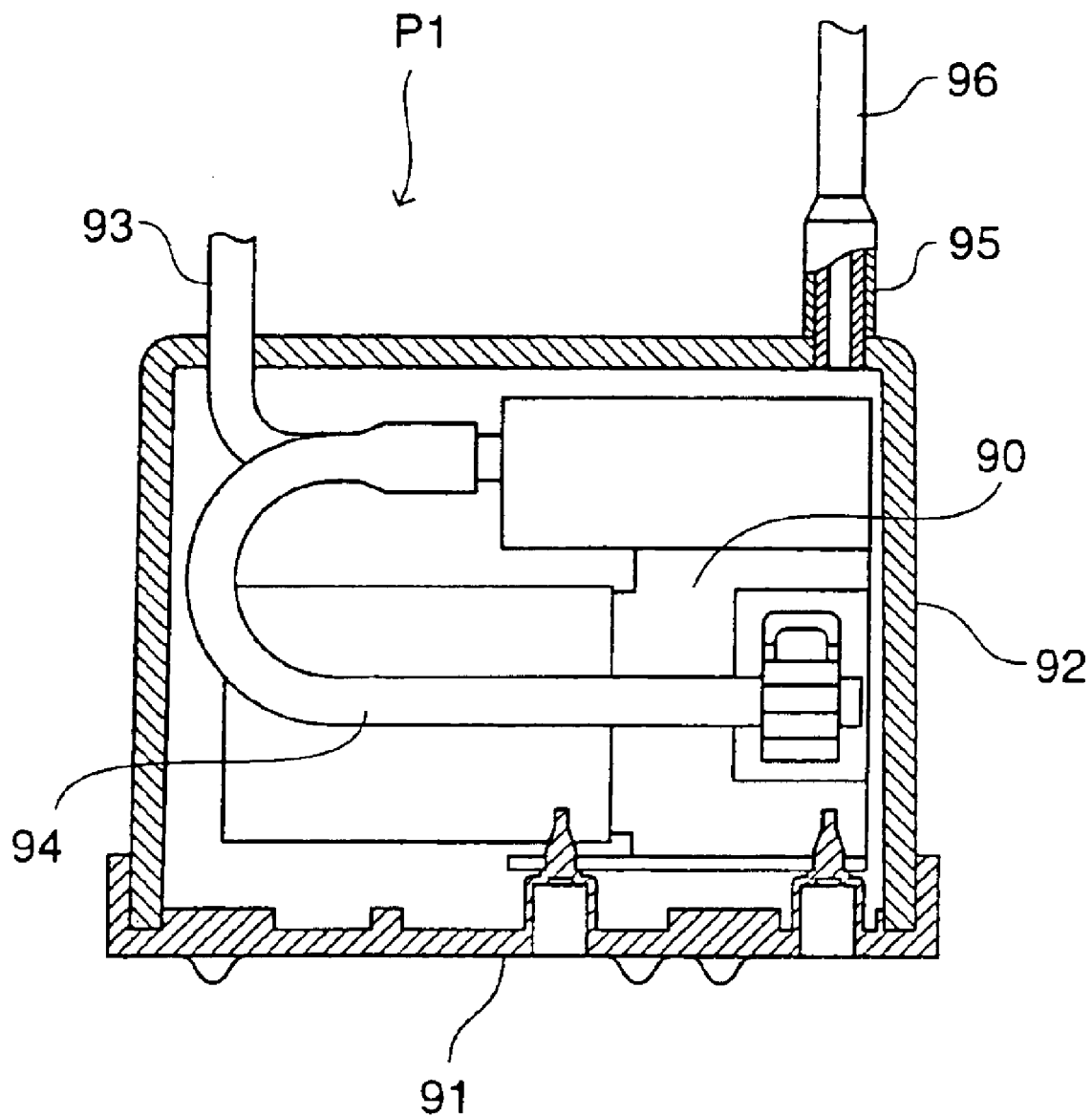
FIG. 28 is a sectional view of a negative pressure pump according to this invention.

FIG. 28 is a partly cut-away front view illustrating the construction of a negative pressure pump P1 (to be describe later) provided in the flow control section 8 (FIG. 1). An air pump 90 is mounted on a rubber base seat 91 and enclosed by a resin case 92. A suction tube 93 of the air pump 90 extends to the outside through an upper through-hole of the case 92, and an open end of an exhaust tube 94 of the air pump 90 is fixed in the case 92. A nipple 95 is fitted in another upper through-hole of the case 92, and a silencer exhaust tube 96 is connected to the nipple 95.

With this arrangement, vibrations of the air pump 90 are absorbed by the rubber base seat 91, and noises of the air pump 90 are insulated by the enclosure case 90. Exhaust noises are silenced by the silencer exhaust tube 96. Thus, the efficient noise reduction of the negative pressure pump P1 can be achieved. The inner diameter and length of the tube 96 are properly determined on the basis of an experiment performed for examination of a silencing effect. In this embodiment, a DC air pump having a rated voltage of DC 12V and a rated air output of 2 L/min is employed as the air pump 90, and a silicone tube having an outer diameter of 6.5 mm, an inner diameter of 3 mm and a length of 300 mm is employed as the tube 96.

Constructions of Fluid Circuit and Electrical Circuit

Figure 29:
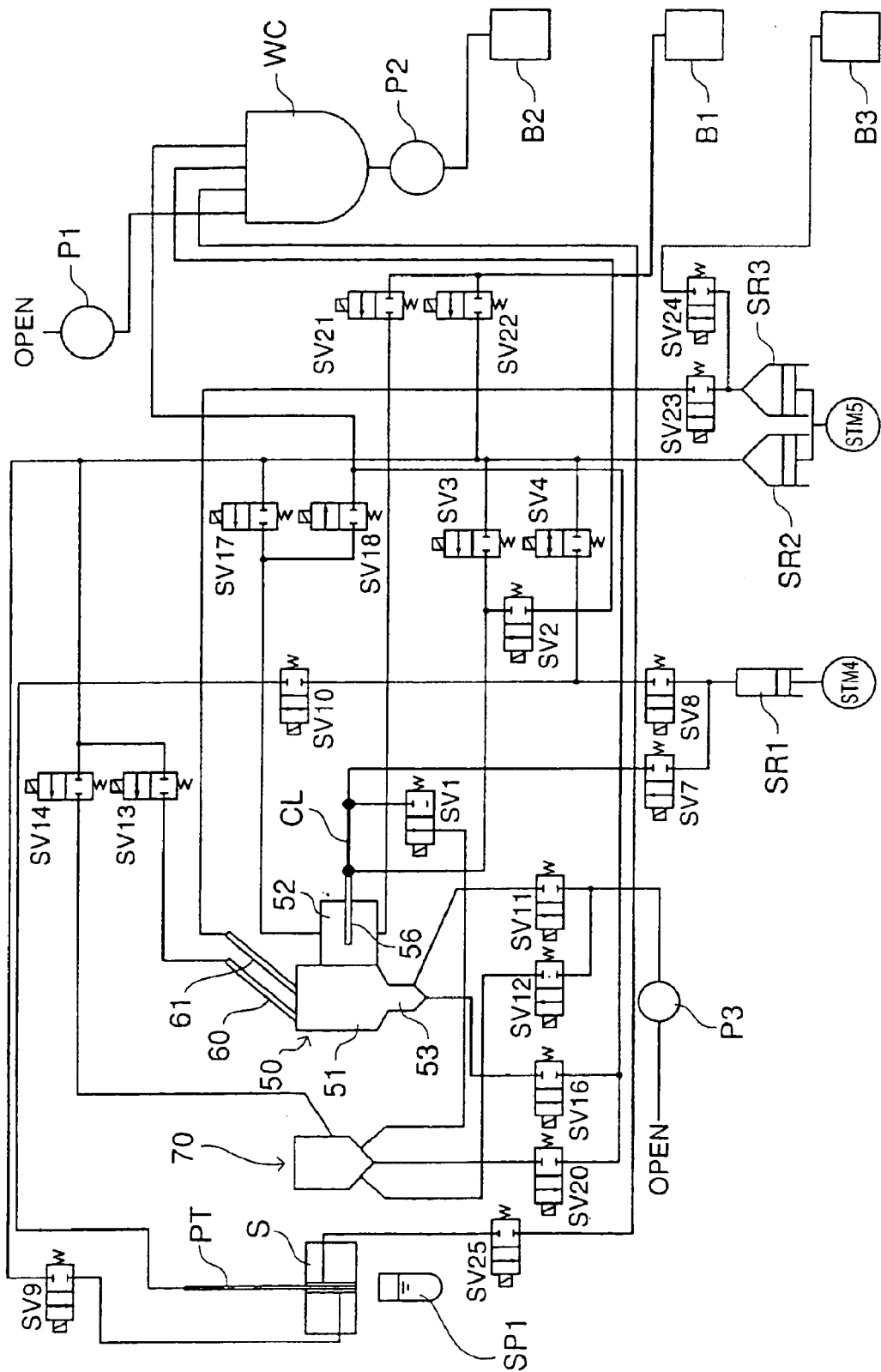
FIG. 29 is a system diagram of a fluid circuit of the blood analyzer according to this invention.

FIG. 29 is a system diagram illustrating a fluid circuit according to the embodiment of the invention. In the fluid circuit, fluid devices are connected by fluid supply tubes. The fluid circuit includes a syringe pump SR1 for quantitatively dispensing the sample from the pipette PT, a syringe pump SR2 for supplying the diluent into the mixing chamber 70 and the detector 50 from the diluent container B1, a syringe pump SR3 for supplying the hemolyzing agent into the detector 50 from the hemolyzing agent container B3, a waste liquid chamber WC for storing the waste liquid drained from the mixing chamber 70 and the detector 50, the negative pressure pump P1 for applying a negative pressure to the waste liquid chamber WC, a liquid draining pump P2 for draining the waste liquid from the waste liquid chamber WC to the waste liquid container B2, an air pump P3 for supplying air into the mixing chamber 70 and the detector 50 for agitation, and electromagnetic valves SV1 to SV4, SV7 to SV14, SV16, SV17 and SV20 to SV25 for opening and closing flow paths in the fluid circuit. The syringe pump SR1 is driven by a syringe pump motor STM4, and the syringe pumps SR2, SR3 are driven by a syringe pump motor STM5. Stepping motors may be employed as the syringe motors STM4, STM5.

A preferred example of the diluent is CELLPACK available from Sysmex Corporation, and a preferred example of the hemolyzing agent is STROMATOLYSER WH available from Sysmex Corporation.

Figure 30:
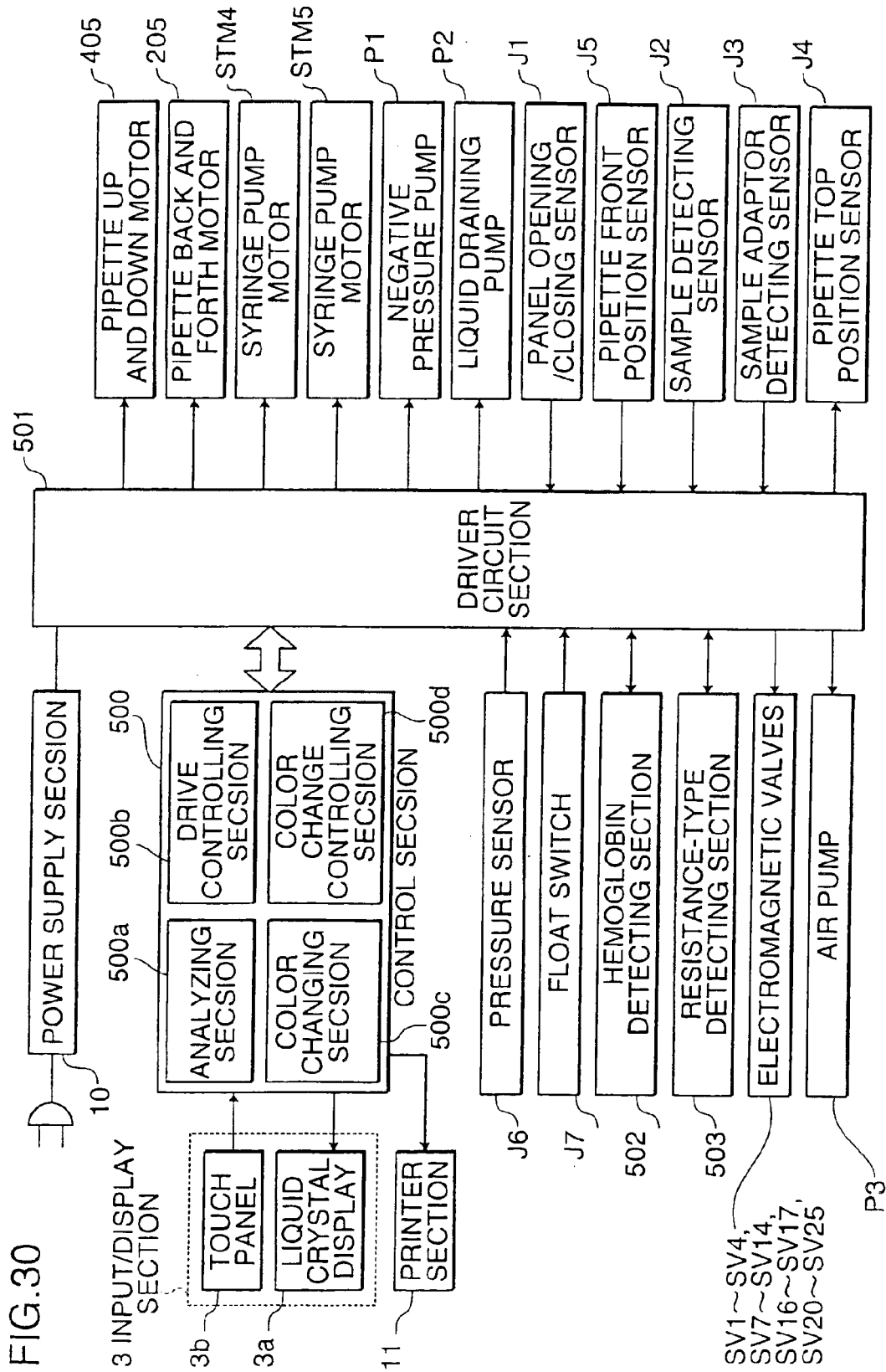
FIG. 30 is a block diagram illustrating an electrical circuit of the blood analyzer according to this invention.

FIG. 30 is a block diagram illustrating the electrical circuit according to the embodiment of the invention. The power supply section 10 transforms a voltage supplied from a commercial AC power supply into a DC voltage (12V), which is supplied to the control section 500 and the driver circuit section 501. The control section 500 is comprised of a microprocessor including a CPU, a ROM and a RAM, and the driver circuit section 501 includes driver circuits and I/O ports. The input/display section 3 includes a liquid crystal display 3a and a transparent touch panel 3b superposed on the liquid crystal display 3a, and is connected to the control section 500.

The driver circuit section 501 performs A-D conversion on output signals of the panel opening/closing sensor J1, the sample detecting sensor J2, the sample adaptor detecting sensor J3, the pipette top position sensor J4, the pipette front position sensor J5, a pressure sensor J6 for detecting the negative pressure in the waste liquid chamber WC, a float switch J7 for detecting a liquid amount accumulated in the waste liquid chamber WC, a hemoglobin detecting section 502 constituted by the light emitting diode 68 and the photodiode 69, and a resistance-type detecting section 503 constituted by the electrodes 58, 67, and outputs converted signals to the control section 500.

The control section 500 includes an analyzing section 500a which analyzes the sample on the basis of digital signals received from the driver circuit section 501 and output signals received from the touch panel 3b of the input/display section 3, and a drive controlling section 500b which processes the signals according to a predetermined processing program. The drive controlling section 500b causes the driver circuit section 501 to drive the pipette up and down motor 405, the pipette back and forth motor 205, the syringe pump motor STM4, the syringe pump motor STM5, the negative pressure pump P1, the liquid draining pump P2, the air pump P3 and the electromagnetic valves SV1 to SV25 on the basis of the results of the processing. The control section 500 controls the liquid crystal display 3a of the input/display section 3 and the printer section 11 to display and print out analysis conditions, analysis items, analysis results and the like. The control section 500 further includes a color changing section 500c for changing a display color on the liquid crystal display 3a and a color change controlling section 500d for controlling the color changing section 500c as will be described later.

Analytic Operation to be Performed by Blood Analyzer

An analytic operation to be performed by the blood analyzer shown in FIG. 1 will hereinafter be described with reference to a flow chart shown in FIGS. 31(a) and 31(b).

Figure 31A:
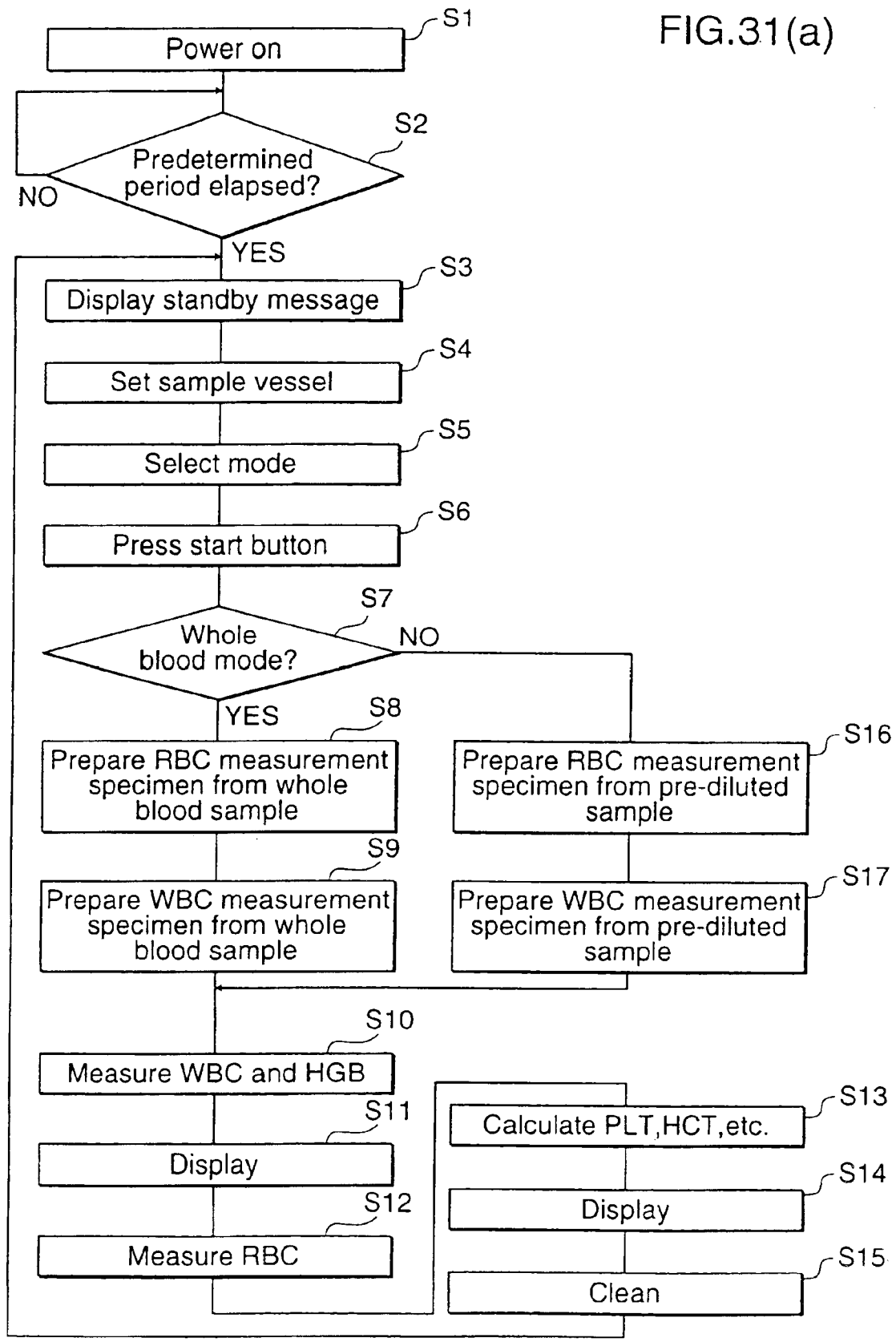
FIGS. 31(a) and 31(b) are flow charts for explaining the operation of the blood analyzer according to this invention.
Figure 31B:
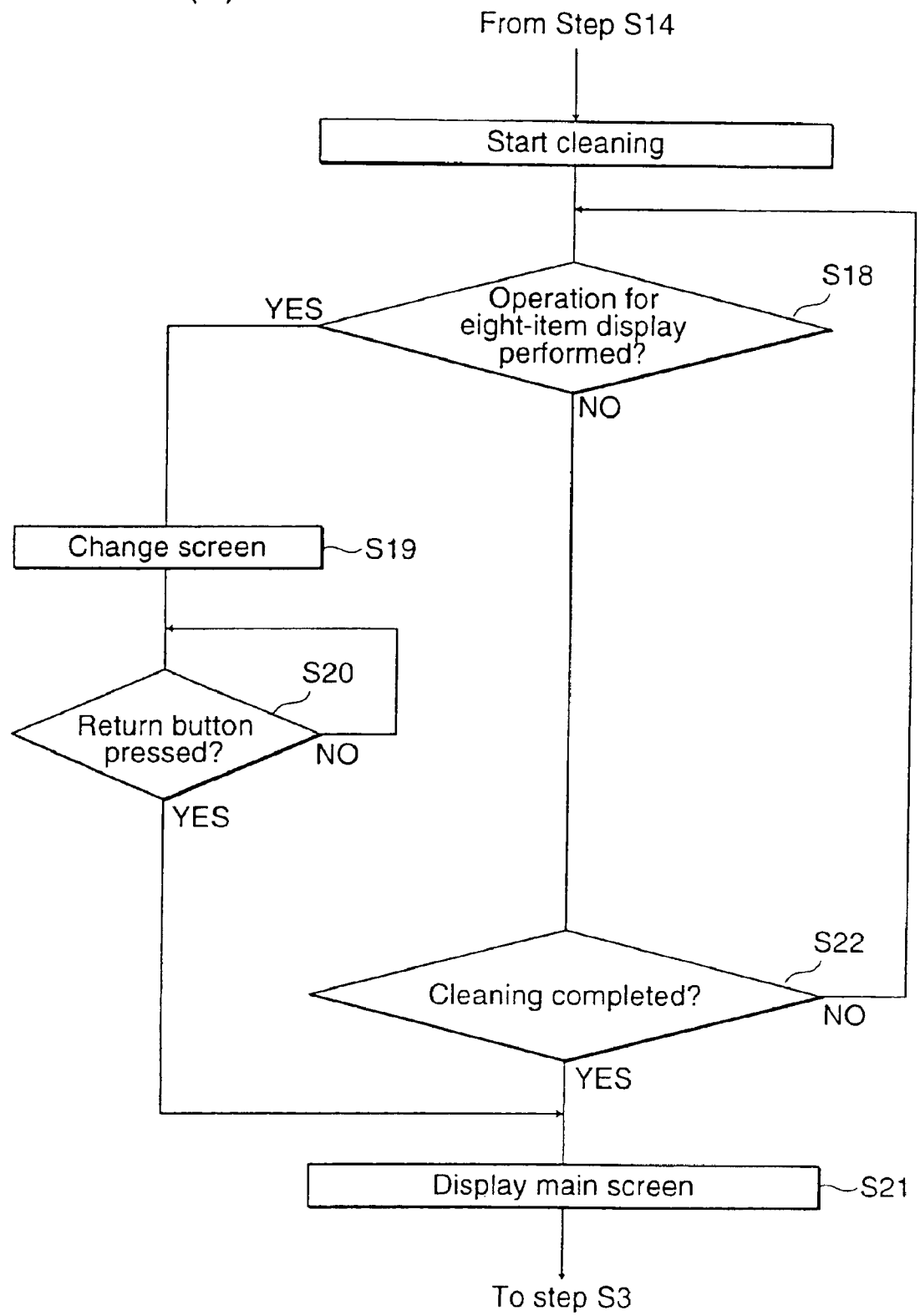

As shown in FIG. 31(a), the power supply to the blood analyzer is turned on (Step S1). When a measurement preparation period required for preparatory operations for the analysis including a preliminary cleaning operation is elapsed (Step S2), a message "Ready" is displayed on the liquid crystal display 3a of the input/display section 3. Then, the user sets a sample vessel in the sample setting section 6 (FIG. 4) (Step S4). Where a sample in the sample vessel thus set is a whole blood sample, the user selects a whole blood mode by means of the touch panel 3b of the display section 3 and, where the sample is a diluted sample, the user selects a pre-diluted mode (Step S5).

Then, the user presses a start button on the touch panel 3b (Step S6). Where the sample vessel SP1 or SP2 is not set and/or the sample setting panel 4 is not closed in Step S4, the sensors J1, J2 detect such a situation, so that the analyzer does not operate. Where the sample vessel SP1 or SP2 is set and the sample setting panel 4 is closed, the analyzer starts operating. Where the whole blood mode is selected (Step S7), a specimen for measurement of the number of red blood cells (RBC) and a specimen for measurement of the number of white blood cells (WBC) are prepared from the whole blood sample (Step S8, S9).

With the use of the WBC measurement specimen prepared in Step S9, measurement of the WBC and the amount of hemoglobin (HGB) is performed (Step S10), and then the measured WBC and HGB are displayed on the liquid crystal display 3a (Step S11). Subsequently, measurement of the RBC is performed with the use of the RBC measurement specimen prepared in step S8, and the number of platelets (PLT), a hematocrit value (HCT) and other analysis items including a mean corpuscular volume (MCV), a mean corpuscular hemoglobin (MCH) and a mean corpuscular hemoglobin concentration (MCHC) are calculated. Then, the measured RBC and the calculated values for the respective analysis items are displayed on the liquid crystal display (Steps S13, S14).

The WBC, the RBC and the PLT are determined by counting pulses indicative of changes in impedance between the electrodes 58 and 67 of the detector 50. The HGB is determined by comparing the absorbance (blank level) of the diluent alone and the absorbance of the WBC measurement specimen measured by the photodiode 68. The HCT is determined on the basis of a maximum level of the pulses indicative of the changes in impedance between the electrodes 58 and 67, the MCV, the MCH and the MCHC are calculated from the following expressions:

$$MCV=(HCT)/(RBC)$$

$$MCH=(HGB)/(RBC)$$

$$MCHC=(HGB)/(HCT)$$

Further, the following items are also calculated.

LYM %: Ratio of small leukocytes to total WBC (They are assumed to be equivalent to lymphocytes.)

MXD %: Ratio of middle leukocytes to total WBC (They are assumed to be equivalent to monocytes, eosinophils and basophils.)

NEUT %: Ratio of large leukocytes to total WBC (They are assumed to be equivalent to neutrophils.)

LYM#: Absolute number of small leukocytes (They are assumed to be equivalent to lymphocytes.)

MXD#: Absolute number of middle leukocytes (They are assumed to be equivalent to monocytes, eosinophils and basophils.)

NEUT#: Absolute number of large leukocytes (They are assumed to be equivalent to neutrophils.)

RDW-SD: Calculated distribution width of erythrocytes, standard deviation

RDW-CV: Calculated distribution width of erythrocytes, coefficient of variation

PDW: Calculated distribution width of platelets

MPV: Mean platelet volume

P-LCR: Ratio of large platelets to the total number of platelets

Then, a fluid circuit cleaning operation is performed. Upon completion of the cleaning operation (Step S15), the routine returns to Step S3, and "Ready" is displayed on the liquid crystal display 3a on standby for the analysis of the next sample. Where the pre-diluted mode is selected in Step S7, the RBC measurement specimen and the WBC measurement specimen are prepared from a pre-diluted blood sample (Steps S16, S17). In this case, the pre-diluted sample is obtained by preliminarily diluting a whole blood sample. Therefore, a preliminary dilution factor should be taken into account so that the RBC measurement specimen and the WBC measurement specimen have the same dilution factors as those prepared from the whole blood sample in the whole blood mode.

Next, operations to be performed in Steps S8 to S15 will be described in detail with reference to the flow system diagram shown in FIG. 29. The analyzer is of a normally-closed valve type in which all the valves in the fluid circuit are usually closed.

Preliminary Cleaning Operation (Step S2)

(1) The pipette PT is moved to the upper side of the sample rack 18, and then lowered as shown in FIG. 22. (At this time, the sample vessel SP1 is not set in the sample setting section 6.)

Figure 35:
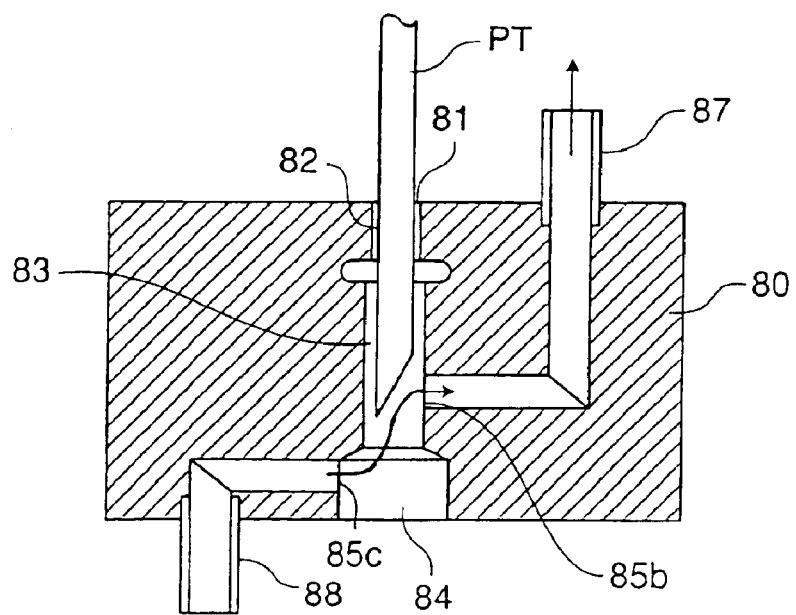
FIG. 35 is a diagram for explaining the operation of the cleaner body shown in FIG. 27.

(2) The valves SV9, SV25 are opened, and the diluent is supplied into the cleaner S from the syringe pump SR2 and then drained into the waste liquid chamber WC. At the same time, the pipette PT is lifted as shown in FIG. 34 and, when the tip of the pipette PT reaches the position shown in FIG. 35, the pipette PT is stopped. Thus, the cleaning of the exterior of the pipette PT is completed.

(3) With the valves SV9, SV25 kept open, the pipette PT is slightly lowered to the position shown in FIG. 36. Then, the valves SV4, SV10 are opened, and the diluent is supplied into the pipette PT from the syringe pump SR2. At the same time, the diluent discharged from the suction hole 32 of the pipette PT is drained into the waste liquid chamber WC for cleaning the interior of the pipette PT.

(4) When the valves SV4, SV10 are closed, the flow of the diluent from the suction port 32 of the pipette PT to the second opening 85b is stopped, whereby the interior cleaning is completed. At this time, the suction flow path 31 and the suction port 32 are filled with the diluent. On the other hand, the flow of the diluent from the third opening 85c to the second opening 85b is continued and, when the valves SV9, SV25 are closed, the flow is stopped. Therefore, the suction port 32 of the pipette PT is kept filled with the diluent.

Preparation of RBC Measurement Specimen (Step S8)

(1) A negative pressure is applied to the waste liquid chamber WC from the negative pressure pump P1, and the valves SV16, SV20 are opened, whereby residual liquid is expelled from the detector 50 and the mixing chamber 70. Thereafter, the valves SV16, SV20 are closed.

(2) The valve SV22 is opened, and the syringe pump SR2 is operated for suction, whereby the diluent is sucked into the syringe pump SR2 from the diluent container B1. Then, the valve SV22 is closed.

(3) The pipette PT is lowered to be inserted into the sample vessel SP1. Then, the valves SV10, SV8 are opened, and the syringe pump SR1 is operated for suction, whereby the pipette PT sucks a predetermined amount (10 $\mu$L) of the blood sample. Thereafter, the valves SV10, SV8 are closed.

(4) Then, the pipette PT is lifted. During the lifting, the valves SV9, SV25 are opened, whereby the diluent is supplied into the cleaner S from the syringe pump SR2 and drained into the waste liquid chamber WC for cleaning the exterior of the pipette PT. Then, the valves SV9, SV25 are closed.

(5) The valve SV14 is opened, and the syringe pump SR2 is operated for discharge, whereby a predetermined amount (1.3 mL) of the diluent is supplied into the mixing chamber 70. Then, the valve SV14 is closed.

(6) The pipette PT is moved to a position just above the mixing chamber 70, and lowered. Then, the valves SV10, SV4 are opened, and the syringe pump SR2 is operated for discharge, whereby the 10-$\mu$L blood sample preliminarily sucked into the pipette PT is discharged into the mixing chamber 70. Thus, the blood sample is diluted 130 times in the mixing chamber 70 through first-stage dilution, so that a 1.3-mL diluted sample is prepared in the mixing chamber 70. Thereafter, the valves SV10, SV4 are closed.

(7) After Steps (2) to (4) of the preliminary cleaning operation are performed, the valves SV4, SV10 are opened, and the syringe SR2 is operated for suction of a predetermined volume of air, whereby an about 10-$\mu$L air gap (air layer) is provided in the suction port 32 of the pipette PT. Thereafter, the valves SV4, SV10 are closed.

(8) The valve SV12 is opened, and the air pump P3 is driven to supply air into the mixing chamber 70, whereby the diluted sample is agitated in the mixing chamber 70 by air bubbles. Then, the air pump P3 is stopped and the valve SV12 is closed.

(9) The pipette PT is lowered again into the mixing chamber 70. Then, the valves S10, SV4 are opened, and the syringe pump SR2 is operated for suction, whereby a predetermined amount (0.59 mL) of the first-stage diluted sample is sucked into the pipette PT. Then, the valves SV10, SV4 are closed.

(10) While the exterior of the pipette PT is cleaned as in Step (2) of the preliminary cleaning operation, the pipette PT is lifted.

(11) The valve SV20 is opened. Then, a negative pressure is applied to the waste liquid chamber WC from the negative pressure pump P1, whereby the residual sample in the mixing chamber 70 is drained into the waste liquid chamber WC. Then, the valve SV20 is closed.

(12) The valve SV14 is opened, and the syringe pump SR2 is operated for discharge, whereby the diluent is supplied into the mixing chamber 70 from the syringe pump SR2. Thereafter, the valve SV14 is closed. Then, the above Step (11) is performed again. Thus, the mixing chamber 70 is cleaned.

(13) The valve SV14 is opened, and the syringe pump SR2 is operated for discharge, whereby a predetermined amount of the diluent is preliminarily dispensed in the mixing chamber 70 from the syringe pump SR2. Then, the valve SV14 is closed.

(14) The pipette PT is lowered. Then, the valves SV10, SV4 are opened, and the syringe pump SR2 is operated for discharge, whereby 0.2 mL out of the 0.59-mL first-stage diluted sample retained in the pipette PT is discharged into the mixing chamber 70. Then, the valves SV10, SV4 are closed. Thereafter, the pipette PT is lifted. During the lifting, the exterior of the pipette PT is cleaned in the aforesaid manner.

(15) The valve SV13 is opened, and the syringe pump SR2 is operated for discharge, whereby the diluent is supplied into the mixing chamber 70 from the syringe pump SR2 for diluting the sample 750 times for second-stage dilution. Thus, a second-stage diluted sample is prepared. Then, the valve SV13 is closed. At this time, the second-stage diluted sample is agitated by air bubbles in the aforesaid manner.

Thus, the RBC measurement specimen is prepared in the mixing chamber 70.

Preparation of WBC Measurement Specimen (Step S9)

(1) The valve SV13 is opened, and the syringe pump SR2 is operated for discharge, whereby 0.5 ml of the diluent is supplied into the detector 50 (preliminary dispensing). Then, the valve SV13 is closed.

(2) The pipette PT is moved to the upper side of the detector 50, and lowered. Then, the valves SV10, SV4 are opened, and the syringe pump SR2 is operated for discharge, whereby 0.39 mL of the first-stage diluted sample is discharged into the detector 50 from the pipette PT. Then, the valves SV10, SV4 are closed.

(3) The valve SV24 is opened, and the syringe pump SR3 is operated for suction, whereby the hemolyzing agent is sucked into the syringe pump SR3 from the hemolyzing agent container B3. Then, the valve SV24 is closed.

(4) The valve SV23 is opened, and the syringe pump SR3 is operated for discharge, whereby 0.5 mL of the hemolyzing agent is supplied into the detector 50. Then, the valve SV23 is closed. Thus, 0.39 mL of the diluent, 0.5 mL of the first-stage diluted sample and 0.5 mL of the hemolyzing agent are present in the first and third containers 51, 53 of the detector 50.

(5) The pipette PT is lifted, and the exterior and interior of the pipette PT are cleaned in the same manner as in Steps (2) to (4) of the preliminary cleaning operation. The suction port 32 of the pipette PT is kept filled with the diluent.

(6) The valve SV11 is opened, and the air pump P3 is operated to supply air into the detector 50 for agitation with air bubbles. Then, the air pump P3 is stopped, and the valve SV11 is closed. Thus, the preparation of the WBC measurement specimen in the detector 50 is completed.

Measurement of WBC and HGB (Step S10)

(1) The valves SV21, SV18 are opened. Then, a negative pressure is applied to the waste liquid chamber WC from the negative pressure pump P1, whereby the diluent is caused to flow from the diluent container B1 to the waste liquid chamber WC through the second container chamber 52 of the detector 50. Thus, the second container chamber 52 is cleaned, and the diluent is retained in the second container chamber 52. Then, the valves SV21, SV18 are closed.

(2) The valve SV17 is opened, and the syringe pump SR2 is operated for suction, whereby the WBC measurement specimen is caused to flow from the first and third container chambers 51, 53 into the second container chamber 52 via the orifice 55 in the detector 50 (for about 10 seconds). Then, the valve SV17 is closed. At this time, the control section 500 detects changes in impedance between the electrodes 58 and 67, and the number of the white blood cells (WBC) is calculated on the basis of the detection result.

(3) At the same time, light emitted from the light emitting diode 68 is transmitted through the specimen, and the intensity of the transmitted light is detected by the photodiode 69. The control section 500 calculates the amount of the hemoglobin (HGB) on the basis of the detected light intensity. The blank measurement of the HGB (measurement of the intensity of light transmitted through the diluent) is performed immediately after Step (1) of the WBC measurement specimen preparing operation.

Measurement of RBC (Step S12)

(1) The valve SV16 is opened, and a negative pressure is applied to the waste liquid chamber WC from the negative pressure pump P1, whereby residual liquid in the detector 50 is drained into the waste liquid chamber WC. Then, the valve SV16 is closed.

(2) The valve SV13 is opened, and the syringe pump SR2 is operated for discharge, whereby the diluent is supplied into the first and third container chambers 51, 53 of the detector 50. Then, the valve SV13 is closed.

(3) The valves SV21, SV18 are opened, and a negative pressure is applied to the waste liquid chamber WC from the negative pressure pump P1, whereby the diluent is supplied from the diluent container B1 into the second container chamber 52 of the detector 50 for cleaning the second container chamber 52. Then, the valves SV21, SV18 are closed.

(4) The valves SV1, SV3 are opened, and the syringe pump SR2 is operated for suction, whereby the RBC measurement specimen is sucked from the mixing chamber 70 into a charging line CL and retained in the charging line CL. Then, the valves SV1, SV3 are closed.

(5) The valve SV17 is opened, and the syringe pump SR2 is operated for discharge, whereby the diluent flows from the third container chamber 52 into the first container chamber 51 through the orifice 55 in the detector 50.

(6) During this period, the valve SV7 is kept open, and the syringe pump SR1 is operated for discharge, whereby the RBC measurement specimen retained in the charging line CL is ejected from the jet nozzle 56 toward the orifice 55. The RBC measurement specimen ejected from the jet nozzle 56 is surrounded by the diluent in the preceding Step (5), and passes as a sheath flow through the orifice 55 (for about 10 seconds). Then, the valves SV1, SV7 are closed.

(7) The control section 500 calculates the number of the red blood cells (RBC), the number of the platelets (PLT), the hematocrit (HCT) and other analysis items on the basis of changes in impedance between the electrodes 58 and 67 when the sheath flow passes through the orifice 55.

Cleaning Operation (Step S15)

(1) The valves SV20, SV16 are opened, and then a negative pressure is applied to the waste liquid chamber WC from the negative pressure pump P1, whereby residual liquid in the mixing chamber 70 and the detector 50 is drained into the waste liquid chamber WC. Then, the valves SV20, SV16 are closed.

(2) The valves SV14, SV13 are opened, and the syringe pump SR2 is operated for discharge, whereby the diluent is supplied into the mixing chamber 70 and the detector 50. Then, the valves SV14, SV13 are closed.

(3) The valves SV1, SV2 are opened, and then a negative pressure is applied to the waste liquid chamber WC from the negative pressure pump P1, whereby the diluent is drained from the mixing chamber 70 into the waste liquid chamber through the charging line CL. Then, the valves SV1, SV2 are closed.

Thus, the cleaning operation is completed. The negative pressure in the waste liquid chamber WC is monitored by the pressure sensor J6, and the negative pressure pump P1 is driven to constantly keep the pressure within a range between 100 and 300 mmHg, preferably between 150 and 200 mmHg.

When the amount of the waste liquid stored in the waste liquid chamber WC reaches a predetermined amount, this situation is detected by the float switch J7, and the liquid draining pump P2 is driven, whereby the waste liquid is drained into the waste liquid container B2.

Input/display Section

The input/display section 3 gives information on inputting procedures to the user so that the user can perform an input operation without any error, and displays inputted information, the progress of the analysis and the results of the analysis.

The input/display section 3 will hereinafter be described in detail.

The control section 500 displays various screens on the liquid crystal display 3a on the basis of display information and a predetermined program stored in the ROM incorporated therein. These screens include a main screen which contains the start button for starting the analysis, a mode selection screen which contains mode selection buttons, a setting screen for selecting analysis items, and the like. In this embodiment, the start button 516 and the mode selection buttons 512, 514 are simultaneously displayed in the main screen (FIGS. 42(a), 43 and 44).

A display operation to be performed during the analyzing process by the blood analyzer will be described with reference the flow charts in FIGS. 31(a) and 31(b). The input/display section 3 performs the display operation in the following manner. When the predetermined preparation period is elapsed (Step S2) after the power supply to the blood analyzer is turned on (Step S1) as shown in FIG. 31(a), the main screen containing the message "Ready" is displayed on the liquid crystal display 3a of the input/display section 3 (FIG. 42(a)). The mode selection buttons 512, 514 and the start button 516 are displayed in this main screen.

The user sets the sample vessel containing the sample in the sample setting section 6 as described above (Step S4). Then, the user selects one of the whole blood mode and the pre-diluted mode for the analysis (Step S5). More specifically, the user touches one of the two mode selection buttons 512, 514 in the main screen for the selection.

Where the sample in the set sample vessel is a whole blood sample (for ordinary analysis), the user touches the whole blood mode button 512 displayed in red in the main screen on the input/display section 3 and, where the sample is a pre-diluted sample, the user touches the pre-diluted mode button 514 displayed in yellow in the main screen (Step S5).

When the user touches the whole blood mode button 512, the start button 516 in the main screen turns red. When the user touches the pre-diluted mode button 514, the start button 516 turns yellow. At this time, the control section 500 actuates the color changing section 500c and the color change controlling section 500d for changing the color of the button.

Subsequently, the user touches the start button 516, while confirming the analysis mode on the basis of the color of the start button displayed in the main screen (Step S6). The control section 500 judges which of the whole blood mode and the pre-diluted mode is selected, and starts a programmed process corresponding to the selected mode (Step S7).

Upon the start of the analytic operation on the basis of the input on the start button 516, the display on the input/display section 3 is switched from the main screen (FIG. 42(a)) to the measurement screen (FIG. 42(b)). At this time, analysis items are displayed in the measurement screen, but the results of the analysis are not displayed because the analysis is not completed.

At this time, five analysis items (WBC, RBC, HGB, HCT, PLT) which are supposedly the most important are displayed by default.

When the whole blood mode is selected, the RBC measurement specimen and the WBC measurement specimen are prepared from the whole blood sample (Steps S8, S9).

When the pre-diluted mode is selected, the RBC measurement specimen and the WBC measurement specimen are prepared from the pre-diluted sample (Steps S16, S17).

With the use of the WBC measurement specimen prepared in Step S9, the measurement of the WBC and the HGB (hemoglobin concentration) is first performed (Step S10). When the results of the measurement are obtained, measurement result data for these two items is displayed in the current measurement screen (FIG. 42(c)) (Step S11).

With the use of the RBC measurement specimen prepared in Step S8, the measurement of the RBC is performed (Step S12), and the PLT (the number of platelets), the HCT (hematocrit value) and other analysis items are calculated (Step S13). Then, the results of the measurement and the calculation are displayed in the measurement screen (Step S14). At this time, the results of the measurement of the five items are displayed in a greater font size in the measurement screen (FIG. 42(d)).

Subsequently, the cleaning operation is started to prepare for the next analysis (Step S15). FIG. 31(b) is a detailed flow chart for Step S15. Referring to FIG. 31(b), it is checked whether the touch panel is operated for displaying eight analysis items during the cleaning operation (Step S18). If the operation for the eight-item display is performed, the display is switched to an eight-item display screen in which the eight analysis items are displayed in a smaller font size (FIG. 42(e)) (Step S19).

Figures 49, 50:
FIG. 49 is a diagram illustrating still another exemplary measurement screen for displaying all analysis items (8 items)
FIG. 50 is a diagram illustrating further another exemplary measurement screen (for displaying statistic data obtained by the WBC measurement)

The eight-item display screen (FIGS. 42(e) and 49) is kept displayed until a return button ("Top" button) 534 is touched (Step S20). When the return button 534 is touched, the display is switched to the main screen (FIG. 42(a)) (Step S21).

If the operation is not performed in Step S18, the five-item display screen (FIG. 42(d)) is kept displayed until the cleaning operation is completed (Step S22).

Upon the completion of the cleaning operation, the display is switched to the main screen (FIG. 42(a)) (Step S21), and the routine returns to Step S3 on standby for the analysis of the next sample. If the operation for the eight-item display is not performed before the completion of the cleaning operation, it is judged that there is no need for the eight-item display, and the display is automatically switched to the main screen (FIG. 42(a)). For judgment on the automatic switching to the main screen (FIG. 42(a)), the control section 500 has to judge whether the cleaning operation is completed. In this embodiment, the control section 500 determines the completion of the cleaning operation on the basis of the signals applied thereto from the sensors provided in the analyzer. For this purpose, a timer may additionally be provided, and the control section 500 may be adapted to determine the completion of that the cleaning operation on the basis of a lapse of a predetermined period from the start of the cleaning operation, and automatically switch the display from the five-item display screen (FIG. 42(d)) to the main screen (FIG. 42(a)). Alternatively, the control section 500 may be adapted to automatically switch the display from the five-item display screen (FIG. 42(d)) to the main screen (FIG. 42(a)) after a lapse of a predetermined period from the determination of the completion of the cleaning operation.

Next, an explanation will be given to the contents of the main screen and the measurement screen.

Main Screen

Figure 43:
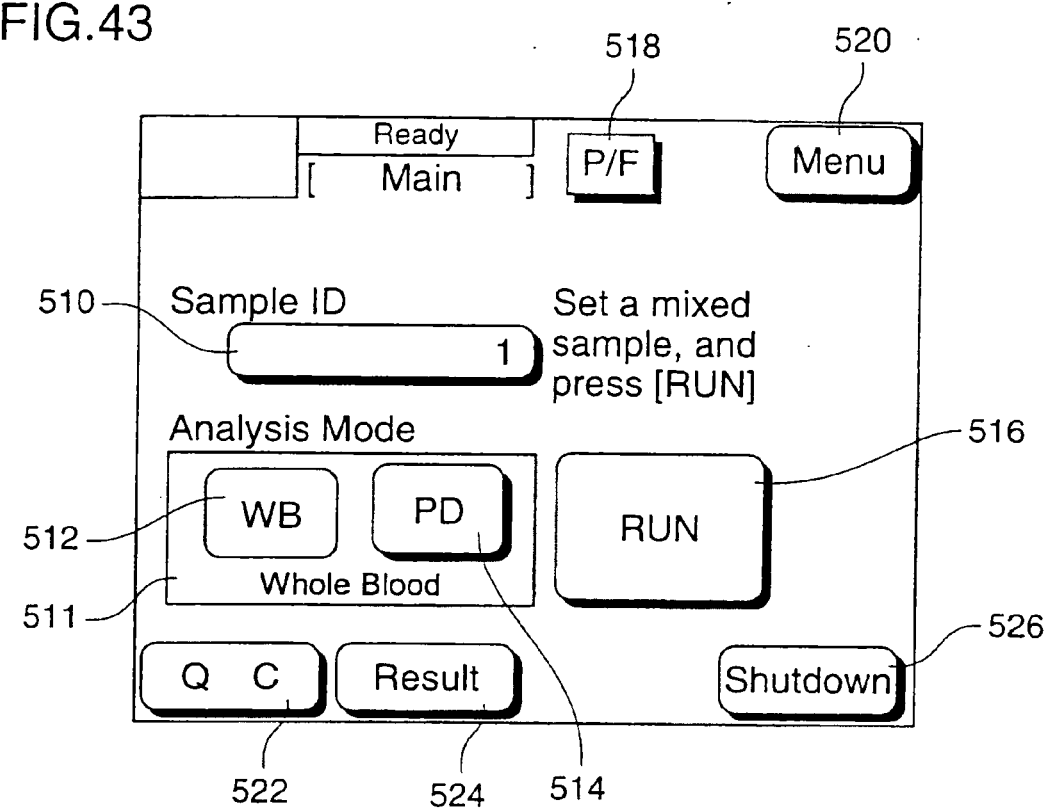
FIG. 43 is a diagram illustrating an exemplary main screen (to be displayed when a whole blood mode is selected)
Figure 44:
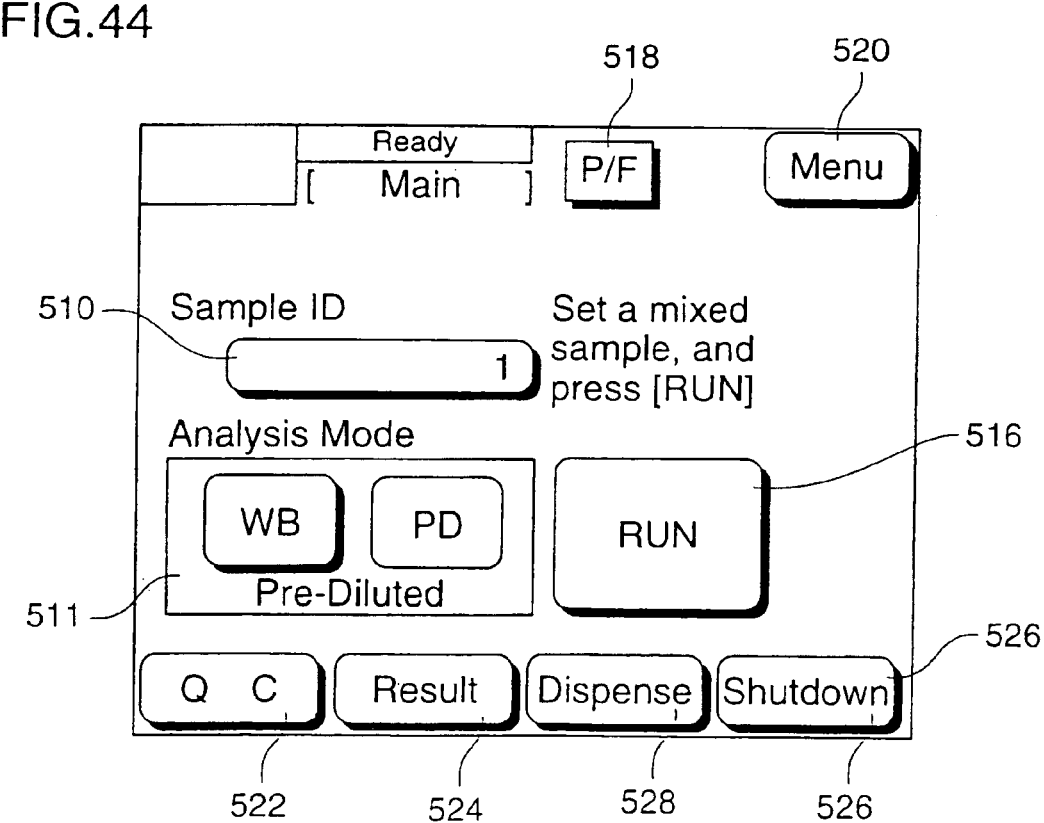
FIG. 44 is a diagram illustrating another exemplary main screen (to be displayed when a pre-diluted mode is selected)

FIGS. 43 and 44 are diagrams illustrating the contents of the main screen. Particularly, FIG. 43 illustrates a screen displayed when the whole blood mode is selected, and FIG. 44 illustrates a screen displayed when the pre-diluted mode is selected. As shown, the whole blood mode button 512 and the pre-diluted mode button 514 are displayed in an analysis mode region 511. The start button 516 is displayed in a start button region. Besides, a P/F button 518 for sheet feeding of the printer, a menu button 520 for selecting various menu items such as calibration, a QC button 522 for controlling the accuracy of the analyzer, a button 524 for displaying the measurement results of the previously analyzed sample, a shutdown button 526 for starting a shutdown operation (for turning off the analyzer after the cleaning operation), and a dispensing button 528 for performing a dispensing operation in the pre-diluted mode) are displayed on the input/display section.

Since the touch panel 3b is superposed on the liquid crystal display 3a, a function of each of the buttons is effectuated by touching (or pressing) a corresponding portion of the touch panel 3b by a finger or the like. The function is performed according to the program preliminarily stored in the control section 500.

A sample ID is entered in a region 510 by inputting a numeral or the like from a keyboard (not shown), which may be a pop-up keyboard to be displayed as required.

An explanation will be given to the selection of an analysis mode. The whole blood mode button 512 and the pre-diluted mode button 514 shown in FIG. 43 are colored red and yellow, respectively. The two buttons 512, 514 having different colors can be discriminated by color, so that the possibility of mistaken button pressing is diminished.

When the whole blood mode button 512 is touched, for example, the whole blood mode button 512 is three-dimensionally displayed as being depressed, and the pre-diluted mode button 514 is three-dimensionally displayed as projecting. On the other hand, when the pre-diluted mode button 514 is touched, the pre-diluted mode button 514 is displayed as being depressed, and the whole blood mode button 512 is displayed as projecting. Thus, the mode button touched on the two-dimensional touch panel is visually three-dimensionally displayed. Therefore, the selected mode button can clearly be discriminated from the other mode button, whereby the possibility of mistaken mode selection is diminished.

At the same time, a message "Whole blood" or "Pre-diluted" is displayed below the whole blood mode button 512 and the pre-diluted mode button 514, whereby the mistaken mode selection is prevented.

In addition, the color of the start button 516 is changed according to the selected analysis mode. As described above, the whole blood mode button 512 and the pre-diluted mode button 514 are displayed in red and yellow, respectively, in this embodiment. When the whole blood mode button 512 is pressed for the selection of the whole blood mode, the start button 516 is turned red. When the pre-diluted mode button 514 is pressed for the selection of the pre-diluted mode, the start button 516 is turned yellow. The whole blood mode button 512 may be displayed in red constantly or only when the whole blood mode is selected. Similarly, the pre-diluted mode button 514 may be displayed in yellow constantly or only when the pre-diluted mode is selected. In either case, it is merely necessary that the whole blood mode button 512 and the pre-diluted mode button 514 are not simultaneously displayed in the same color. The colors of the respective mode buttons are preferably selected so as to be easily distinguished from each other.

Figure 45:
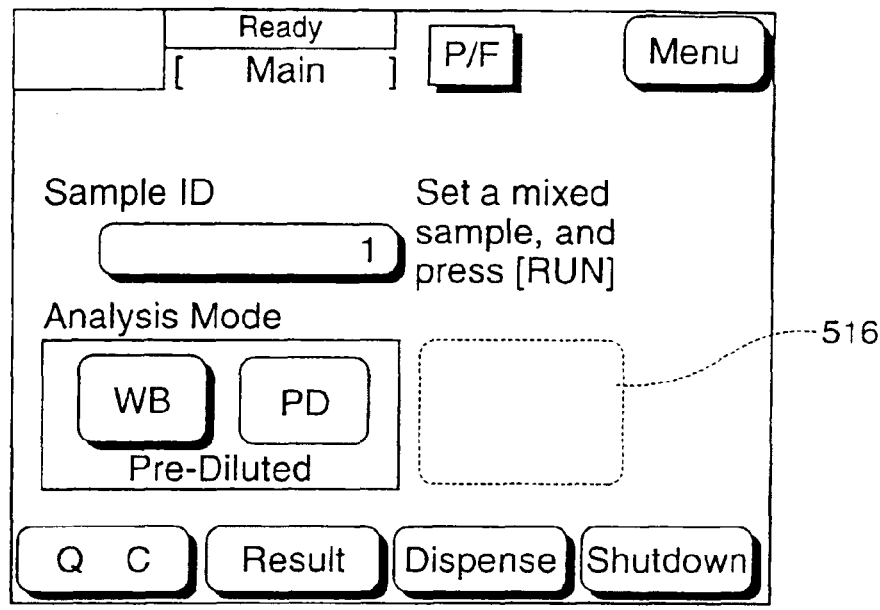
FIG. 45 is a diagram illustrating further another exemplary main screen (to be displayed in a measurement impossible state)

When the start button 516 is touched in the main screen, the analysis is started. However, if the analysis is started before the completion of the cleaning operation or when the analyzer is short of the reagents or in trouble, a malfunction may occur in the analyzer. Therefore, the control section 500 monitors the signals from the driver circuit section 501 and the like to check for the shortage of the reagents and the state of the analyzer. Then, the control section 500 permits the display of the start button 516 if the preparation for the analysis is completed, and prohibits the display of the start button 516 as shown in FIG. 45 if the analyzer is in a measurement impossible state before the completion of the preparation or when the analyzer is in trouble. Thus, the user is prevented from carelessly pressing the start button 516, and easily founds that the analysis cannot be started.

The control section 500 monitors, for example, information on the completion of the cleaning operation and analyzer trouble information based on the outputs of the panel opening/closing sensor J1, the sample detecting sensor J2 and the like. With the start button not displayed, there is a blank space on the display, so that a message of the measurement impossible state may be displayed in a greater font size in the blank space.

Measurement Screen

Figure 46:
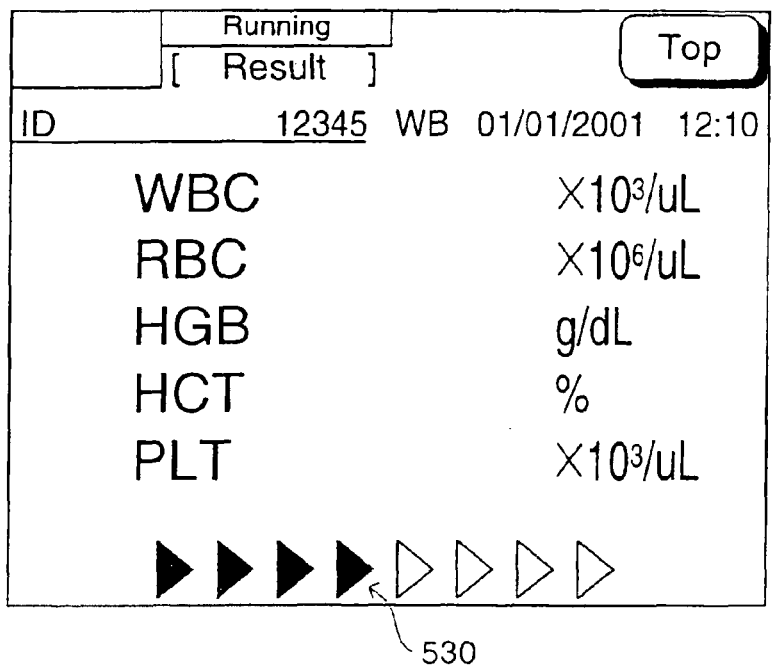
FIG. 46 is a diagram illustrating an exemplary measurement screen (to be displayed immediately after the start of an analysis)
Figures 47, 48:
FIG. 47 is a diagram illustrating another exemplary measurement screen (to be displayed after completion of WBC measurement)
FIG. 48 is a diagram illustrating further another exemplary measurement screen (to be displayed after completion of RBC measurement)

Next, an explanation will be given to screens to be displayed during the analysis. FIG. 46 illustrates a measurement screen to be displayed immediately after the start button 516 is pressed for starting the analysis. FIG. 47 illustrates a measurement screen to be displayed after the results of the measurement with the use of the WBC measurement specimen are obtained. FIG. 48 illustrates a measurement screen to be displayed immediately after the analysis is completed with the results of the measurement with the use of the RBC measurement specimen obtained. As shown in FIGS. 46 and 47, the progress of the analysis is indicated by displaying graphics (triangles) 530 with color variations on a bottom line.

In these measurement screens, the five basic analysis items (WBC, RBC, PLT, HGB and HCT) are displayed in a greater font size.

Since the measurement results are not obtained immediately after the start of the analysis, the analysis items (and their units) are simply displayed. After a lapse of about 20 seconds from the start of the analysis, the measurement with the use of the WBC measurement specimen is completed, and data on the WBC and the HGB obtained in this measurement is displayed as shown in FIG. 47.

After a lapse of about 80 seconds from the completion of the WBC measurement, the measurement with the use of the RBC measurement specimen is completed, and the results of the measurement for the five analysis items are displayed as shown in FIG. 48.

When an arrow button (forward button) 532 provided in a right bottom corner in FIG. 48 is touched, an eight-item measurement result screen is displayed as shown in FIG. 49, which contains the MCV (mean corpuscular volume), the MCH (mean corpuscular hemoglobin) and the MCHC (mean corpuscular hemoglobin concentration) in addition to the aforesaid five analysis items. In this screen, all the analysis items measured by the blood analyzer are displayed. Since the number of the analysis items is increased, the analysis items are displayed in a smaller font size.

Figure 51:
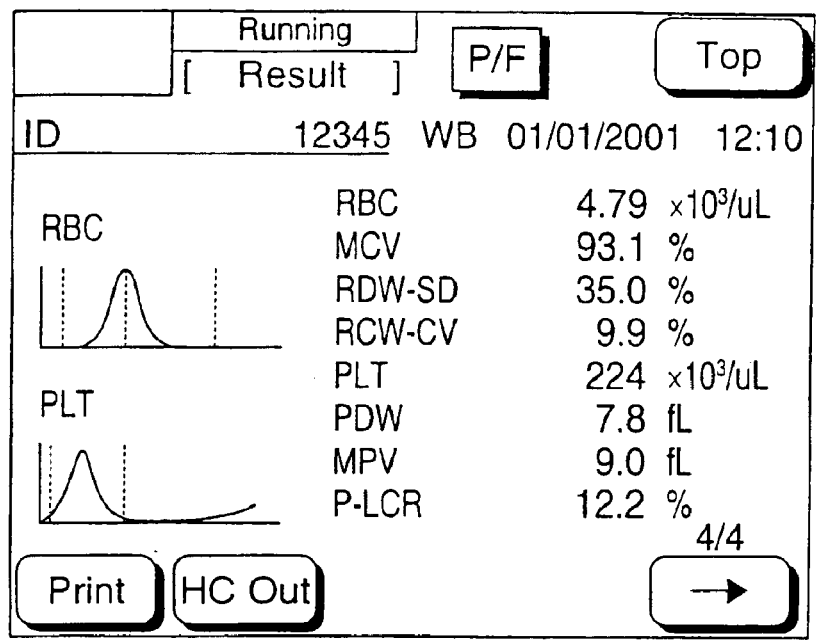
FIG. 51 is a diagram illustrating still another exemplary measurement screen (for displaying statistic data obtained by the RBC and PLT measurement)

Statistic data screens related to the results of the measurement with the use of the WBC measurement specimen and the RBC measurement specimen may be displayed as shown in FIGS. 50 and 51, when the forward button 532 is further touched on the screen shown in FIG. 49. Alternatively, the display may be switched back to the five-item display screen (FIG. 48 or 42(d)) from the eight-item display screen (FIG. 49 or 42(e)).

By thereafter touching the return button 534 displayed in the right upper corner of the screen in FIG. 49, 50 or 51, the display is switched back to the main screen (FIGS. 42(a), 43 and 44).

The user may desire to perform the analysis of the next sample without examination of the data displayed in the eight-item display screen (or the statistic data screens). Therefore, where no input operation is performed during an about 20-second period from the start of the display of the screen shown in Fig. FIG. 48 to the completion of the cleaning operation, i.e., where the forward button 532 is not operated during this period for the display of the eight-item display screen, the display is automatically switched to the main screen with no need for viewing the data shown in FIG. 49.

The input/display section 3 is adapted to display the five basic analysis items after the start of the analysis in this embodiment. However, the input/display section 3 may be adapted to preliminarily register desired analysis items selected from the measurable analysis items and optionally display a screen containing only the selected analysis items separately from the eight-item display screen.

Figure 52:
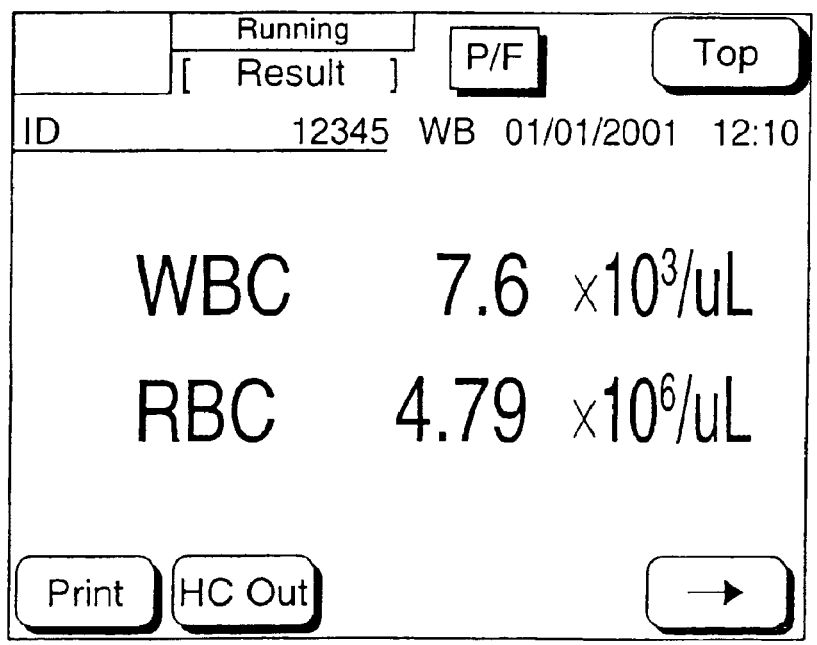
FIG. 52 is a diagram illustrating further another exemplary measurement screen (to be displayed when analysis items are selected as desired)

FIG. 52 illustrates a screen preliminarily registered as a first measurement screen containing the WBC and the RBC. For registration of the desired analysis items, the menu button 520 in the screen shown in FIG. 43 or 44 is touched to invoke a setting screen, and a program is run in the setting screen for selecting the desired analysis items. In this program, the font size is predefined according to the number of the selected analysis items (for example, a font size of 20 points is employed for display of up to two analysis items, and a font size of 16 points is employed for display of up to five analysis items). Thus, the font size is determined according to the number of the analysis items.

Detection Circuit of Resistance-Type Detecting Section

The detection circuit employed for the resistance-type detecting section 503 requires a booster circuit for boosting the DC voltage (12V) outputted from the power supply section 10 to a level of 50V or higher. In this invention, a Cockcroft power supply is employed as the booster circuit.

An explanation will hereinafter be given to the detection circuit for the resistance-type detecting section 503.

Figure 53:
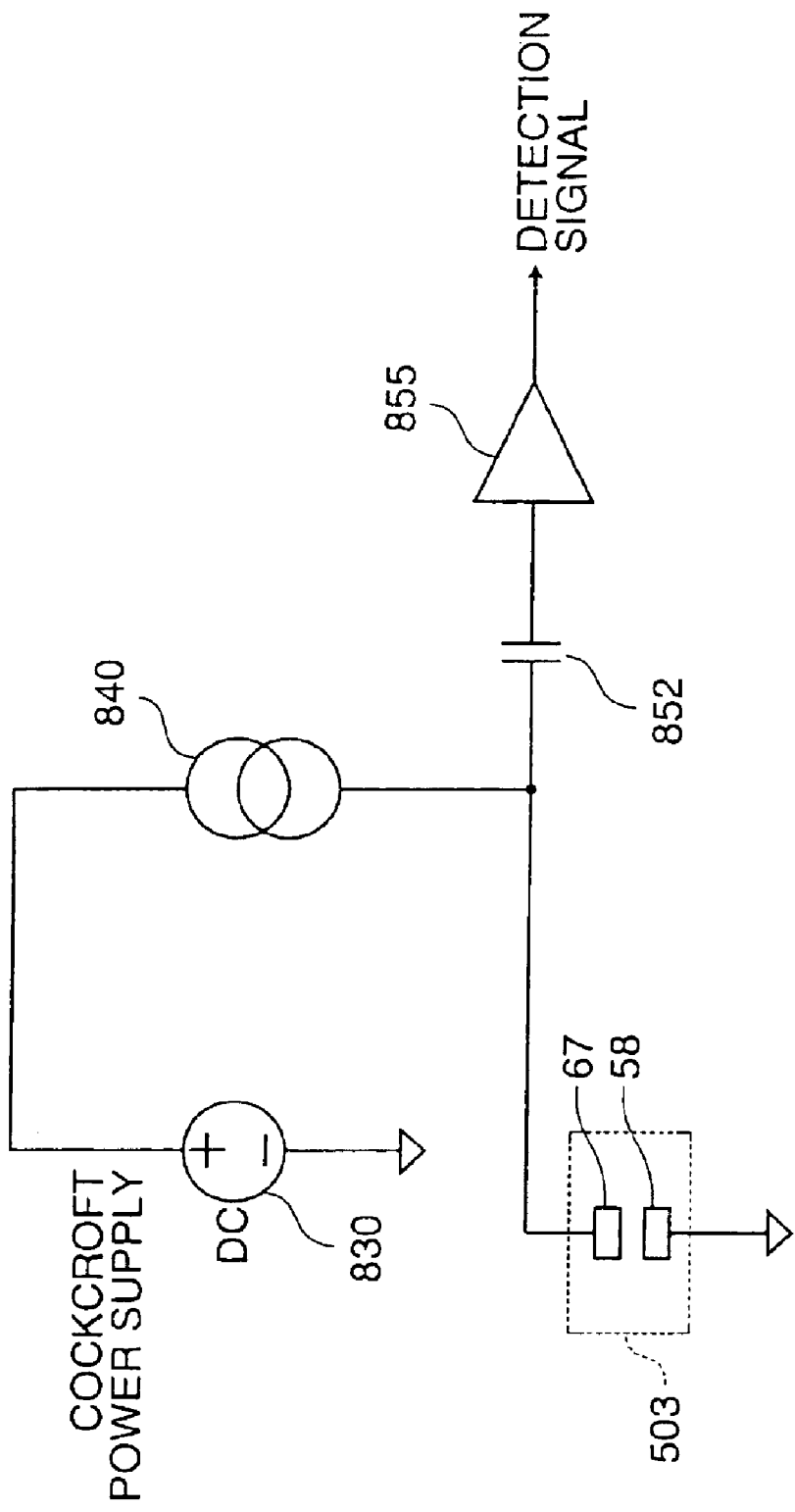
FIG. 53 is a circuit diagram of a detection circuit of the blood analyzer according to this invention.

FIG. 53 is a basic circuit diagram of the detection circuit for the resistance-type detecting section 503. As shown, the DC voltage is applied from the Cockcroft power supply 830 to a serial circuit consisting of a constant electric current circuit 840 and the resistance-type detecting section 503. A terminal voltage of the resistance-type detecting section 503 is inputted to an amplifier circuit 855 via a capacitor 852 which removes a DC component, and the amplified voltage is outputted as a detection signal.

When particles such as blood cells pass through the orifice 55 (FIG. 23), the impedance between the electrodes 58 and 67 (see FIGS. 23 and 24) slightly fluctuates. Since the constant electric current circuit 840 constantly applies a constant electric current to the orifice 55, a slight voltage variation occurs between the electrodes 58 and 67 according to the fluctuation of the impedance. The voltage variation is inputted to the amplifier 855 after the removal of the DC component by the capacitor 852, whereby the detection signal is obtained.

Next, an explanation will be given to the Cockcroft power supply 830.

Figure 54:
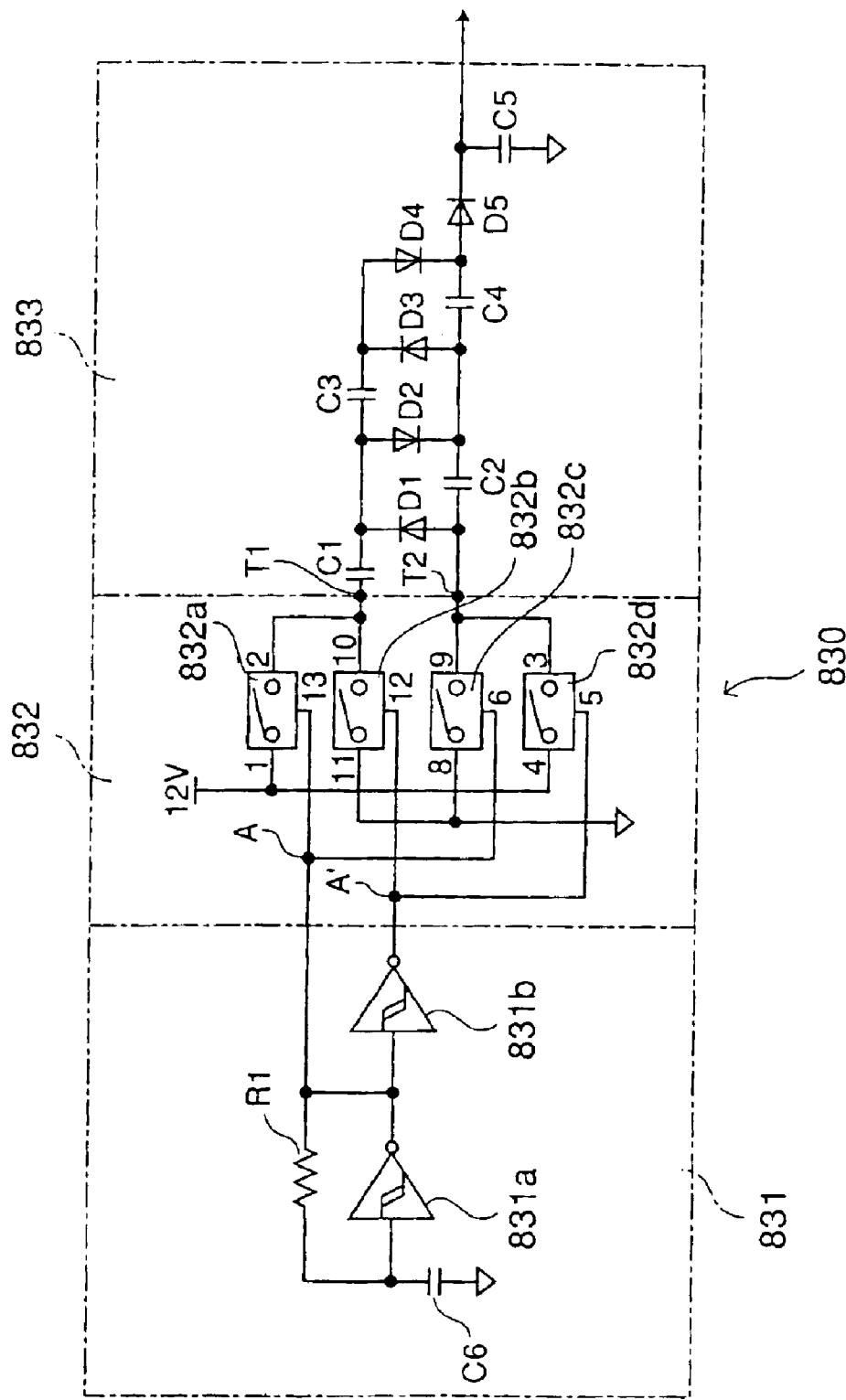
FIG. 54 is a circuit diagram of a Cockcroft power supply employed in the blood analyzer according to this invention.

The Cockcroft power supply 830 includes an oscillator 831, a switching circuit 832 and a booster 833 as shown in FIG. 54.

Figure 60:
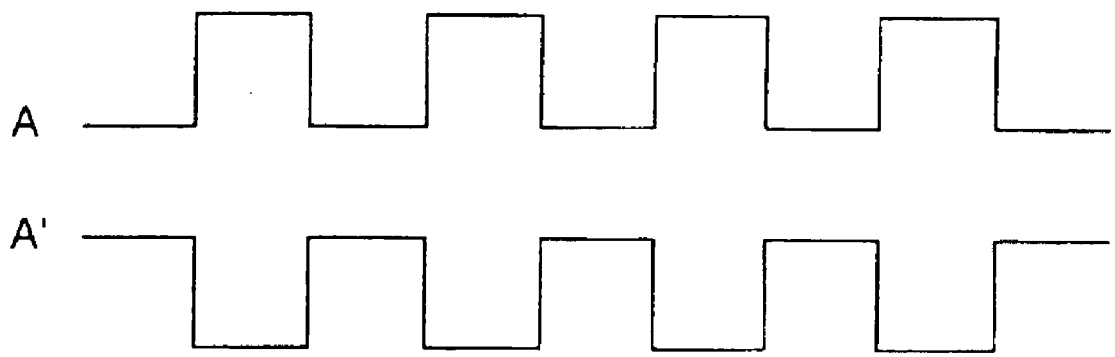
FIG. 60 is a diagram of waveforms obtained at terminals in FIG. 54.

The oscillator 831 includes an RC oscillation circuit constituted by an operation amplifier element 831a, a resistor $R_1$ and a capacitor $C_6$, and an inversion operation amplifier element 831b connected to one of branched output terminals of the RC oscillation circuit. With this arrangement, two square waves A, A' having opposite phases as shown in FIG. 60 are outputted from the oscillator 831. These square wave outputs are supplied to the switching circuit 832.

The switching circuit 832 includes two analog switching elements 832a, 832d connected to the DC power supply (+12V), and two analog switching elements 832b, 832c connected to a ground terminal.

The analog switching elements 832a, 832c operate in synchronization with the square wave A, and the analog switching elements 832b, 832c operate in synchronization with the square wave A' having an inverted phase for opening and closing thereof.

The analog switching elements 832a, 832b are connected to each other to be paired, and the analog switching elements 832c, 832d are connected to each other to be paired. The analog switching element pairs are respectively connected to the booster 833 via output terminals T1 and T2.

In the switching circuit 832, the four analog switching elements are switched in synchronization with the square waves A, A' having opposite phases. When a voltage of +12V is applied to one of the output terminals T1, T2, the other output terminal is connected to the ground thereby to have a voltage of 0V. Thus, the terminals T1, T2 are alternately switched between +12V and 0V.

The booster 833 is connected to the output terminals T1, T2 of the switching circuit 832. The booster 833 includes capacitors $C_1$ to $C_4$ and diodes $D_1$ to $D_4$ for boosting the voltage. More specifically, a cathode of the diode $D_1$ is connected to an anode of the diode $D_2$, and a cathode of the diode $D_2$ is connected to an anode of the diode $D_3$. The other diodes are serially connected to each other in this manner. The capacitors $C_1$ to $C_4$ are each connected between the anode and cathode of two adjacent diodes. However, the first capacitor $C_1$ is connected between the output terminal T1 of the switching circuit 832 and the diode $D_1$.

A voltage of +12V is applied alternately to the terminals of the booster 833 from the switching circuit 832. The applied voltage is boosted by each of the capacitors thereby to be virtually multiplied by the number of the capacitors. Since the four capacitors and the four diodes are connected to one another in FIG. 54, an output voltage of 55V is obtained which is nearly equal to the product of 12V multiplied by 5. A value obtained by the calculation is 60V but, actually, reduced by a forward voltage drop of the diodes.

The boosted voltage is outputted to a subsequent circuit through a rectifier diode $D_5$ and a smoothing capacitor $C_5$.

A common constant electric current circuit, for example, a current mirror circuit employing transistors, may be employed as the constant electric current circuit 840 to which the voltage generated by the Cockcroft power supply 830 is supplied.

Experiments were performed to check if the Cockcroft power supply 830 stably serves as the booster circuit, and the results of the experiments are shown below.

Figure 55:
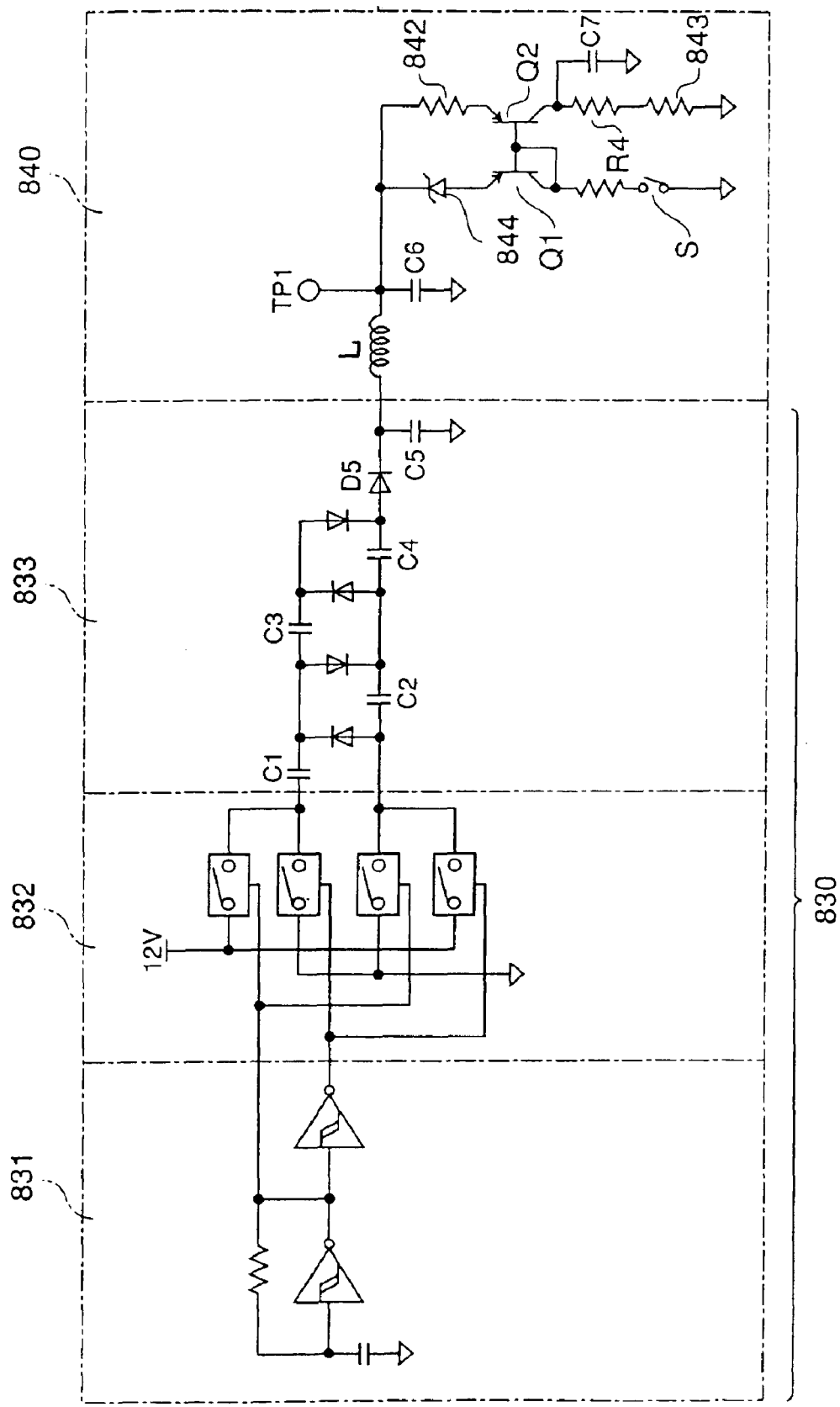
FIG. 55 is a diagram of an experimental circuit employed for confirming the performance of the Cockcroft power supply.

The basic construction of a circuit for the experiments is shown in FIG. 55. As shown in FIG. 55, the Cockcroft power supply 830 shown in FIG. 54 is connected to the constant electric current circuit 840.

The constant electric current circuit 840 employed for these experiments is a current mirror circuit employing transistors. The constant electric current circuit 840 includes a choke coil L and a capacitor C6 for smoothing, a resistor (resistance Rs) 842 for setting an electric current level, a dummy resistor 843 corresponding to an impedance of the resistance-type detecting section 503, a Zener diode 844 for generating a reference voltage Es, transistors Q1, Q2, resistors R3, R4, a capacitor C7 and an operation switch S. The resistance Rs of the electric current setting resistor 842 is properly set as a parameter to determine the electric current level which is equal to Es/Rs.

Figure 57:
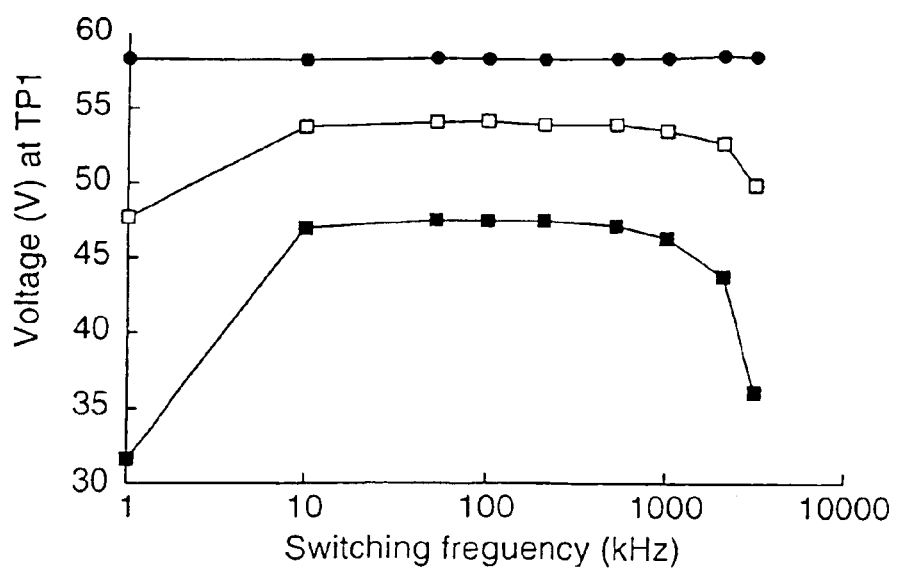
FIG. 57 is a graph illustrating a relationship between a switching frequency and an output voltage.

Experiment data indicative of a relationship between the switching frequency (kHz) of the oscillator 831 of the Cockcroft power supply 830 and the output voltage (V) is shown in Table 1 and FIG. 57.

TABLE 1

| Switching frequency (kHz) | With no load electric current | With load electric current of 0.75 mA | With load electric current of 2.50 mA |
|---|---|---|---|
| 1 | 58.1 | 47.5 | 31.5 |
| 10 | 58.0 | 53.6 | 46.7 |
| 50 | 58.0 | 53.8 | 47.2 |
| 100 | 58.0 | 53.8 | 47.1 |
| 200 | 58.0 | 53.7 | 47.1 |
| 500 | 57.9 | 53.6 | 46.7 |
| 1000 | 58.0 | 53.2 | 45.9 |
| 2000 | 58.2 | 52.3 | 43.5 |
| 3000 | 58.1 | 49.5 | 35.7 |

In this experiment, a pulse generator was employed instead of the oscillation circuit 831 for easily varying the switching frequency.

Further, 1-$\mu$F ceramic capacitors were employed as the capacitors $C_1$ to $C_4$ of the booster 833.

By adjusting the electric current setting resistor 842 of the constant electric current circuit 841, load electric currents of 0 mA, 0.75 mA and 2.50 mA were applied. At this time, the output voltage of the Cockcroft power supply was measured at the terminal TP1 provided in the constant electric current circuit 841.

As can be seen from Table 1 and FIG. 57, the output voltage did not rely on the switching frequency with no load electric current on the constant electric current circuit. With a greater load electric current, on the other hand, the output voltage was advantageously increased as the switching frequency was increased. However, the output voltage was lower at a switching frequency higher than a certain level. This is supposedly because the output voltage was influenced by operation speeds and ON resistances of the analog switching elements of the switching circuit 832. Further, the output voltage was lower at a lower switching frequency. This is supposedly because it was impossible to maintain the output voltage with insufficient current supply at the lower switching frequency.

The experiment data suggests that the power supply is preferably operated at a switching frequency of 50 to 1000 kHz to provide an output voltage of about 50V.

Figure 58:
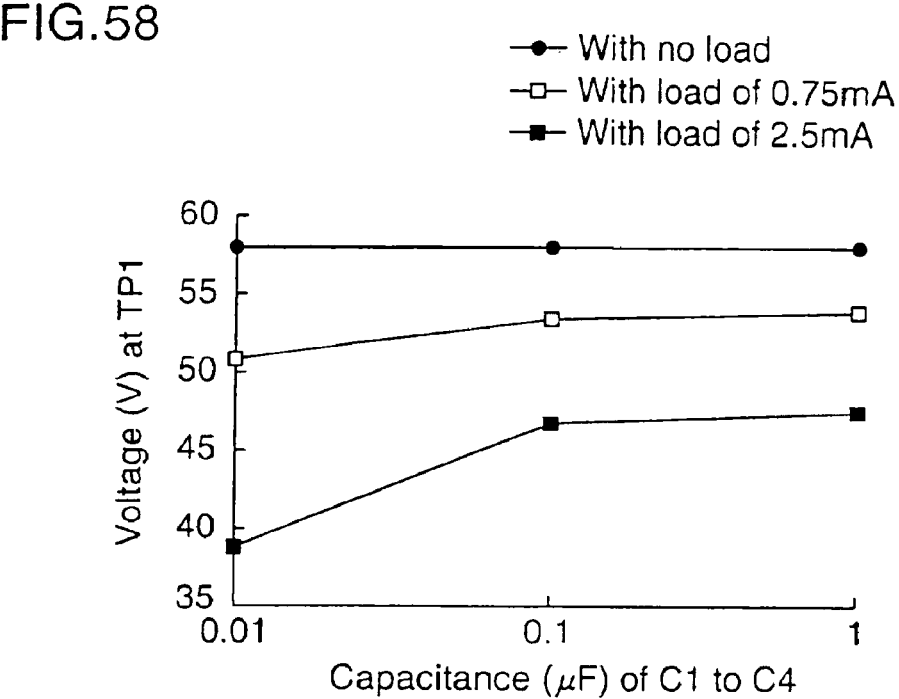
FIG. 58 is a graph illustrating a relationship between the capacitance of capacitors and the output voltage.

Next, experiment data indicative of a relationship between the capacitance ($\mu F$) of the booster capacitors $C_1$ to $C_4$ and the output voltage (V) is shown in Table 2 and FIG. 58.

TABLE 2

| Capacitance of $C_1$ to $C_4$ ($\mu F$) | With no load electric current | With load electric current of 0.75 mA | With load electric current of 2.50 mA |
| --- | --- | --- | --- |
| 1 | 58.3 | 54.2 | 47.8 |
| 0.1 | 58.2 | 53.7 | 47.1 |
| 0.01 | 58.1 | 50.9 | 39.0 |

Ceramic capacitors having capacitances of 1 $\mu F$, 0.1 $\mu F$ and 0.01 $\mu F$ were employed as the capacitors $C_1$ to $C_4$ of the booster 833. By adjusting the electric current setting resistor 842 of the constant electric current circuit 841, load electric currents of 0 mA, 0.75 mA and 2.50 mA were applied as in the preceding experiment. Then, the output voltage of the Cockcroft power supply was measured at the terminal TP1.

As can be seen from Table 2 and FIG. 58, the output voltage did not rely on the switching frequency with no load electric current. The electric current capacity of the power supply was increased with the capacitance of the capacitors as the load electric current was increased.

Therefore, a greater capacitance is more advantageous in terms of the electric current capacity, but capacitors having a greater capacitance have a greater size. Thus, the experiment data suggests that capacitors having a capacitance of 1 $\mu F$ are preferred which practically present no problem.

Next, the switching frequency of the Cockcroft power supply and the circuit constants of the capacitors were optimized on the basis of the relationship between the switching frequency and the output voltage and the relationship between the capacitance of the capacitors and the output voltage, and the performance of the power supply was examined.

Figure 59:
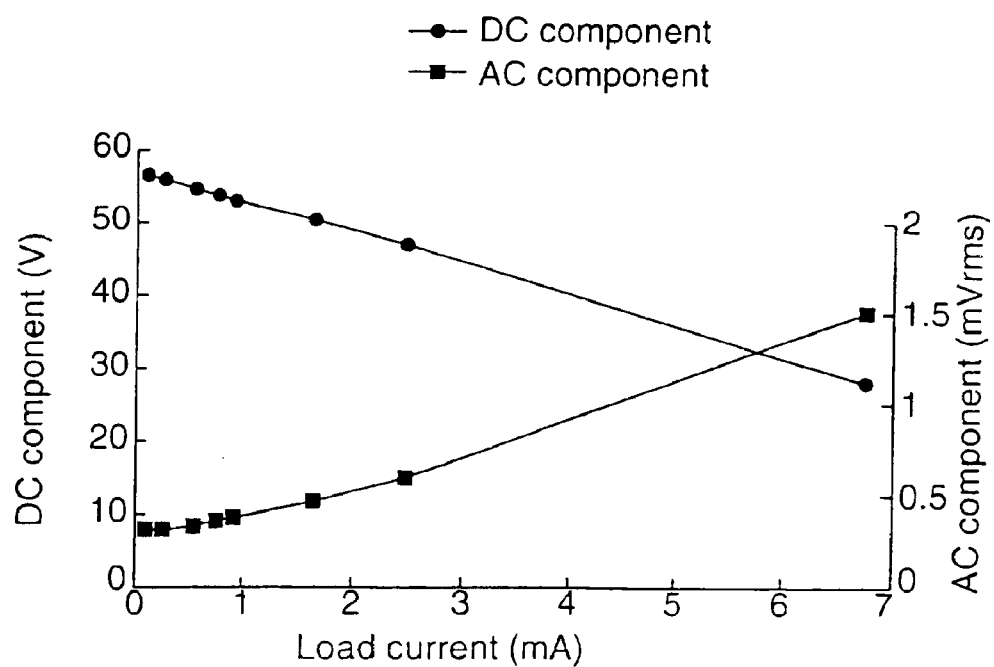
FIG. 59 is a graph illustrating a relationship between a load electric current and a power supply voltage.

Experiment data indicative of a relationship between the load electric current and the voltage of the power supply is shown in Table 3 and FIG. 59.

The switching frequency was set at 160 kHz which falls within the aforesaid preferred range ($R_1$=47 k$\Omega$, $C_6$=100 pF in the oscillation circuit 831 in FIG. 54), and the capacitors $C_1$ to $C_4$ each had a capacitance of 1 $\mu F$.

TABLE 3

| | Voltage at TP1 | |
| --- | --- | --- |
| Load electric current (mA) | DC component (V) | AC component (mVrms) |
| 0.09 | 56.4 | 0.30 |
| 0.25 | 55.8 | 0.31 |
| 0.53 | 54.7 | 0.33 |
| 0.76 | 53.8 | 0.36 |
| 0.92 | 53.2 | 0.37 |
| 1.64 | 50.4 | 0.47 |
| 2.46 | 47.4 | 0.60 |
| 6.74 | 28.7 | 1.53 |

As can be seen from Table 3 and FIG. 59, the DC component was reduced and the AC component was increased, as the load electric current was increased. When the load electric current was not lower than 1.64 mA, the DC component was reduced to 50 V or lower. Requirements for the power supply for the detecting circuit (an output voltage of not smaller than 50V, a load electric current of 0.6 to 1 mA) were sufficiently satisfied. Therefore, the experiment data indicates that the Cockcroft power supply can advantageously be employed for the booster circuit.

Next, the power consumption of the Cockcroft power supply was measured. The results of the measurement are shown below.

The power consumption was determined by inserting a resistor (about 10 $\Omega$) between the switching elements and a DC input voltage source (+12V) connected to the switching circuit 832, and observing a voltage drop.

As a result, the power consumption was 3 mW on standby (where the switching operation of the Cockcroft power supply was off), and 83 mW when the detection electric current was on (with a load electric current of 0.75 mA).

Figure 56:
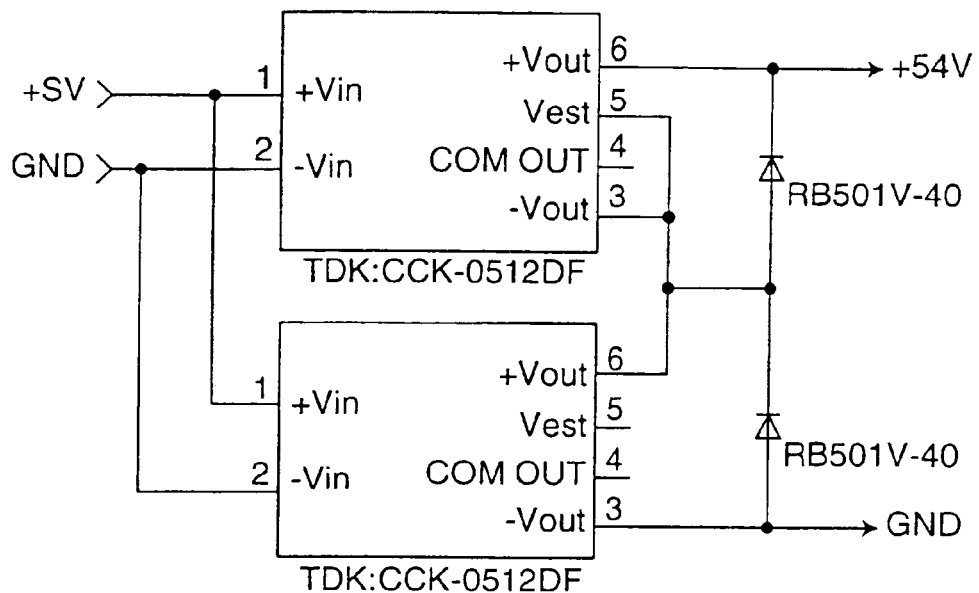
FIG. 56 is a circuit diagram of a booster circuit employing a commercially available DC-DC converter.

On the other hand, where a commercially available DC-DC converter shown in FIG. 56 was employed, the power consumption was 580 mW on standby (with a voltage of 5V supplied to the DC-DC converter and with a voltage outputted with no load), and 640 mW when the detection electric current was on (with a load electric current of 0.75 mA).

The power consumption of the booster circuit employing the Cockcroft power supply is much lower than that of the booster circuit employing the commercially available DC-DC converter, and is drastically reduced as compared with a booster circuit employed in the conventional analyzer.

As a result, the booster circuit employing the Cockcroft power supply generates a smaller amount of heat in operation and, therefore, can spontaneously be cooled without the need for forcibly cooling the booster circuit by a cooling fan or the like.

Container Housing Unit, Container Holder and Flow Path Connection Mechanisms

An explanation will hereinafter be given to the container housing unit 100 shown in FIG. 3, a container holder 950 (FIG. 69) for holding the container housing unit 100 and flow path connection mechanisms for fluid communication between the container housing unit 100 and the analyzer main body 1.

Container Housing Unit

Figure 61:
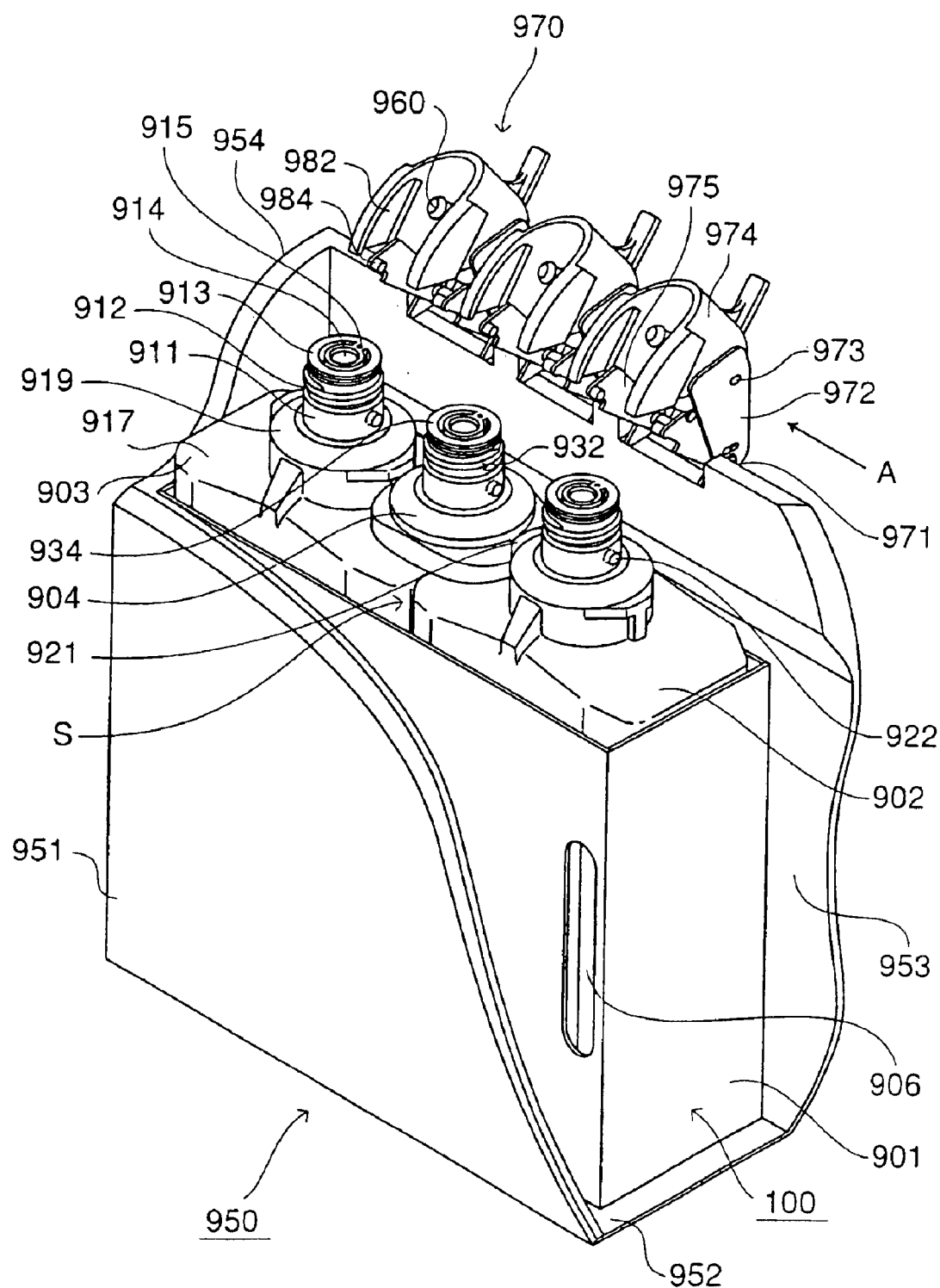
FIG. 61 is a diagram illustrating the appearance of the container housing unit held in a container holder according to this invention.

As shown in FIG. 61, the container housing unit 100 includes an inner case 901, generally square large containers 902, 903 and a generally square small container 904. As shown in FIG. 61, the inner case 901 is of a rectangular box shape having an open top and a handle hole 906 formed in a side wall thereof for easy handling of the inner case 901 with a user's finger inserted therein. The formation of the handle hole 906 may be achieved by preliminarily perforating a portion of the inner case, and tearing off the perforated portion.

The inner configuration and dimensions of the inner case 901 are defined in accordance with the outer configuration and dimensions of the two large containers 902, 903 which are disposed in juxtaposition with opposed faces (indicated by a reference character S in FIG. 61) of the containers 902, 903 in contact with each other, so that the two large containers 902, 903 can neatly be accommodated and positioned in the inner case 901. If the large containers need to be disposed in spaced juxtaposed relation due to positional relationships between the large containers and guide mechanisms 970 attached to the container holder 950, the inner configuration of the inner case 901 may be defined in accordance with the outer configuration and outer dimensions of all the containers to be accommodated in combination in the inner case 901. Thus, the containers can properly be positioned in the inner case 901. The inner case 901 is formed, for example, of a cardboard or a plastic. The inner case may be lidded with the containers accommodated therein. One of the large containers 902, 903 is employed as the diluent container B1 and the other large container is employed as the waste liquid container B2 shown in FIG. 29.

Figure 62:
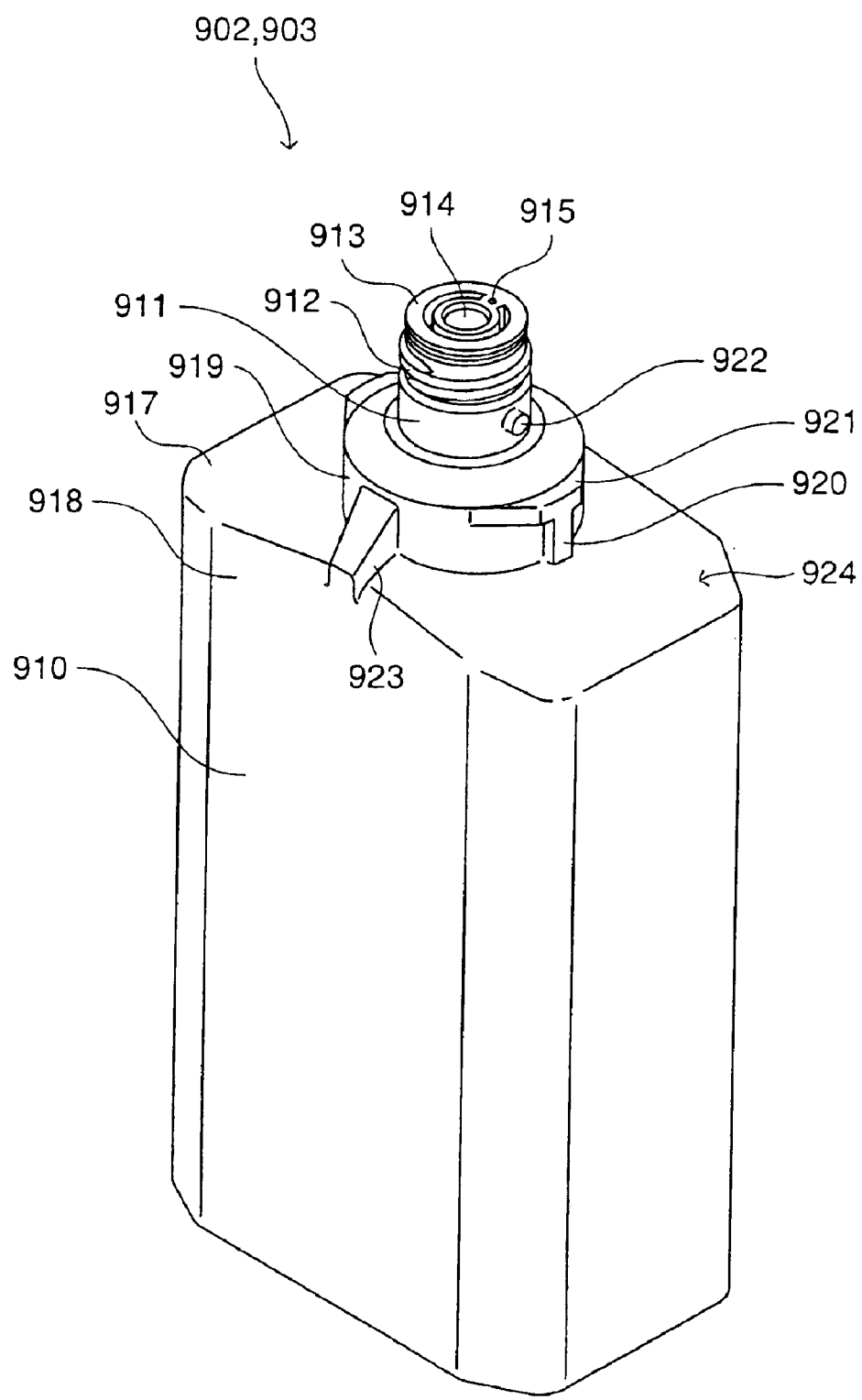
FIG. 62 is a diagram illustrating the construction of a large container employed for the container housing unit according to this invention.
Figure 63:
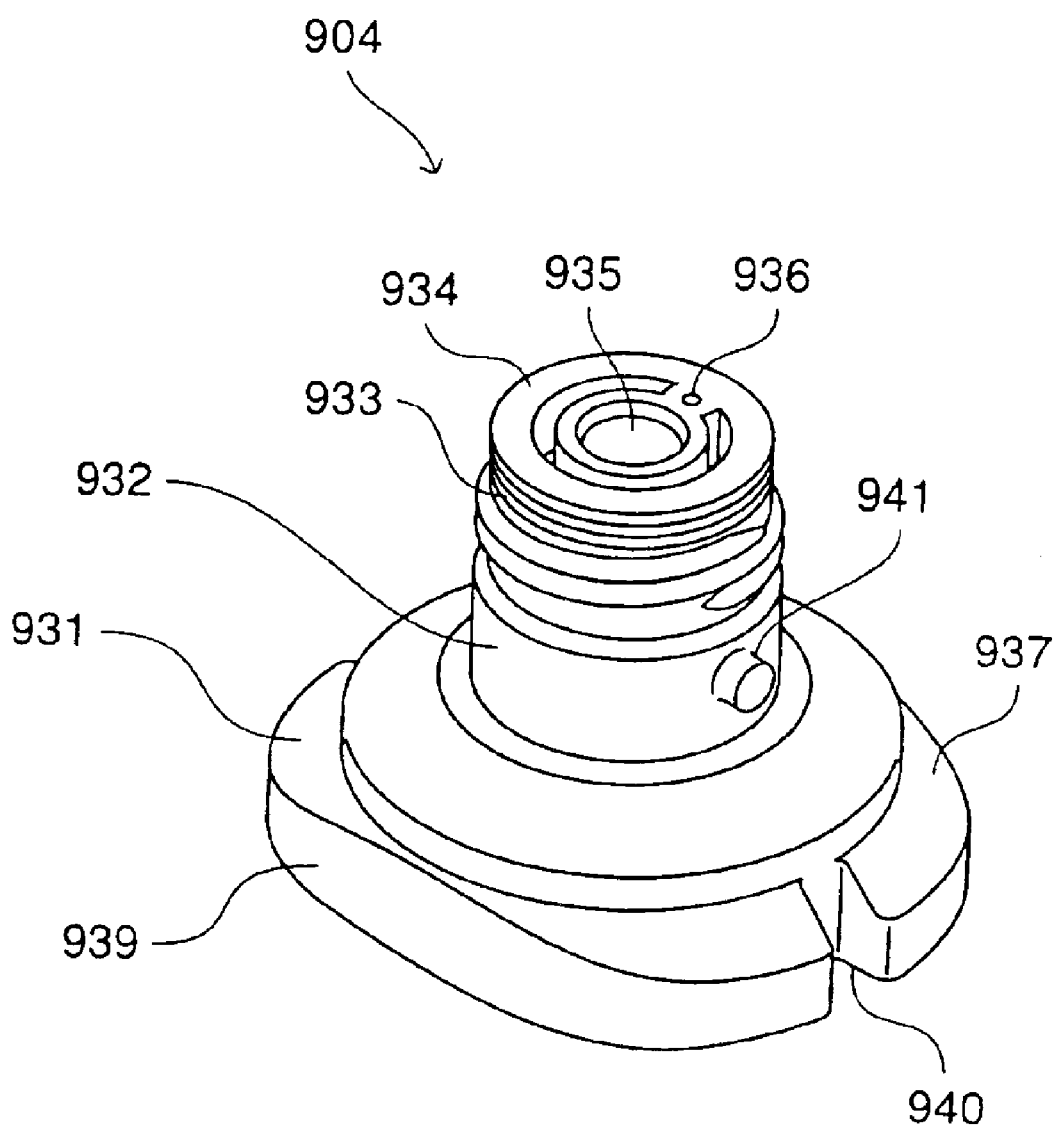
FIG. 63 is a diagram illustrating the construction of a small container employed for the container housing unit according to this invention.

Next, the configurations of the respective containers will be described. FIG. 62 illustrates the construction of the large container, and FIG. 63 illustrates the construction of the small container. These containers are disposable containers produced, for example, by blow-molding of HDPE (high density polyethylene) or a like plastic. The large containers 902, 903 each have a generally rectangular tank portion (container body) 910 for containing a reagent, and a small-diameter mouth portion 911 provided on an upper portion of the container body 910 for taking the reagent in and out of the container body. The mouth portion 911 has a thread 912 provided on an outer circumference thereof. When the large container 902, 903 is to be sealed, an outer cap not shown is threadingly fitted around the mouth portion 911. When the large container 902, 903 is in use, an inner cap 913 is fitted in the mouth portion 911 to close the mouth portion 911. The container body is not necessarily required to be of a rectangular shape but may be of a cylindrical shape.

Figure 69:
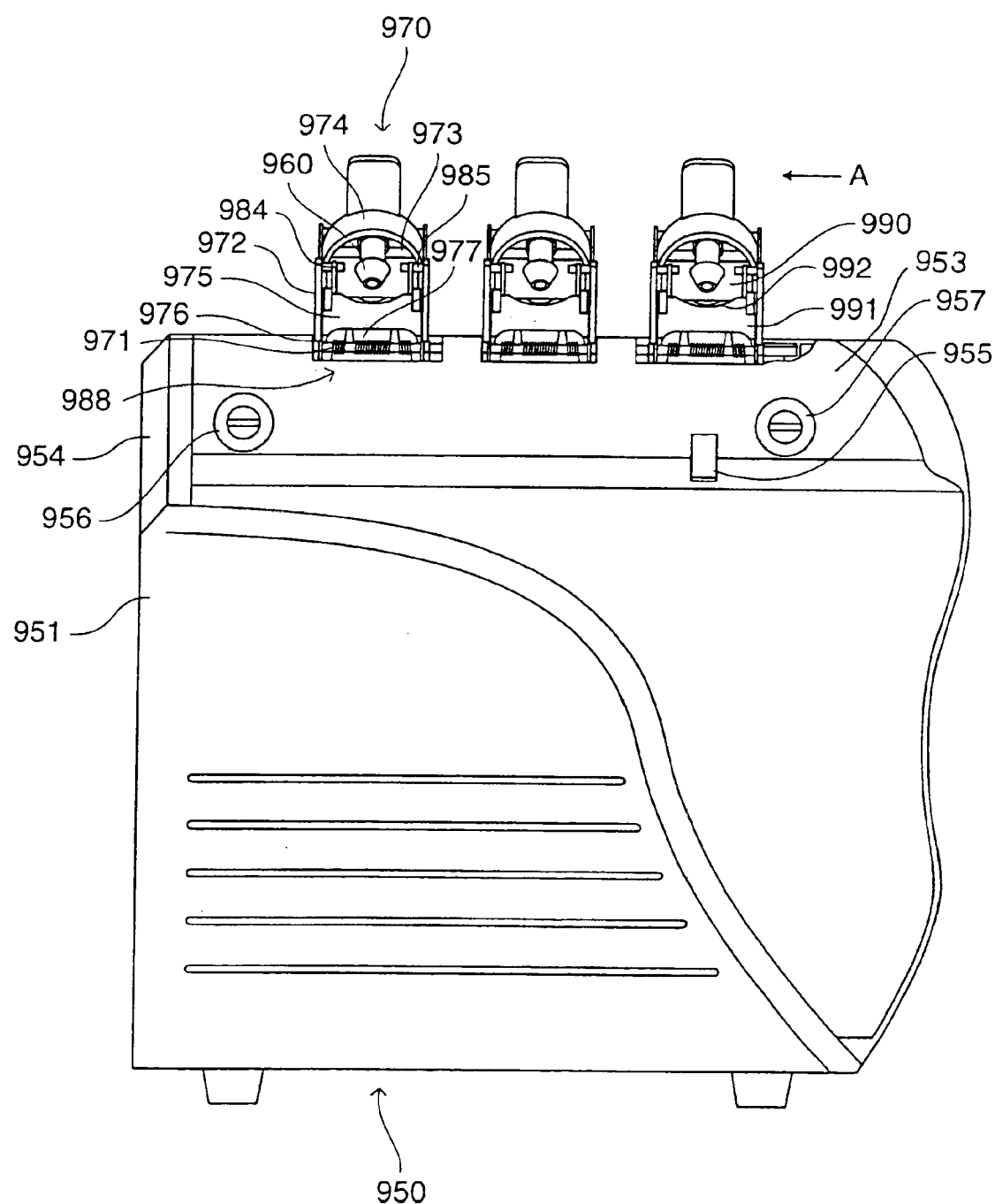
FIG. 69 is a front view of the container holder to which flow path connection mechanisms are attached.

The large container 902, 903 of FIG. 62 has a shoulder projection 923 provided on a shoulder thereof. The shoulder projection 923 prevents the container housing unit 100 from being set in a wrong orientation in the container holder 950. The container holder 950 of FIG. 69 is provided with three guide mechanisms 970. The containers 902, 903, 904 are exclusively used for the waste liquid, the hemolyzing agent and the diluent, respectively. Therefore, the containers 902, 903, 904 should be set in the container holder 950 so as to be properly connected to the guide mechanisms 970 for the respective uses. Without the shoulder projections 923, there would be a possibility that the container housing unit 100 is set in a wrong orientation to result in erroneous connection for the waste liquid and the diluent. However, if the inner case 100 (FIG. 61) accommodating the large containers 902, 903 with the shoulder projections 923 of the large containers oriented in the same direction is set in a wrong orientation in the container holder 950, the shoulder projections 923 of the large containers 902, 903 abut against projections 955 (having the same height as the shoulder projections 923 of the large containers 902, 903) projecting inward from a wall of the container holder 950 as shown in FIG. 69, so that the container housing unit 100 cannot be set in the container holder 950. Thus, the container housing unit 100 is prevented from being set in a wrong orientation in the container holder 950.

Figure 64:
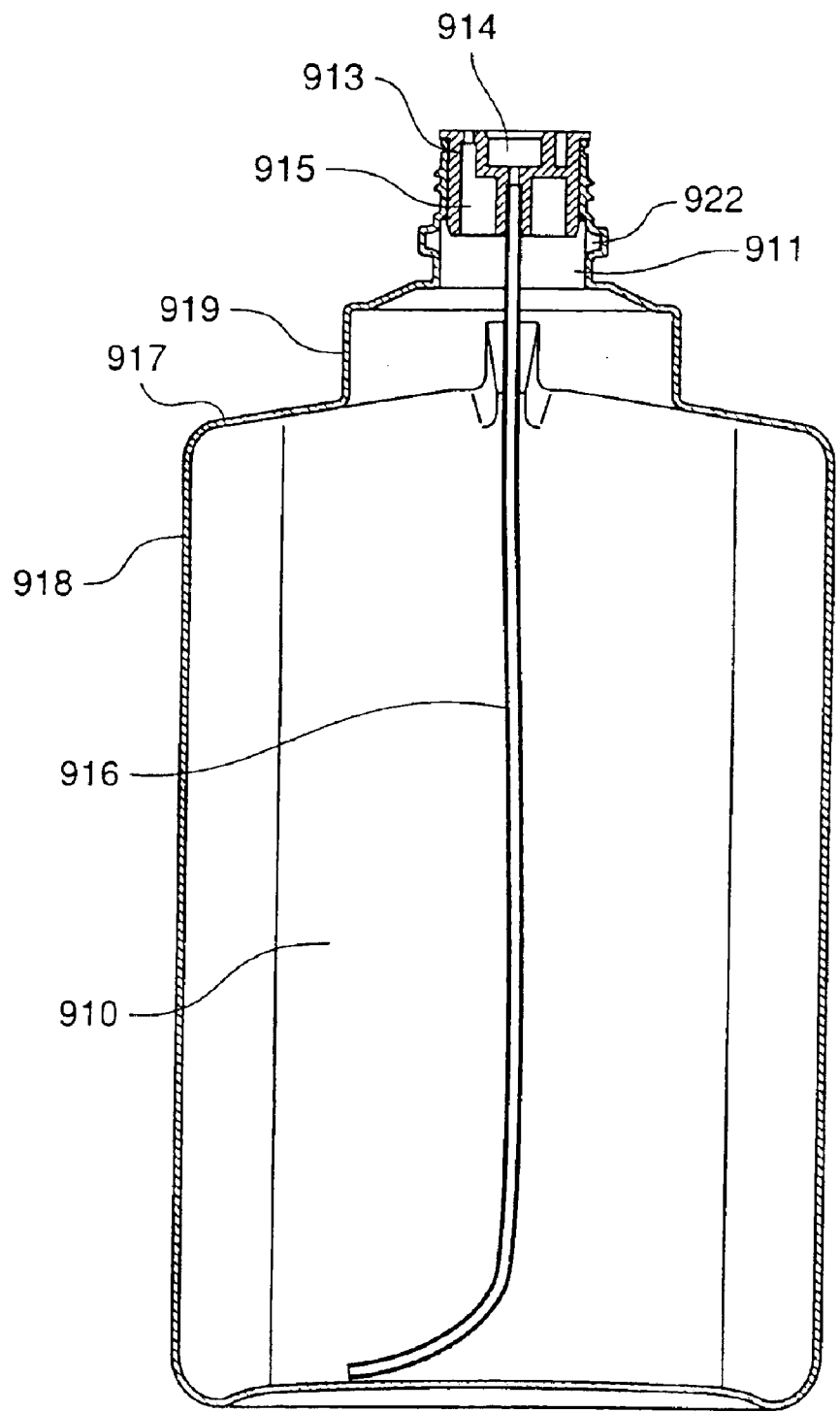
FIG. 64 is a sectional view of the large container fitted with an inner cap.

FIG. 64 is a sectional diagram of the large container 902, 903 capped with the inner cap 913. The inner cap 913 is required to be flexible and resistant to the reagents to be used, and is preferably composed, for example, of a silicone rubber. The inner cap 913 has a fluid passage hole 914 and a vent hole 915. The vent hole 915 permits air communication for prevention of pressure reduction or increase in the container when the reagent passes through the fluid passage hole 914.

A flow path tube 916 serving as a flow path connected to the fluid passage hole 914 is suspended within the large container 902, 903 (container body 910). A distal end of the flow path tube 916 reaches the bottom of the container, so that the reagent can be sucked out through the flow path tube 916 even if the reagent is left in a small amount. Examples of the tube include a urethane tube, a silicone tube and a tetrafluoroethylene tube.

A shoulder portion 917 extends radially outwardly from a lower portion of the mouth portion 911, and is followed by a container side wall 918. The container body 910 is defined by a space within the container side wall 918. The shoulder portion 917 has a neck 919 provided around the mouth portion 911. When the small container 904 is rested on the shoulder portion 917, the neck 919 serves to fix the small container 904 in abutment against a side wall of the small container 904 (a small container side wall portion to be described later) (see FIG. 67). The outer diameter (outer dimensions) of the neck 919 is determined in accordance with the outer diameter (outer dimensions) of the small container 904. A container projection 922 (which will be describer later) is provided on a side wall of the mouth portion 911 of the large container.

Figure 65:
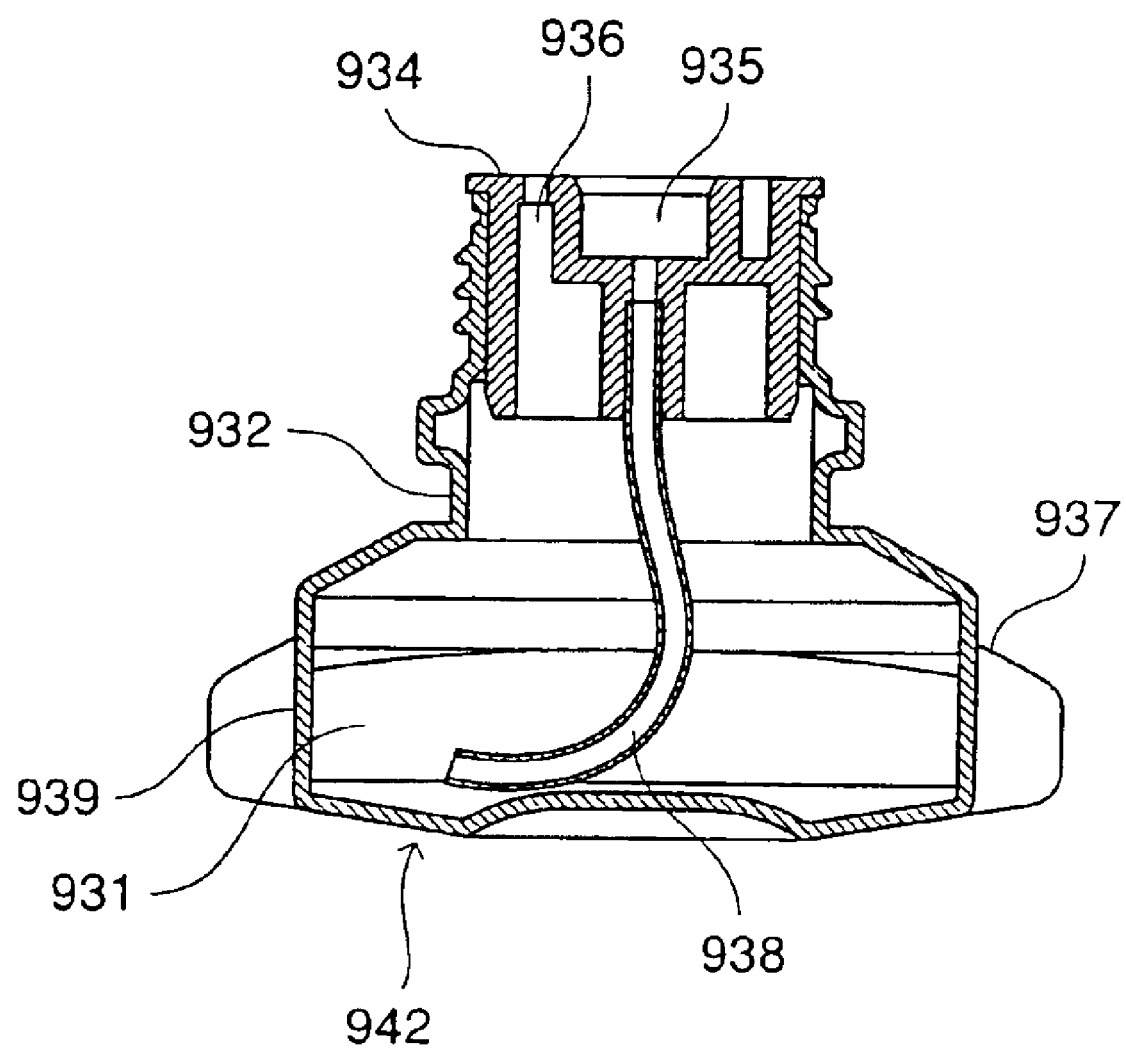
FIG. 65 is a sectional view of the small container fitted with an inner cap.

On the other hand, the small container 904 shown in FIG. 63 has a container side wall 939 defining therein a tank portion (container body 931) for storing a reagent, and a small-diameter mouth portion 932 provided on the container body 931 for taking the reagent in and out of the container portion. As can be seen from a sectional view in FIG. 65, the small container 904 has a generally planar bottom face 942 so as to be rested on a planar surface. The bottom face is not necessarily required to have a perfect planarity, but the configuration of the bottom face is determined by a positional relationship with respect to portions (small container mounting portions 924) of the shoulder portions 917 of the large containers 902, 903 on which the small container is mounted. Where the small container mounting portions 924 of the shoulder portions of the large containers are somewhat inclined, the bottom face 942 of the small container 904 is configured in conformity with the inclination. Thus, the generally planar bottom face may slightly be undulated, curved or inclined. The configuration of the small container mounting portions 924 is not limited to a generally planar configuration, but may be such that the small container 904 can be disposed between the two large containers 902 and 903 disposed in juxtaposition. Therefore, the configuration of the bottom face 942 of the small container 904 is not limited to the generally planar configuration, but may be configured in conformity with the configuration of the small container mounting portions 924. The small container 904 is employed as the hemolyzing agent container B3 shown in FIG. 29.

A thread 933 provided around the mouth portion 932, an inner cap 934, a fluid passage hole 935, a vent hole 936, a shoulder portion 937, a flow path tube 938 and a container projection 941 have substantially the same constructions and functions as those of the large container 902, 903 and, therefore, no explanation will be given thereto.

The container side wall 939 of the small container 904 is of a generally disk shape, and has a diameter defined so as to be brought into contact with the necks 919 of the large containers 902, 903 as describe above (see FIG. 61).

The neck 919 and the container side wall 939 of the small container 904 are each illustrated as having a circular configuration in the figures, but the configurations of the neck 919 and the container side wall 939 are not limited thereto. For example, the neck 919 and the container side wall 939 may be of a polygonal configuration, and dimensioned so that the neck 919 and the container side wall 939 can be brought into contact with each other.

As described above, portions of the shoulder portions 917 extending radially outwardly from the necks 919 of the large containers 902, 903 each have a generally planar configuration, and the bottom face of the small container 904 has a generally planar configuration in conformity with the shoulder portions 917. Therefore, the small container 904 can easily be mounted on the shoulder portions 917 of the large containers 902, 903.

Projections 920 are respectively provided on portions of the necks 919 of the large containers 902, 903 which are brought into contact with the small container 904. On the other hand, the small container 904 is formed with recesses 940 engageable with the projections 920. Therefore, the small container 904 can be held between the necks 919 with the recesses 940 thereof engaged with the projections 920 thereby to be assuredly fixed between the large containers 902, 903 without lateral displacement thereof.

Alternatively, a ring-shaped projection may be provided on the generally planar regions of the shoulder portions 917 in conformity with the outer periphery of the small container 904 for limitation of the lateral displacement.

Further, flanges 921 are respectively provided on upper portions of the projections 920 provided on the necks 919 of the large containers 902, 903. The flanges 921 respectively overlie parts of the small container 904 to prevent not only the lateral displacement but also the vertical displacement of the small container 904.

Next, an explanation will be given to how to accommodate the large containers 902, 903 and the small container 904 in the inner case 901.

The two large containers 902, 903 are placed in spaced juxtaposed relation so that faces (contact faces indicated by a reference character S in FIG. 61) of the large containers 902, 903 to be brought into contact with each other when the large containers 902, 903 are accommodated in the inner case 901 are spaced a small distance (about 1 cm).

In turn, the small container 904 is rested on an intermediate planar region between the shoulder portions 917 of the two large containers 902, 903.

Then, the two large containers 902, 903 are carefully moved toward each other to be brought into contact with each other, so that the projections 920 provided on the necks 919 of the large containers 902, 903 are fitted in the recesses 940 formed in the container side wall 939 of the small container 904.

Figure 66:
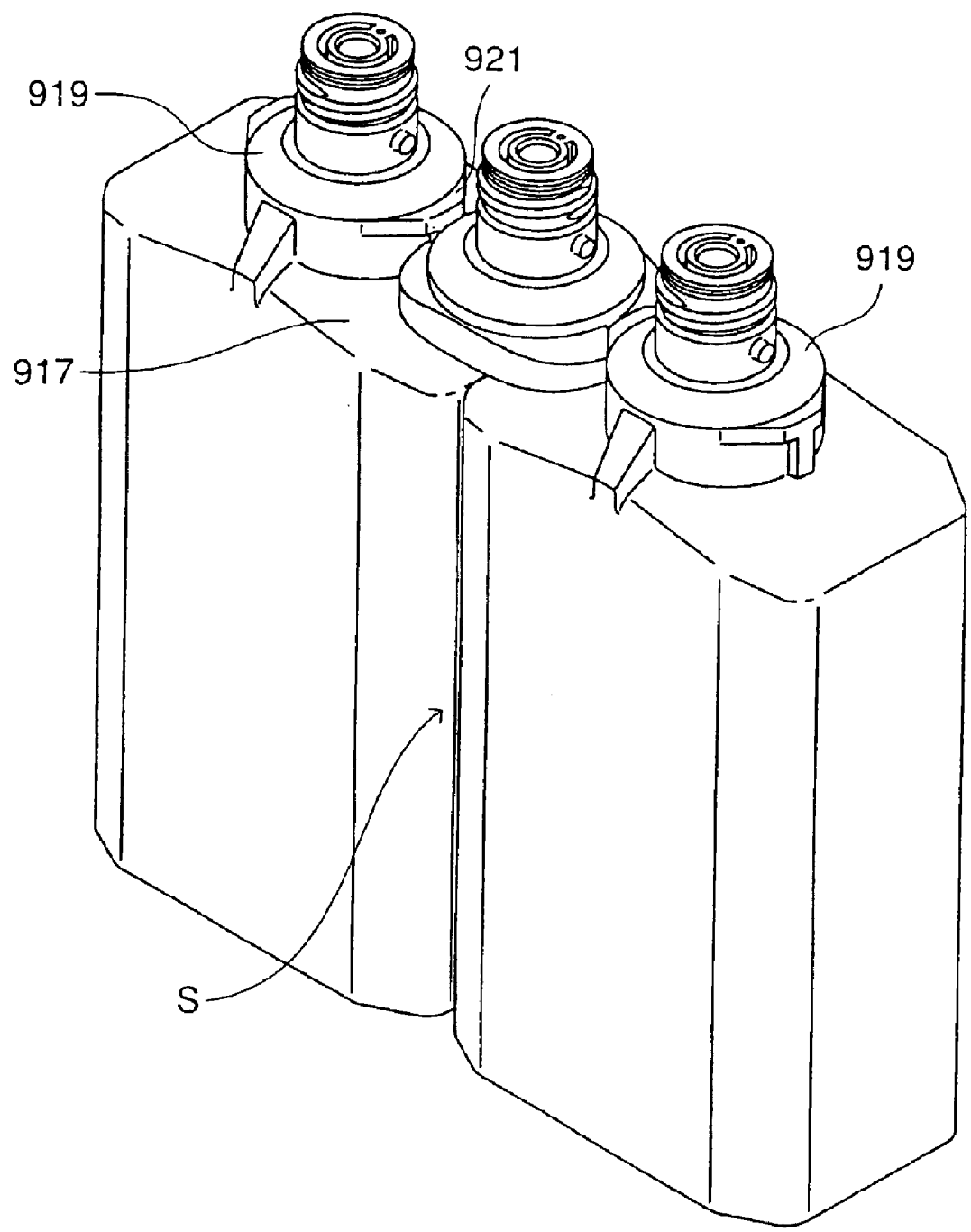
FIG. 66 is a perspective view illustrating a state where two large containers and one small container are housed in an inner case.
Figure 67:
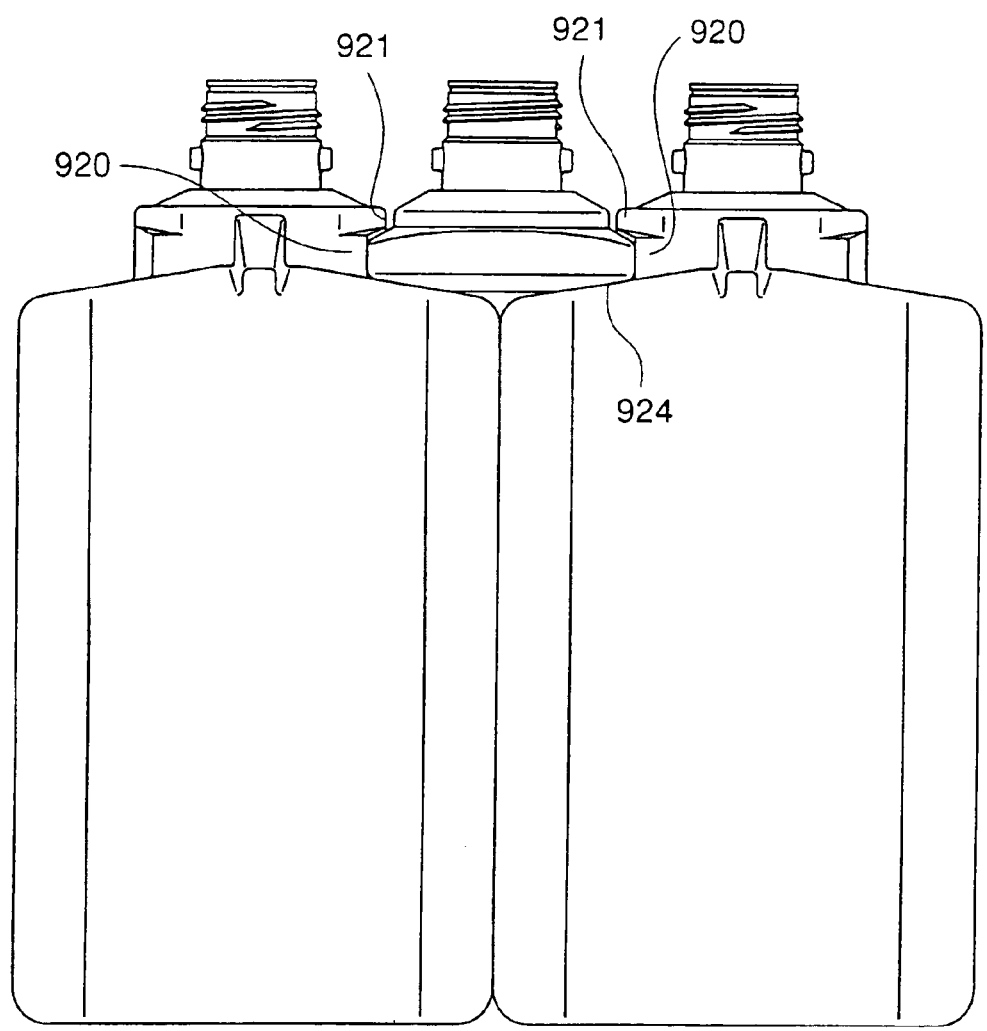
FIG. 67 is a front view illustrating the state where the two large containers and the one small container are housed in the inner case.
Figure 68:
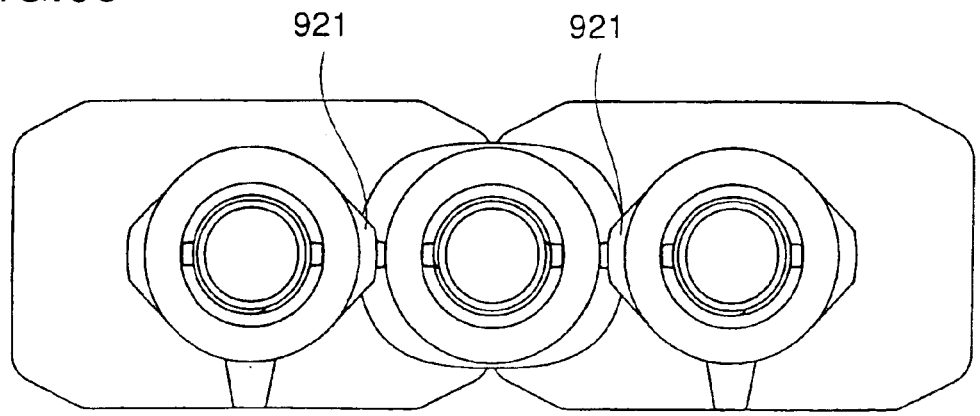
FIG. 68 is a plan view illustrating the state where the two large containers and the one small container are housed in the inner case.

FIG. 66 is a perspective view illustrating a state where the faces S of the two large containers 902, 903 are in contact with each other. FIGS. 67 and 68 are a front view and a plan view, respectively, illustrating this state. With the faces S of the two large containers 902, 903 in contact with each other, the small container 904 is fixed by the necks 919, the projections 920 and the flanges 921. In this state, the two large containers 902, 903 are lifted and inserted into the inner case 901.

The inner case 901 and the two large containers 902, 903 are properly dimensioned so that the large containers 902, 903 are fitted in the inner case 901. Therefore, the large containers 902, 903 and, hence, the small container 904 are properly positioned simply by inserting the large containers 902, 903 in the inner case 901. Thus, the large containers 902, 903 and the small container 904 are accommodated in the inner case 901 with the small container 904 being mounted on the shoulder portions 917 of the large containers 902, 903.

Container Holder

Next, an explanation will be given to the container holder attached to the analyzer body 1 for holding the container housing unit 100. The appearance of the container holder (including the container housing unit 100) is shown in FIG. 61, and the appearance of the container holder (excluding the container housing unit 100) is shown in FIG. 69. The container housing unit 100 is accommodated in the container holder 950. In use, the container holder 950 is fixed to the blood analyzer body 1, as shown in FIG. 3, by fixture screws 956, 957.

The container holder 950 has a generally rectangular box shape having six faces. Out of the six faces, a front wall 951 has an upper right portion arcuately cut away, and a bottom wall 952, a rear wall 953 and a left side wall 954 are present with a top face and a right side face being open.

The container holder 950 has inner dimensions which conform with the outer dimensions of the inner case 901 of the container housing unit 100. The inner case 901 of the container housing unit 100 is inserted into the container holder 950 from the right side face to abut against the left side wall 954. Thus, the inner case 901 can properly be positioned in the container holder 950.

Therefore, the mouth portions 911 of the large containers 902, 903 fitted in the inner case 901 and the mouth portion 932 of the small container 904 fixed to the large containers 902, 903 are brought into a predetermined positional relationship with respect to the guide mechanisms attached to the container holder 950.

The handle hole 906 of the inner case is exposed from the cut-away portion of the front wall 951, so that the user can easily draw out the container housing unit 100 with his finger inserted in the handle hole 906.

Flow Path Connection Mechanisms

Next, an explanation will be given to the flow path connection mechanisms for the fluid communication between the containers and the blood analyzer body 1 for supplying the reagents into the analyzer body 1 from the reagent containers and draining the waste liquid from the analyzer body 1 into the waste liquid container.

The flow path connection mechanisms are each constituted by components provided in the container and components provided outside the container. The components provided in the containers have already been described with reference to FIGS. 64 and 65. More specifically, the fluid passage hole 914, the inner cap 913 having the vent hole 915 and the flow path tube 916 suspended from the inner cap 913 shown in FIG. 64, or the fluid passage hole 935, the inner cap 934 having the vent hole 936 and the flow path tube 938 suspended from the inner cap 934 shown in FIG. 65 constitute a part of the flow path connection mechanism.

The components of the flow path connection mechanisms provided outside the containers are shown in a perspective view of FIG. 61 and a front view of FIG. 69. These and other figures are employed for the following explanation. The flow path connection mechanisms each include a nozzle 960 and a guide mechanism 970.

The guide mechanism 970 is attached to a notch 988 formed on an upper edge of the wall 953 of the container holder 950. Three flow path connection mechanisms are provided as corresponding to the three containers in the figures. However, an explanation will be given to only one of the flow path connection mechanisms for the large container, because the flow path connection mechanisms have the same construction.

FIGS. 70 to 73 illustrate the construction of the guide mechanism 970 of the flow path connection mechanism as seen from the right side thereof (in an arrow direction A) in FIGS. 61 and 69. These figures will also be employed for explaining the operation of the guide mechanism 970. FIG. 74 is a central sectional view of the guide mechanism 970 (as seen when the guide mechanism assumes a position shown in FIG. 73 as will be described later).

The nozzle 960 will first be explained. The nozzle 960 is provided within the guide mechanism 970 (FIG. 61). The nozzle 960 has a generally cylindrical shape, and has a flow path 961 provided therein as illustrated in section in FIG. 74. One end of the flow path 961 is inserted into the fluid passage hole 914 (FIG. 64), and the other end of the flow path 961 is connected to an inlet/outlet port of the blood analyzer body 1 via a tube. A nozzle tip 962 to be inserted into the fluid passage hole 914 is tapered for easy insertion in the fluid passage hole 914.

The flow path 961 of the nozzle 960 is bent at a right angle in the midst of the nozzle, and is connected to a port 964 provided in an axially middle portion of a cylindrical side wall of the nozzle 960. The tube for fluid communication with the blood analyzer body 1 is attached to the port 964. The nozzle 960 has a support hole 963 provided in a tail portion thereof. A second shaft 973 to be described later extends through the support hole 963, so that the nozzle 960 is supported by the second shaft 973. Since the support hole 963 is provided in the tail portion of the nozzle 960, the nozzle tip 962 directs vertically downward by gravity.

With reference to FIGS. 61 to 70, an explanation will be given to the guide mechanism 970. The guide mechanism 970 includes a first lever pivotally supported at one end thereof about a support member (first shaft) 971 fixed to the notch 988 formed in the wall 953 of the container holder 950, a second lever 974 pivotally supported about the second support member (second shaft) 973 attached to the other end of the first lever 972, and a third lever 975 supported at one end thereof about the first shaft 971 together with the first lever 972. A preferred example of a material for the support member and the second support member is SUS303. A preferred example of a material for the respective levers is an ABS resin.

As shown in FIGS. 61 and 69, the first lever 972, the second lever 974 and the third lever 975 support the nozzle 960 as surrounding the nozzle 960, and cover the inner cap 913 of the container.

The third lever 975 is located inward of the first lever 972. The second lever 974 is located inward of the first lever 972. The third lever 975 has a stepped inner portion provided on a distal end portion thereof so as not to interfere with the second lever 974.

Figure 70:
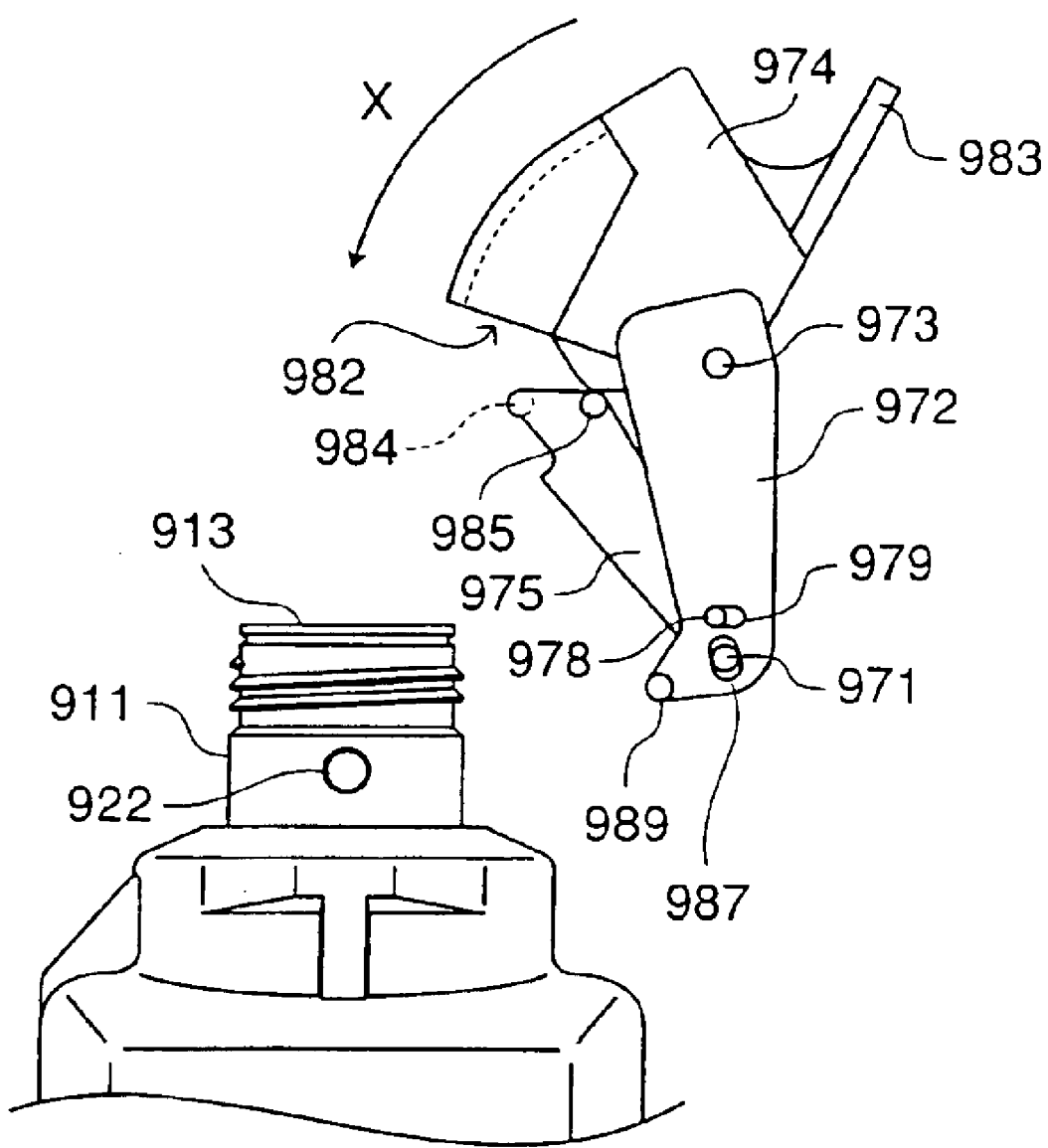
FIG. 70 is a diagram for explaining the construction and operation of a guide mechanism of the flow path connection mechanism.

With reference to FIGS. 69, 70 and 74, the first lever 972 will be described in further detail. The first lever 972 has elongated through-holes 987 through which the first shaft 971 extends. The through-holes 987 permit the first lever 972 to slightly move longitudinally thereof.

The first lever 972 has stoppers 989 provided in positions laterally spaced a small distance from the elongated through-holes 987. The stoppers 989 are brought into abutment against the rear face of the wall 953 for prevention of limitless pivotal movement of the first lever 972 when the flow path connection mechanism is lifted as shown in FIG. 70 (or FIG. 61).

The third lever 975 is supported by the first shaft 971 inward of the first lever 972. The third lever 975 has projections 978, and the first lever 972 has elongated through-holes 979 in which the projections 978 are fitted, so that the third lever 975 is prevented from limitlessly moving apart from the first lever 972. Therefore, the third lever 975 is permitted to move relative to the first lever 972 within an angular range such that the projections 978 are movable within the elongated through-holes 979.

A middle portion 990 (FIG. 69) extending widthwise between right and left portions of the first lever 972 has a planar shape.

With reference to FIGS. 69, 70 and 74, the second lever 974 will be described in further detail. The second lever 974 is supported by the second shaft 973.

The second lever 974 is of a cup-like shape, and has an inner space 980 (FIG. 74) for receiving the inner cap 913 therein. The nozzle 960 supported by the second shaft 973 is fixed within the inner space 980. With the inner cap 913 fitted in the inner space 980, the nozzle tip 962 is inserted into the fluid passage hole 914 (see FIG. 61).

As shown in FIG. 70, the second lever 974 has cloud-shaped recesses 982 provided in interior surfaces thereof to be brought into engagement with container projections 922 provided on a peripheral surface of the mouth portion 911 of the container. The recesses 982 have cloud-like curved contours so that the container projections 922 enter the recesses 982 and advance further inward into the recesses 982 as the second lever 974 is pivoted about the second shaft 973. Thus, the second lever 974 can be fixed to the large container 902 by the engagement with the container projections 922.

The second lever 974 has an arm 983 for easy pivoting operation of the second lever 974.

With reference to FIGS. 69, 70 and 74, the third lever 975 will be described in further detail. The third lever 975 has pressing portions 984 (see FIGS. 69 and 61) provided on the other end thereof for pressing the inner cap 913 in abutment against the inner cap 913, and support projections 985 (see FIGS. 69 and 70) for supporting the second lever 974 with the first lever 972 lifted.

The pressing portions 984 are configured as projections projecting inward so as to press the inner cap 913 which is to be located inward of the third lever 975 (see FIG. 61). On the contrary, the support projections 985 project outward so as to support the second lever 974 (see FIG. 69).

When the first lever 972 and the third lever 975 are moved toward each other (the projections 978 move rightward within the elongated through-holes 979), the positions of contacts between the support projections 985 and the second lever 974 vary little by little, and the support projections 985 support the second lever at the varying contact positions. On the other hand, support projection abutment surfaces R (see FIG. 74) of the second lever 974 to be brought into abutment against the support projections 985 are configured so that the second lever 974 can be pivoted counterclockwise as the contact positions vary.

A middle portion 991 (FIG. 69) connecting right and left portions of the third lever 975 has a planar shape. Further, the middle portion 991 has an arcuate cut-away portion 992 so as not to interfere with the mouth portion 911 of the container for prevention of collision against the mouth portion 911 when the third lever 975 is lowered (see FIG. 69).

Figure 75:
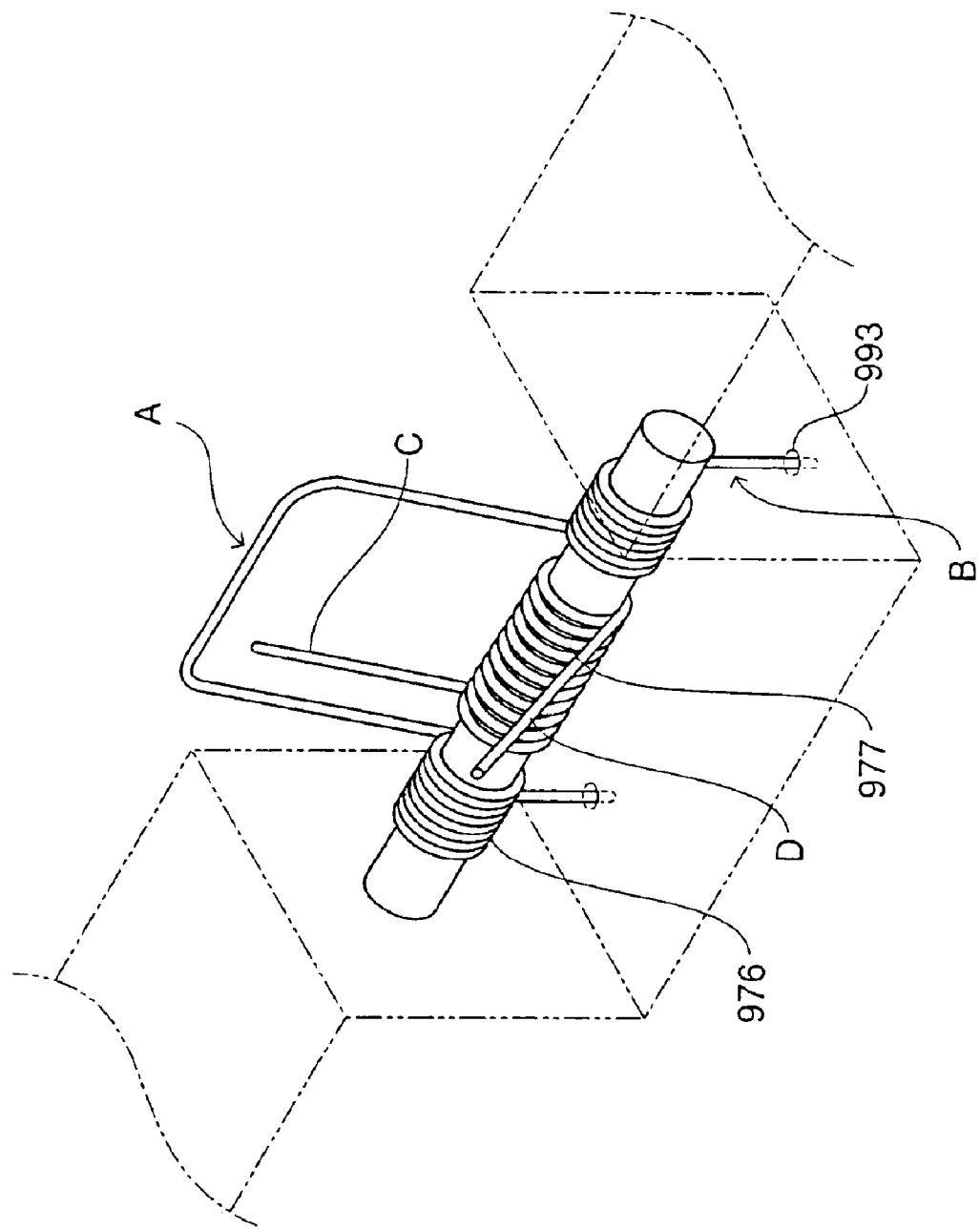
FIG. 75 is a diagram for explaining how biasing members are provided in the guide mechanism.
Figure 76:
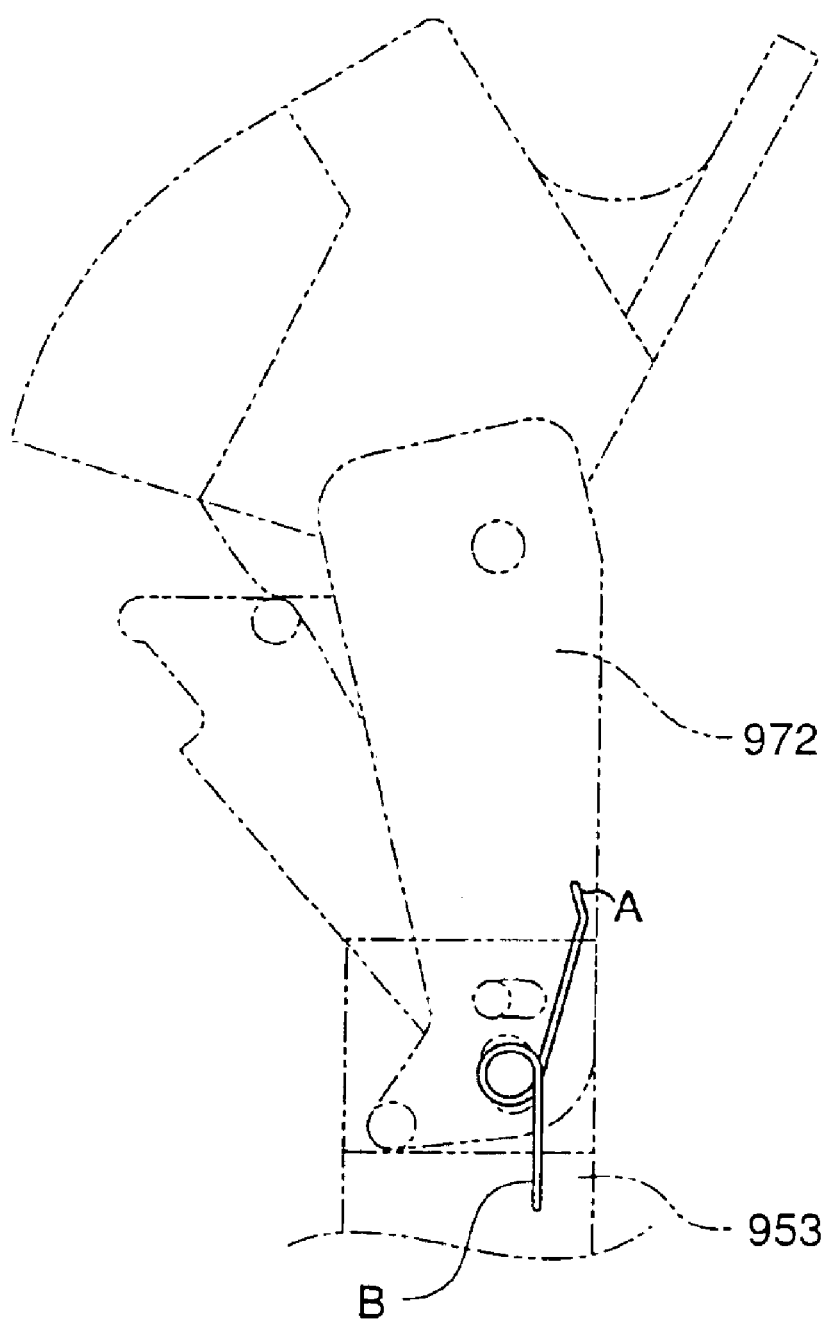
FIG. 76 is a diagram for explaining how a biasing member is provided in the guide mechanism.
Figure 77:
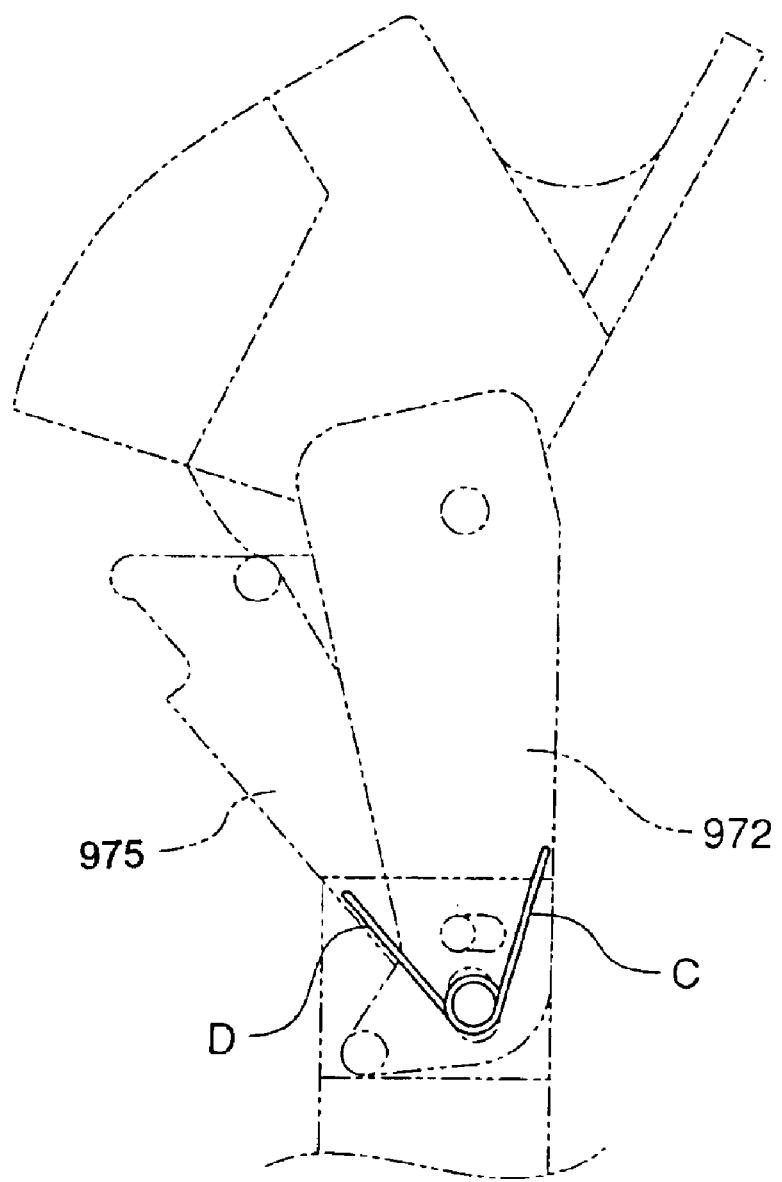
FIG. 77 is a diagram for explaining how a biasing member is provided in the guide mechanism.

A torsion spring 976 is fitted around the first shaft 971 for applying a biasing force to the first lever 972 with respect to the rear wall 953 in order to keep the guide mechanism 970 in a lifted state with the nozzle 960 not inserted in the fluid passage hole 914 (in a state shown in FIG. 61). A torsion spring 977 is fitted around the first shaft 971 for applying biasing forces to the first lever 972 and the third lever 975 away from each other with the guide mechanism 970 kept in the lifted state (FIGS. 75 to 77).

These two springs are configured so as not to interfere with each other. That is, the torsion spring 976 has right and left coil portions wound around two separate portions of the first shaft 971, and a middle portion A extending outward from a coil axis to be detoured as shown in FIG. 75.

The torsion spring 977 has an ordinary straight coil shape, and is located inward of the detoured middle portion A of the torsion spring 976. As shown in FIGS. 76 and 77, the middle portion A of the torsion spring 976 is supported in abutment against the middle portion 990 of the first lever 972, and end portions B of the torsion spring 976 are fixed in coil fixing portions 993 (FIG. 75) formed in the wall 953 (FIG. 69). End portions C and D of the torsion spring 977 are supported in abutment against the middle potion 990 of the first lever 972 and the middle portion 991 of the third lever 975, respectively.

Next, an explanation will be given to the guide mechanism. As shown in FIGS. 70 to 73, the guide mechanism 970 is gradually pivoted from a free position (a lifted position), and the nozzle 960 is inserted into the fluid passage hole 914 (FIG. 64). Then, the container projections 922 are brought into engagement with the cloud-shaped recesses 982 of the second lever 974.

FIG. 70 illustrates a state where the guide mechanism 970 is located in the free position. The first lever 972 is biased away by the biasing force of the torsion spring 976 (FIG. 75) fitted around the first shaft 971, and kept still with the stoppers 989 in abutment against the rear face of the wall 953 (FIG. 69).

At this time, the third lever 975 is biased away from the first lever 972 by the biasing forces of the torsion spring 977 (FIG. 75) fitted around the first shaft 971, and kept still with the projections 978 in abutment against ends of the elongated through-holes 979.

The second lever 974 is supported about the second shaft 973, and further supported by the support projections 985 with parts thereof abutting against the support projections 985 of the third lever 975 by gravity.

When the user pivots the second lever 974 in an arrow direction X by holding the arm 983 of the second lever 974 in this state, the support projections 985 are kept abutting against the second lever 974 for a while, so that the first lever 972, the second lever 974 and the third lever 975 are unitarily pivoted.

Figure 71:
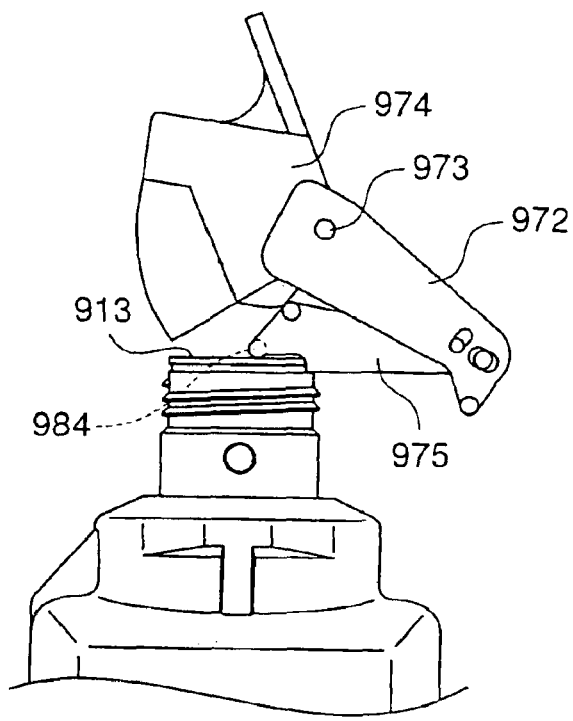
FIG. 71 is a diagram for explaining the construction and operation of the guide mechanism of the flow path connection mechanism.

FIG. 71 illustrates a state where the third lever 975 is pivoted to be oriented generally horizontally into contact with the inner cap 913. When the third lever 975 is brought in contact with the inner cap 913, the inner cap 913 is pressed by the pressing portions 984. The inner cap 913 prevents further pivoting of the third lever 975.

Therefore, the first lever 972 starts pivoting against the biasing forces of the torsion spring 977 acting on the/first lever 972 and the third lever 975, when a force is applied to the arm 983 of the second lever 974. That is, an angle defined between the first lever 972 and the third lever 975 is reduced, so that the first lever 972 is overlapped with the third lever 975. Finally, the first lever 972 is pivoted into abutment against the third lever 975 thereby to be oriented horizontally.

When the angle defined between the first lever 972 and the third lever 975 is reduced, distances between the support projections 985 and the second shaft 973 are reduced, and the positions of the contacts between the second lever 974 and the support projections 985 vary along the support projection abutment surfaces R shown in FIG. 74. Thus, the second lever 974 is permitted to pivot about the second shaft 973 as the contact positions vary.

In the state shown in FIG. 71, the pivoting of the first lever 972 about the first shaft 971 is associated with the pivoting of the second lever 974 about the second shaft 973.

Shortly after the reduction in the angle defined between the first lever 972 and the third lever 975 is started, the nozzle tip 962 (FIG. 74) is brought into contact with the inner cap 913. Since the nozzle tip 962 is tapered, the nozzle 960 is guided by the tapered nozzle tip thereof to be inserted into the fluid passage hole 914 (FIG. 64).

Since the first lever 972 is supported about the first shaft 971 extending through the elongated through-holes 987, the first lever 972 has a freedom of longitudinal movement (longitudinal play). This freedom permits the nozzle 960 to be smoothly inserted into the fluid passage hole 914.

Figure 72:
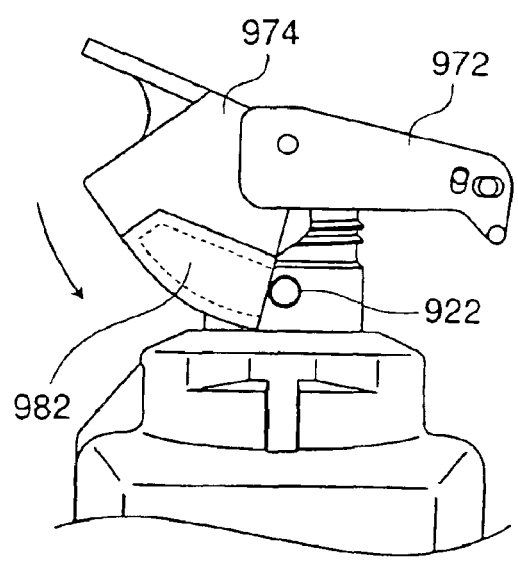
FIG. 72 is a diagram for explaining the construction and operation of the guide mechanism of the flow path connection mechanism.

FIG. 72 illustrates a state where the first lever 972 is pivoted to be oriented generally horizontally in abutment against the third lever 975. In this state, the nozzle 960 is completely inserted into the fluid passage hole 914.

With the first lever 972 abutting against the third lever 975, the first lever 972 is prevented from being further pivoted. The support projections 985 and the second shaft 973 are located in the closest relation, and the second lever 974 is brought out of abutment against the support projections 985.

Thereafter, only the pivoting of the second lever 974 about the second shaft 973 is permitted, whereby the container projections 922 enter the cloud-shaped recesses 982 of the second lever 974.

Figure 73:
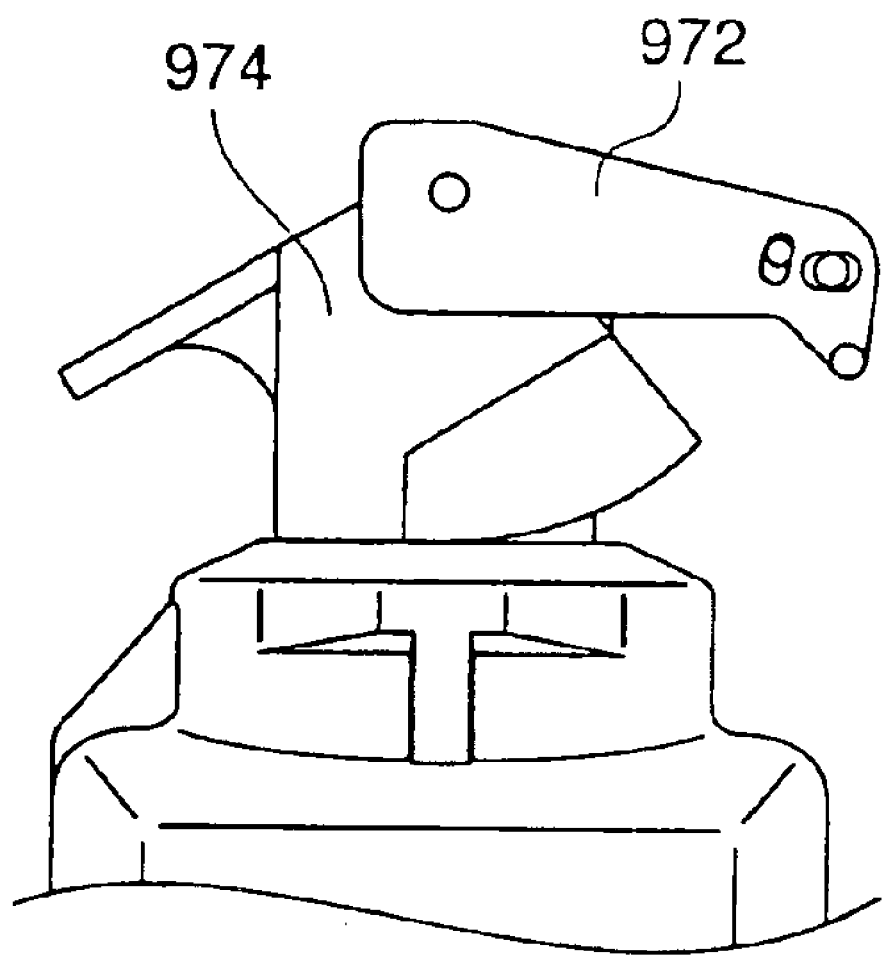
FIG. 73 is a diagram for explaining the construction and operation of the guide mechanism of the flow path connection mechanism.
Figure 74:
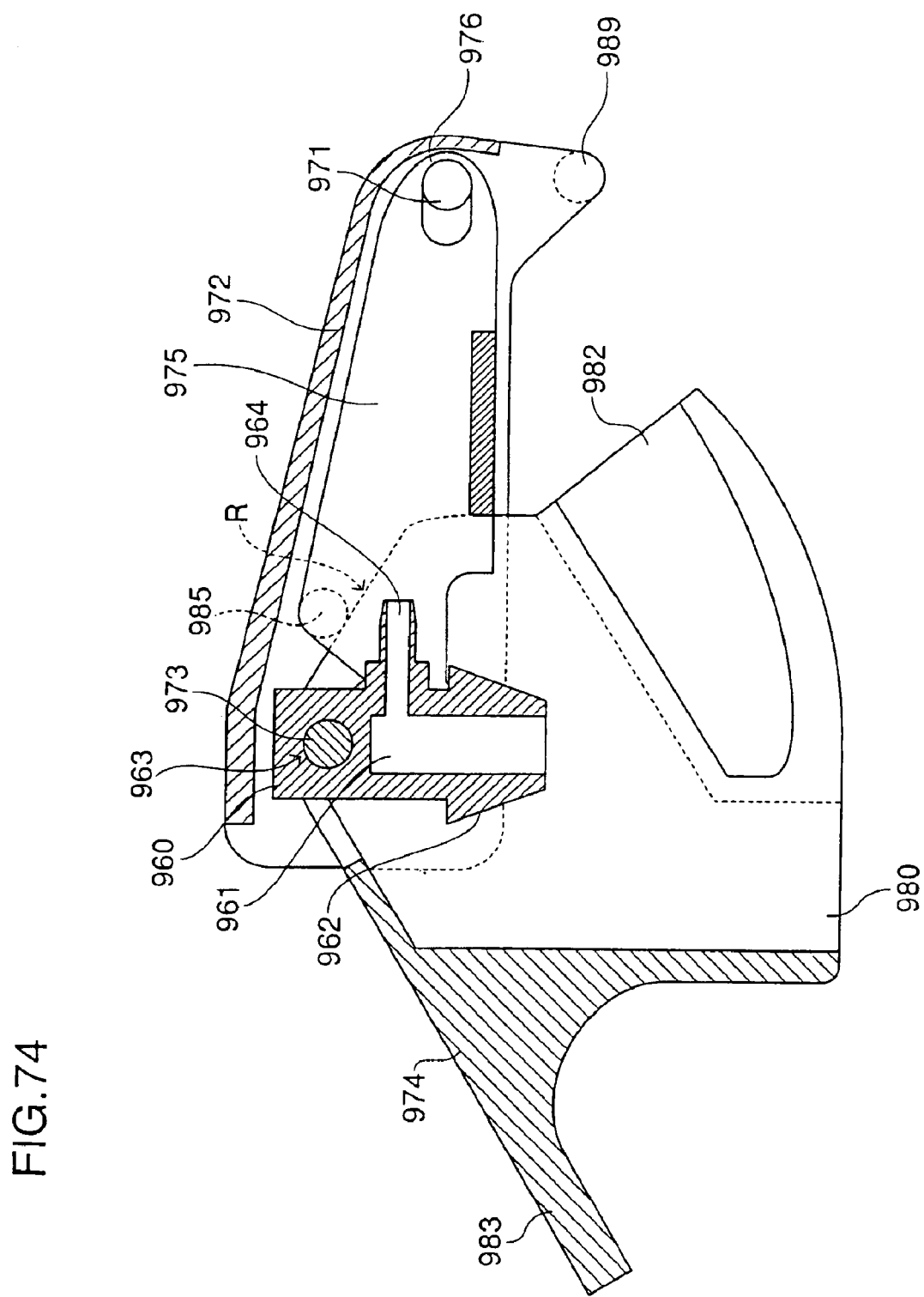
FIG. 74 is a central sectional view of the guide mechanism.

FIG. 73 illustrates a final state where the container projections 922 are fixed in the cloud-shaped recesses 982 of the second lever 974. The second lever 974 is further pivoted about the second shaft 973. Then, the container projections 922 are brought into abutment against the innermost portions of the cloud-shaped recesses 982, and fixed in this state (FIG. 74).

Thus, the nozzle 960 is inserted into the fluid passage hole 914 by the guide mechanism 970. As a result, the flow path tube 916 in the container (FIG. 64), the fluid passage hole 914 of the inner cap 913 and the nozzle 960 are connected to one another, thereby establishing a flow path to the blood analyzer body 1.

It is desirable that the torsion spring 977 is provided for applying the biasing forces to the first lever 972 and the third lever 975 away from each other as in this embodiment. However, this arrangement is not necessarily required for the unitary pivoting of the first lever 972, the second lever 974 and the third lever 975 in the state shown in FIG. 70, because the third lever 975 is brought away from the first lever 972 by gravity.

Relationship Between Container Housing Unit, Container Holder and Fluid Path Connection Mechanism As shown in FIG. 61, the container housing unit 100 is accommodated in a predetermined position of the container holder 950, whereby the mouth portions 913 of the large containers 902, 903 and the mouth portion 932 of the small container 904 are properly positioned. The guide mechanisms 970 of the flow path connection mechanisms are provided in association with the mouth portions 913, 932. Therefore, the user can insert the nozzles 960 into the fluid passage holes 914, 935 of the inner caps 913, 934 of the containers simply by setting the container housing unit 100 in the container holder 950 and pivoting the guide mechanisms 970.

What is claimed is:

1. A sample analyzer comprising: an input section; a display section; and a control section, wherein the control section controls the display section so that the display section displays a measurement screen for representing measurement results and changes the measurement screen to a main screen if no input operation is performed on the input section before a predetermined situation occurs in the sample analyzer after the measurement screen is displayed.

2. A sample analyzer as set forth in claim 1 further comprising a sensor for detecting an operation state of the sample analyzer, wherein the control section determines, on the basis of a signal provided from the sensor, that the predetermined situation occurs in the sample analyzer and changes the measurement screen to the main screen.

3. A sample analyzer as set forth in claim 1, wherein the display control section determines, after the lapse of a predetermined period from a predetermined point of time, that the predetermined situation occurs in the sample analyzer, and changes the measurement screen to the main screen.

4. A sample analyzer as set forth in claim 1, wherein the display control section controls the display section so that the display section changes the measurement screen to another measurement screen if the predetermined input operation is performed on the input section before the predetermined situation occurs in the sample analyzer.

5. A sample analyzer as set forth in claim 1, wherein the predetermined situation occurring in the sample analyzer is a situation in which a cleaning operation of the sample analyzer is completed.

6. A sample analyzer as set forth in claim 1 further comprising a touch panel input/display section, the touch panel input/display section including the input section and the display section.

* * * * *